(12) United States Patent
Ghobrial et al.

(10) Patent No.: US 11,124,838 B2
(45) Date of Patent: Sep. 21, 2021

(54) GENETIC ABNORMALITIES IN PLASMA CELL DYSCRASIAS

(71) Applicant: Dana-Farber Cancer Institute, Inc., Boston, MA (US)

(72) Inventors: Irene Ghobrial, Wellesley, MA (US); Salomon Manier, Lille (FR); Yuji Mishima, Tokyo (JP)

(73) Assignee: Dana-Farber Cancer Institute, Inc., Boston, MA (US)

( * ) Notice: Subject to any disclaimer, the term of this patent is extended or adjusted under 35 U.S.C. 154(b) by 76 days.

(21) Appl. No.: 15/742,815

(22) PCT Filed: Aug. 5, 2016

(86) PCT No.: PCT/US2016/045815
§ 371 (c)(1),
(2) Date: Jan. 8, 2018

(87) PCT Pub. No.: WO2017/027391
PCT Pub. Date: Feb. 16, 2017

(65) Prior Publication Data
US 2018/0305766 A1    Oct. 25, 2018

Related U.S. Application Data

(60) Provisional application No. 62/202,314, filed on Aug. 7, 2015.

(51) Int. Cl.
| | | |
|---|---|---|
| C12Q 1/68 | (2018.01) | |
| C07H 21/04 | (2006.01) | |
| A61P 35/02 | (2006.01) | |
| G01N 33/50 | (2006.01) | |
| G01N 33/574 | (2006.01) | |
| C12Q 1/6886 | (2018.01) | |
| C12Q 1/6883 | (2018.01) | |

(52) U.S. Cl.
CPC ............ *C12Q 1/6886* (2013.01); *A61P 35/02* (2018.01); *C12Q 1/6883* (2013.01); *G01N 33/5011* (2013.01); *G01N 33/5038* (2013.01); *G01N 33/5044* (2013.01); *G01N 33/574* (2013.01); *C12Q 2600/112* (2013.01); *C12Q 2600/118* (2013.01); *C12Q 2600/154* (2013.01); *C12Q 2600/156* (2013.01); *C12Q 2600/158* (2013.01); *G01N 2570/00* (2013.01); *G01N 2800/22* (2013.01); *G01N 2800/52* (2013.01); *G01N 2800/56* (2013.01); *G01N 2800/60* (2013.01); *G01N 2800/7028* (2013.01)

(58) Field of Classification Search
None
See application file for complete search history.

(56) References Cited

U.S. PATENT DOCUMENTS

| | | |
|---|---|---|
| 9,944,991 B2 | 4/2018 | Ghobrial et al. |
| 2013/0171124 A1 | 7/2013 | Cong et al. |
| 2014/0364139 A1 | 12/2014 | Lipman et al. |
| 2014/0364439 A1 | 12/2014 | Wu et al. |

FOREIGN PATENT DOCUMENTS

| | | |
|---|---|---|
| WO | WO2013/134786 | 9/2013 |
| WO | 2014/071205 | 5/2014 |
| WO | WO 2017/027391 | 2/2017 |

OTHER PUBLICATIONS

Mattos-Aruda et al. (Annals of Oncology, vol. 25, Issue 9, Sep. 2014, pp. 1729-1735) (Year: 2014).*
Gezer (Clinical Genetics, vol. 78, Suppl 1. Page 7, Abstract No. 1/07, Dec. 2010). (Year: 2010).*
Mishima et al. (Blood, vol. 122, No. 21, Abstract 533, Oct. 21, 2013). (Year: 2013).*
Vij et al. (Clinical Lymphoma, Myeloma & Leukemia, vol. 14, No. 2, pp. 131-139, Apr. 2014). (Year: 2014).*
Avet-Loiseau et al., *Combining fluorescent in situ hybridization data with ISS staging improves risk assessment in myeloma: an International Myeloma Working Group collaborative project*, Leukemia, 27(3):711-7 (2013).
Bolli et al., *Heterogeneity of genomic evolution and mutational profiles in multiple myeloma*, Nature Communications 5:2997 (2014).
Cancer Genome Atlas Research et al., *The Cancer Genome Atlas Pan-Cancer analysis project*, Nature Genetics 45(10):1113-1120 (2013).
Chapman et al., *Initial genome sequencing and analysis of multiple myeloma*, Nature 471(7339):467-472 (2011).
Cibulskis et al., *Sensitive detection of somatic point mutations in impure and heterogeneous cancer samples*, Nature Biotechnology 31(3):213-219 (2013).
Corre et al., *Genetics of multiple myeloma: another heterogeneity level?*, Blood 125(12):1870-1876 (2015).
D'haene et al., *miRNA expression profiling: from reference genes to global mean normalization*, Methods Mol. Biol., 822:261-72 (2012).
den Dunnen and Anonarakis, *Mutation nomenclature extensions and suggestions to describe complex mutations: a discussion*, Human Mutation 15(1):7-12 (2000).
Ghobrial et al, *How I treat smoldering multiple myeloma*, Blood 124(23):3380-8 (2014).
Griepp et al., *International staging system for multiple myeloma*, J. Clin. Oncol., 23(15):3412-20 (2005).

(Continued)

*Primary Examiner* — Jeanine A Goldberg
(74) *Attorney, Agent, or Firm* — Fish & Richardson P.C.

(57) ABSTRACT

Provided herein are non-invasive methods and biomarkers that identify progression and clonal evolution of plasma cell dyscrasias. Also provided are materials and methods for the diagnosis, prognosis, staging, and monitoring of plasma cell dyscrasias based on the presence of the bio markers in a blood biopsy, as well as methods for monitoring the progression of a plasma cell dyscrasia, determining the efficacy of a therapeutic agent, determining a targeted therapy related to a plasma cell dyscrasia, and/or treating a plasma cell dyscrasia. The methods provided herein provide several advantages over invasive biopsies.

4 Claims, 23 Drawing Sheets

(56) References Cited

OTHER PUBLICATIONS

Jenner et al., *Gene mapping and expression analysis of 16q loss of heterozygosity identifies WWOX and CYLD as being important in determining clinical outcome in multiple myeloma*, Blood 110(9):3291-3300 (2007).

Kahlert et al., *Identification of double-stranded genomic DNA spanning all chromosomes with mutated KRAS and p53 DNA in the serum exosomes of patients with pancreatic cancer*, Journal Biological Chemistry 289(7):3869-3875 (2014).

Kyle et al., *Criteria for diagnosis, staging, risk stratification and response assessment of multiple myeloma*, Leukemia, 23(1):3-9 (2009).

Landgren et al., *Monoclonal gammopathy of undetermined significance (MGUS) consistently precedes multiple myeloma: a prospective study*, Blood 113(22):5412-5417 (2009).

Landgren, *Monoclonal gammopathy of undetermined significance and smoldering multiple myeloma: biological insights and early treatment strategies*, Hematology Am Soc Hematol Educ Program 1:478-487 (2013).

Lazaro-Ibanez et al., *Different gDNA content in the subpopulations of prostate cancer extracellular vesicles: apoptotic bodies, microvesicles, and exosomes*, Prostate 74(14):1379-1390 (2014).

Leiserson et al., *Simultaneous identification of multiple driver pathways in cancer*, PLoS Computational Biology 9(5):e1003054 (2013).

Lohr et al., *Widespread genetic heterogeneity in multiple myeloma: implications for targeted therapy*, Cancer Cell 25(1):91-101 (2014).

Mohamed et al., *Chromosome aberrations in a series of 120 multiple myeloma cases with abnormal karyotypes*, American Journal of Hematology 82(12):1080-1087 (2007).

Murtaza et al., *Non-invasive analysis of acquired resistance to cancer therapy by sequencing of plasma DNA*, Nature 497(7447):108-112 (2013).

Omberg et al., *Enabling transparent and collaborative computational analysis of 12 tumor types within The Cancer Genome Atlas*, Nature Genetics 45(10):1121-1126 (2013).

Paiva et al., *High-risk cytogenetics and persistent minimal residual disease by multiparameter flow cytometry predict unsustained complete response after autologous stem cell transplantation in multiple myeloma*, Blood 119(3):687-691 (2012).

Paiva et al., *New criteria for response assessment: role of minimal residual disease in multiple myeloma*, Blood 125(20):3059-3068 (2015).

Paiva et al., *The prognostic value of multiparameter flow cytometry minimal residual disease assessment in relapsed multiple myeloma*, Haematologica 100(2):e53-55 (2015).

Palumbo et al., *Revised International Staging System for Multiple Myeloma: A Report From International Myeloma Working Group*, J. Clin. Oncol., 33(26):2863-9 (2015).

Taylor et al., *Exosome isolation for proteomic analyses and RNA profiling*, Methods Mol Biol., 728:235-46 (2011).

Walker et al., *A compendium of myeloma-associated chromosomal copy number abnormalities and their prognostic value*, Blood 116(15):e56-65 (2010).

Weiss et al., *A monoclonal gammopathy precedes multiple myeloma in most patients*, Blood 113(22):5418-5422 (2009).

International Search Report of ISA/US issued for PCT/US2016/045815 (dated Oct. 24, 2016), 3 pages.

Written Opinion of ISA/US issued for PCT/US2016/045815 (dated Oct. 24, 2016), 13 pages.

Ghobrial et al., "Myeloma as a Model for the Process of Metastasis: Implications for Therapy," Blood 120:20-30 (Jul. 5, 2012).

Bianchi et al., "Biological and Clinical Implications of Clonal Heterogeneity and Clonal Evolution in Multiple Myeloma," Current Cancer Therapy Reviews 10:70-9 (dated May 1, 2014).

Hosgood et al., "Genetic Variation in Cell Cycle and Apoptosis Related Genes and Multiple Myeloma Risk," Leukemia Research 33:1609-14 (dated Dec. 31, 2009).

Cifola et al., "Whole-Exome Sequencing of Primary Plasma Cell Leukemia Discloses Heterogeneous Mutational Patterns," Oncotarget 6:17543-58 (Jul. 10, 2015).

Chesi et al., "Molecular pathogenesis of multiple myeloma: basic and clinical updates", International Journal of Hematology., vol. 97, No. 3, Feb. 28, 2013 (Feb. 28, 2013), pp. 313-323.

Gross et al., "Automated Enumeration and Characterization of Circulating Multiple Myeloma Cells in Blood", Blood 2011 118:1825.

Kaedbey et al.: "Abstract 615: Noninvasive diagnosis of actionable mutations by deep sequencing of circulating tumor DNA in multiple myeloma," Cancer Research, Aug. 1, 2015 (Aug. 1, 2015), vol. 75(15), 4 pages.

Leich et al., "Multiple myeloma is affected by multiple and heterogeneous somatic mutations in adhesion- and receptor tyrosine kinase signaling molecules", Blood Cancer Journal, vol. 3, No. 2, Feb. 8, 2013 (Feb. 8, 2013), p. e102.

Mishima et al., "Molecular Analysis Of Circulating Tumor Cells Identifies Mutations That are Distinct From Those Present In The Bone Marrow of Patients With Multiple Myeloma," Blood 2013 122:533, Dec. 5, 2013 (Dec. 5, 2013).

Nowakowski, "Circulating plasma cells detected by flow cytometry as a predictor of survival in 302 patients with newly diagnosed multiple myeloma", Blood, vol. 106, No. 7, Jun. 16, 2005 (Jun. 16, 2005), pp. 2276-2279.

O'Donnell et al., "Targeting BRAF in Multiple Myeloma", Cancer Discovery, vol. 3, No. 8, Aug. 7, 2013 (Aug. 7, 2013), pp. 840-842.

Rustad et al., "BRAF V600E mutation in early-stage multiple myeloma: good response to broad acting drugs and no relation to prognosis", Leukemia., vol. 5, No. 3, Mar. 20, 2015 (Mar. 20, 2015), p. e299.

Szalat et al., "Genomic heterogeneity in multiple myeloma", Current Opinion in Genetics & Development., vol. 30, May 16, 2015 (May 16, 2015), pp. 56-65.

PCT International Preliminary Report on Patentability in Appl. No. PCT/US2016/045815, dated Mar. 20, 2018, 15 pages.

Valadi et al., "Exosome-mediated transfer of mRNAs and microRNAs is a novel mechanism of genetic exchange between cells," Nature Cell Biology, 2007, 9(6):654-659.

\* cited by examiner

GENETIC ABNORMALITIES IN PLASMA CELL DYSCRASIAS

CROSS-REFERENCE TO RELATED APPLICATIONS

This application is a U.S. National Stage application, and claims priority of International Application No. PCT/US2016/045815, filed Aug. 5, 2016, which claims the benefit of the priority of U.S. Provisional Appl. No. 62/202,314, filed Aug. 7, 2015. The contents of all of the prior applications are incorporated by reference herein in their entirety.

STATEMENT REGARDING FEDERALLY SPONSORED RESEARCH

This invention was made with government support under grant numbers R01 CA181683 and R01 CA154648 awarded by The National Institutes of Health. The government has certain rights in the invention.

TECHNICAL FIELD

This disclosure relates generally to non-invasive biopsies for the diagnosis, prognosis, and treatment of patients having plasma cell dyscrasias.

BACKGROUND

Plasma cell dyscrasias are disorders of plasma cells. Multiple Myeloma (MM) is a plasma cell dyscrasia characterized by patchy bone marrow infiltration leading to multiple bone lytic lesions and cytopenias at the time of diagnosis. Bone marrow biopsies are limited in that sampling allows assessment of only one site where the tumor clones can be different from those present in other areas of the bone marrow and may not be reflective of the total disease heterogeneity. It is also a painful procedure for patients and many patients with precursor state monoclonal gammopathy of undetermined significance (MGUS) or smoldering multiple myeloma (SMM) do not have bone marrow biopsies performed.

SUMMARY

Provided herein is a non-invasive method (e.g., a blood biopsy) to identify progression and clonal evolution of plasma cell dyscrasias. Also provided are materials and methods for the diagnosis, prognosis, staging, and monitoring of plasma cell dyscrasias based on the presence of biomarkers in a blood biopsy, as well as methods for monitoring the progression of a plasma cell dyscrasia, determining the efficacy of a therapeutic agent, determining a targeted therapy for a plasma cell dyscrasia, and/or treating a plasma cell dyscrasia.

The methods described herein provide several advantages over bone marrow biopsies. For example, a blood biopsy is a non-invasive procedure for which multiple sequential samples can easily be obtained. A blood biopsy allows one to determine a mutational profile of the majority if not all clones present in the bone marrow instead of sampling only one site of the bone marrow, and also allows one to monitor changes in the mutational profile over time which may be indicative of a change in the plasma cell dyscrasia (e.g., a response to a therapeutic agent, a progression of the plasma cell dyscrasia, etc.). A blood biopsy that gives critical information for diagnosis and prognosis and replaces bone marrow biopsies for patients with plasma cell dyscrasias represents a major advance in the diagnosis, prognosis and potentially treatment decision of patients having, or at risk of developing, plasma cell dyscrasias.

In one aspect, this disclosure provides a method of determining whether a human subject has, or is at risk of developing, a plasma cell dyscrasia. The method includes determining whether circulating free DNA (cfDNA), DNA or RNA from a circulating exosome, or DNA from a circulating tumor cell (CTC) from a blood biopsy from the subject has one or more gene abnormalities associated with a plasma cell dyscrasia. The method can include analysis of all or part of an exome. The method can include analysis of one or more genes of interest. The one or more gene abnormalities can be selected from the group consisting of a translocation (e.g., t(4;14), t(6;14), t(11;14), t(14;16), and/or t(14;20)), a copy number variation (CNV; e.g., 1q21 amplification, 1p32 deletion, 13q deletion, 16q deletion, and/or 17p deletion), a single nucleotide variation (SNV), and/or an epigenetic abnormality. In some cases an SNV is in a gene selected from the group consisting of KRAS, NRAS, BRAF, IRF4, MPEG1, RYR2, SLC24A1, FAT1, BCLAF1, CDC27, HLA-B, NBPF1, and/or ZFHX3 (e.g., KRAS (p.G12D), NRAS (p.G12D), KRAS (p.Q61H), BRAF (p.G469R), IRF4 (p.L116R), MPEG1 (p.G537E), RYR2 (p.I784V), SLC24A1 (p.R686G), FAT1 (p.V3464I), FAT (p.K2895R), BCLAF1 (p.N629S), CDC27 (p.A273G), HLA-B (p.K210N), NBPF1 (p.D679E), NBPF1 (p.K41R), NBPF1 (p.L648V), ZFHX3 (p.Q2007*), ZFHX3 (p.H2001N), and/or ZFHX3 (p.F1800L)). In some cases, an SNV is in a gene selected from the group consisting of CR1, DPY19L2, TMPRSS13 and/or HBG1 (e.g., CR1 (p.R2194*), CR1 (p.M2208T), DPY19L2 (p.I647V), TMPRSS13 (p.A77G), TMPRSS13 (p.Q78R), and/or HBG1 (p.A137G)). If the subject has one or more of the gene abnormalities in the CTC, cfDNA, or exoDNA or RNA/miRNA from the blood biopsy from the subject, the subject is determined to have or be at risk of developing a plasma cell dyscrasia (e.g., MGUS, SMM, MM). In some embodiments, the detection of the genetic abnormality or abnormalities in the cfDNA is performed by a method comprising whole exome sequencing or targeted deep sequencing.

In one aspect, this disclosure provides a method of treating a human subject having, or at risk of developing, a plasma cell dyscrasia. The method includes administering to the human subject a therapeutic agent targeted to a first gene or a gene product of the first gene, the first gene determined to have a one or more gene abnormalities in a CTC, cfDNA, or exoDNA or RNA/miRNA from a blood biopsy from the human subject; or administering to the human subject a therapeutic agent targeted to a second gene or a gene product of the second gene, the second gene being associated with the first gene. The one or more gene abnormalities can be selected from the group consisting of a translocation (e.g., t(4;14), t(6;14), t(11;14), t(14;16), and/or t(14;20)), a copy number variation (CNV; e.g., 1q21 amplification, 1p32 deletion, 13q deletion, 16q deletion, and/or 17p deletion), a single nucleotide variation (SNV), and/or an epigenetic abnormality. In some cases an SNV is in a gene selected from the group consisting of KRAS, NRAS, BRAF, IRF4, MPEG1, RYR2, SLC24A1, FAT1, BCLAF1, CDC27, HLA-B, NBPF1, and/or ZFHX3 (e.g., KRAS (p.G12D), KRAS (p.Q61H), NRAS (p.G12D), BRAF (p.G469R), IRF4 (p.L116R), MPEG1 (p.G537E), RYR2 (p.I784V), SLC24A1 (p.R686G), FAT1 (p.V3464I), FAT (p.K2895R), BCLAF1 (p.N629S), CDC27 (p.A273G), HLA-B (p.K210N), NBPF1 (p.D679E), NBPF1 (p.K41R), NBPF1 (p.L648V), ZFHX3

(p.Q2007*), ZFHX3 (p.H2001N), and/or ZFHX3 (p.F1800L)). In some cases, an SNV is in a gene selected from the group consisting of CR1, DPY19L2, TMPRSS13 and/or HBG1 (e.g., CR1 (p.R2194*), CR1 (p.M2208T), DPY19L2 (p.I647V), TMPRSS13 (p.A77G), TMPRSS13 (p.Q78R), and/or HBG1 (p.A137G)).

In one aspect, this disclosure provides a method of determining a prognosis of a human subject having multiple myeloma (MM). The method includes detecting CTCs present in a blood biopsy from the human subject. Detection of CTCs in the blood biopsy is indicative of disease progression and absence of CTC detection is indicative of progression-free survival. In some embodiments, the CTCs are detected using multiparameter flow cytometry. In certain instances, the CTCs are e.g., >0.001%, >0.002%, 0.003%, >0.005%, >0.006%, >0.010%, >0.015%, >0.020%, >0.05%, >0.1%, >0.2%, >0.5%, >1% relative to white blood cells in a blood biopsy.

In one aspect, this disclosure provides a method of determining treatment efficacy of a therapeutic agent in a human subject having MM. The method includes measuring a percentage of CTCs relative to white blood cells present in a first blood biopsy from the human subject obtained prior to administration of the therapeutic agent, and measuring a percentage of CTCs relative to white blood cells present in a second blood biopsy from the human subject obtained after administration of the therapeutic agent, and comparing the percentage of CTCs in the first blood biopsy to the percentage of CTCs in the second blood biopsy. A decrease in the percentage of CTCs in the second blood biopsy relative to the percentage of CTCs in the first blood biopsy indicates that the therapeutic agent is effective treatment. No change in the percentage of CTCs or an increase in the percentage of CTCs in the second blood biopsy relative to the percentage of CTCs in the first blood biopsy indicates that the therapeutic agent is ineffective. In some embodiments, the CTCs are detected using multiparameter flow cytometry.

In one aspect, this disclosure provides a method of diagnosing whether a human subject has, or is at risk of developing, MM. In one embodiment, the method includes detecting in cfDNA, DNA from a CTC, or exoDNA or RNA from the human subject at least one genetic abnormality selected from the group consisting of a translocation involving chromosome 14, a copy number variation (CNV) involving chromosome 1, a CNV involving chromosome 13, and a CNV involving chromosome 17. Detection of the at least one genetic abnormality indicates that the human subject has, or is at risk of developing, MM. In another embodiment, the method includes detecting in cfDNA, DNA from a CTC, or exoDNA from the human subject at least one genetic abnormality in a gene associated with MM. Detection of the at least one genetic abnormality indicates that the human subject has, or is at risk of developing, MM. In any embodiment, the method can include treating the human subject with a therapeutic agent for treatment of MM. In some embodiments, the detection of the genetic abnormality or abnormalities in the cfDNA is performed by a method comprising whole exome sequencing or targeted deep sequencing.

In one aspect, this disclosure provides a method of monitoring a plasma cell dyscrasia in a human subject. The method includes detecting in cfDNA, DNA from a CTC, or exoDNA at least one MM biomarker in the DNA. The detecting can be done both before and at one or more time points after the subject is administered a therapy to treat the plasma cell dyscrasia (e.g., MGUS, SMM, MM). In certain instances the detection is performed using a blood biopsy. In certain instances peripheral blood samples are taken from the subject, e.g., 1 week, 2 weeks, 3 weeks, 4 weeks, 2 months, 3 months, 4 months, 5 months, 6 months, 7 months, 8 months, 9 months, 10 months, 11 months, 1 year, 2 years, or 3 years after commencement of the therapy to treat the plasma cell dyscrasia. Detection of the at least one MM biomarker indicates progression of the plasma cell dyscrasia. In some embodiments, the detection of the MM biomarker in the cfDNA is performed by a method comprising whole exome sequencing or targeted deep sequencing.

In one aspect, this disclosure provides a method that includes detecting in cfDNA, DNA from a CTC, or exoDNA from a human subject at least one genetic abnormality in a gene associated with MM. Detection of the at least one genetic abnormality in a gene associated with MM indicates that the human subject has MM or is at risk of developing MM. Detection of the at least one genetic abnormality in a gene associated with MM indicates that the human subject is a candidate for a therapeutic agent targeted to the gene associated with MM. In some embodiments, the detection of the genetic abnormality or abnormalities in the cfDNA is performed by a method comprising whole exome sequencing or targeted deep sequencing.

In one aspect, this disclosure features a method for determining the prognosis of a human subject having, or suspected of having, a plasma cell dyscrasia (e.g., MGUS, SMM, or multiple myeloma). In certain instances, the method involves determining the expression level of RNA including a miRNA from exosomes isolated from the human subject, wherein a lower expression level of the miRNA identifies the subject as having a poorer prognosis than a subject with a higher expression level of the miRNA. In certain instances, the method involves determining that the expression level of a miRNA from exosomes isolated from the human subject is lower than the expression level of that same miRNA from a subject who is known to not have a plasma cell dyscrasia (e.g., MGUS, SMM, or multiple myeloma). The lower expression level of the miRNA is indicative of a better outcome than a higher expression level of the miRNA. In certain embodiments, the miRNA is one or more of let-7b, let-7e, miR-106a, miR-106b, miR-16, miR-17, miR-181a, miR-18a, miR-20a, miR-21, miR-25 and miR-744. In certain embodiments, the miRNA is one or more of let-7e, miR-106a, miR-106b, miR-16, miR-17, miR-18a, miR-20a, and miR-25. In other embodiments, the miRNA is one or more of let-7b, let-7e, and miR-16. In certain embodiments, the expression level of at least let-7b, let-7e, and miR-16 is assessed. In other embodiments, the expression level of at least let-7e, miR-106a, miR-106b, miR-16, miR-17, miR-18a, miR-20a, and miR-25 is determined. The expression levels of an miRNA can be determined by, e.g., quantitative RT-PCR. In some instances, the method further comprises performing the International Staging System (based on albumin and beta-2 microglobulin levels in peripheral blood at the time, or at substantially the same time as, the exosomes are isolated from the subject) and/or analysis of chromosomal abnormalities (e.g., t(4:14), 17p deletion, 1q21 amplification). In certain instances, the outcome is progression free survival. In other instances, the outcome is improved survival.

In one aspect, the disclosure relates to a method that involves isolating circulating exosomes from a human subject having or suspected of having a plasma cell dyscrasia (e.g., MGUS, SMM, multiple myeloma); extracting RNA from the exosomes; measuring the expression level of an miRNA using the RNA from the exosomes; and determining that the expression level of the miRNA is lower than the level of that miRNA in a subject not having or not suspected of having the plasma cell dyscrasia (e.g., MGUS, SMM, multiple myeloma). The lower expression level is indicative of a worse prognosis for the subject than a higher expression level. In certain embodiments, the miRNA is one or more of let-7b, let-7e, miR-106a, miR-106b, miR-16, miR-17, miR-181a, miR-18a, miR-20a, miR-21, miR-25 and miR-744. In certain embodiments, the miRNA is one or more of let-7e, miR-106a, miR-106b, miR-16, miR-17, miR-18a, miR-20a, and miR-25. In other embodiments, the miRNA is one or more of let-7b, let-7e, and miR-16. In certain embodiments, the expression level of at least let-7b, let-7e, and miR-16 is assessed. In other embodiments, the expression level of at least let-7e, miR-106a, miR-106b, miR-16, miR-17, miR-18a, miR-20a, and miR-25 is determined. In certain embodiments, the method further comprises administering a therapy for the plasma cell dyscrasia (MGUS, SMM, multiple myeloma). Such therapies are known in the art. The expression levels of an miRNA can be determined by, e.g., quantitative RT-PCR. In some instances, the method further comprises performing the International Staging System (based on albumin and beta-2 microglobulin levels in peripheral blood at the time, or at substantially the same time as, the exosomes are isolated from the subject) and/or analysis of chromosomal abnormalities (e.g., t(4:14), 17p deletion, 1q21 amplification). In certain instances, the outcome is progression free survival. In other instances, the outcome is improved survival.

In another aspect, the disclosure provides a method of determining the effectiveness of a therapy administered to a human subject with a plasma cell dyscrasia (e.g., MGUS, SMM, or MM). The method involves determining the expression level of at least one miRNA from exosomes isolated from the subject. The exosomes may be obtained from a biological sample (e.g., blood or serum sample) before and at one or more time points after commencement of the therapy. In some embodiments, the at least one miRNA is selected from the group consisting of let-7b, let-7e, miR-106a, miR-106b, miR-16, miR-17, miR-181a, miR-18a, miR-20a, miR-21, miR-25, and miR-744. In other embodiments, the at least one miRNA is selected from the group consisting of let-7e, miR-106a, miR-106b, miR-16, miR-17, miR-18a, miR-20a, and miR-25. In yet other embodiments, the at least one miRNA is selected from the group consisting of let-7b, let-7e, and miR-16. In certain embodiments, the expression level of at least let-7b, let-7e, and miR-16 is assessed. In other embodiments, the expression level of at least let-7e, miR-106a, miR-106b, miR-16, miR-17, miR-18a, miR-20a, and miR-25 is determined. Under this method, a low expression of the at least one miRNA (relative to the expression level of the miRNA/miRNAs prior to the administration of the therapy) identifies the subject as not benefitting from the therapy. A high expression of the at least one miRNA (relative to the expression level of the miRNA/miRNAs prior to the administration of the therapy) identifies the subject as benefitting from the therapy. The expression levels of an miRNA can be determined by, e.g., quantitative RT-PCR. In some instances, the method further comprises performing the International Staging System (based on albumin and beta-2 microglobulin levels in peripheral blood at the time, or at substantially the same time as, the exosomes are isolated from the subject) and/or analysis of chromosomal abnormalities (e.g., t(4:14), 17p deletion, 1q21 amplification).

In another aspect, the disclosure features a method for predicting the progression free survival in a human subject having or suspected of having a plasma cell dyscrasia (e.g., MGUS, SMM, MM). The method involves determining the expression level of at least one miRNA obtained from the exosomes of the subject. In certain embodiments, the at least one miRNA is selected from the group consisting of let-7b, let-7e, miR-106a, miR-106b, miR-16, miR-17, miR-181a, miR-18a, miR-20a, miR-21, miR-25, and miR-744. In other embodiments, the at least one miRNA is selected from the group consisting of let-7e, miR-106a, miR-106b, miR-16, miR-17, miR-18a, miR-20a, and miR-25. In yet other embodiments, the at least one miRNA is selected from the group consisting of let-7b, let-7e, and miR-16. In certain embodiments, the expression level of at least let-7b, let-7e, and miR-16 is assessed. In other embodiments, the expression level of at least let-7e, miR-106a, miR-106b, miR-16, miR-17, miR-18a, miR-20a, and miR-25 is determined. The expression level of the miRNA/miRNAs can be determined, e.g., by quantitative RT-PCR. The subject is determined to have a worse PFS if the expression level of the at least one miRNA is lower than a control level (e.g., the expression level of the at least one miRNA in a human subject not having MGUS, SMM, MM). The subject is determined to have a better PFS if the expression level of the at least one miRNA is higher than a control level (e.g., the expression level of the at least one miRNA in a human subject not having MGUS, SMM, MM).

In one aspect, the disclosure provides a blood biopsy. The biopsy involves obtaining a biological (e.g., blood) sample from a human subject being tested for a plasma cell dyscrasia (e.g., MGUS, SMM, MM). The sample can be tested using circulating free DNA (cfDNA), DNA or RNA (e.g., miRNA) from a circulating exosome, or DNA from a circulating tumor cell (CTC) for one or more gene abnormalities associated with a plasma cell dyscrasia described herein. The results from the biopsy can be used to determine appropriate treatments for the human subject.

A subject "suspected of having a plasma cell dyscrasia" is one having one or more symptoms of the plasma cell dyscrasia. As used herein, a subject "at risk of developing a hematological malignancy" is a subject that has a biomarker for the plasma cell dyscrasia regardless of whether or not the subject has one or more symptoms of the plasma cell dyscrasia.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features and advantages of the disclosure will be apparent from the following detailed description and figures, and from the claims.

BRIEF DESCRIPTION OF THE DRAWINGS

FIG. 8 is a chart showing unique SNVs identified in BM. Unique SNVs were identified by comparing BM and CTC samples from each patient.

DETAILED DESCRIPTION

Figure 1A:
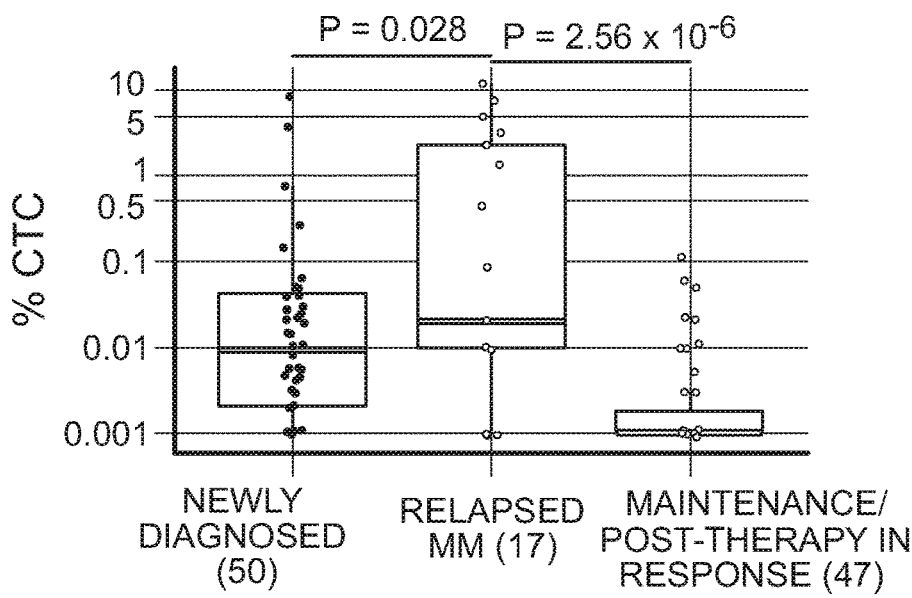
FIG. 1 is a series of graphical depictions of data showing the prognostic value of circulating tumor cell (CTC) monitoring in multiple myeloma (MM). (a) is a boxplot showing the distributions of CTC at different stages of MM, as indicted. Wilcoxon rank-sum test was used to compare the distribution of CTC between two groups. (b) is a scatter-plot showing the correlation between CTC and M-spike in MM. linear regression p-value and adjusted R-squared are shown. (c) is a line graph showing the clinical impact of CTC detection in newly diagnosed MM patients. Patients were classified into two groups based on presence of CTC (>0.001%). A log-rank test was used to estimate the statistical significance of differences observed between curves. (d) is histogram showing the distribution of CTC trend in a sequential cohort. CTC trend was modeled using linear regression and denoted by the resulting slope. Given the skewed distribution of slopes, the median absolute deviation (MAD) was calculated to represent a robust measure of the variability. A cutoff was defined as Median+MAD=0.048; slopes that were greater than this cutoff were defined as CTC UP group. (e) is a line graph showing the clinical impact of CTC trend in MM patients. Patients were classified as described in (d), and differences between survival curves were tested by log-rank test.

This disclosure describes a novel method and biomarkers to identify progression and clonal evolution of plasma cell dyscrasias.

More specifically, the present disclosure provides materials and methods for the diagnosis, prognosis, staging, and monitoring of plasma cell dyscrasias based on the presence of the biomarkers in a blood biopsy. This disclosure also provides methods for monitoring the progression of a plasma cell dyscrasia, determining the efficacy of a therapeutic agent, and/or determining a targeted therapy related to a plasma cell dyscrasia. This disclosure also provides methods for treating a human subject having, or at risk of developing, a plasma cell dyscrasia based on the presence of the biomarkers in a blood biopsy.

Plasma Cell Dyscrasias

Plasma cell dyscrasias are disorders of plasma cells that generally arise as a result of abnormal proliferation of a monoclonal population of plasma cells that may or may not secrete detectable levels of a monoclonal immunoglobulin or immunoglobulin fragment (paraprotein or M protein). Plasma cell dyscrasias include, for example, multiple myeloma, solitary plasmacytoma of bone, extramedullary plasmacytoma, Waldenstrom's macroglobulinemia (WM), primary amyloidosis, light chain deposition disease, paraproteinemia, and heavy-chain disease.

In some embodiments, the plasma cell dyscrasia is multiple myeloma (also known as plasma cell myeloma, myelomatosis, or Kahler's disease). MM is a cancer of plasma cells, a type of white blood cell normally responsible for producing antibodies. In MM, collections of abnormal plasma cells accumulate in the bone marrow, where they interfere with the production of normal blood cells.

As used herein, unless otherwise indicated, multiple myeloma (MM) refers to any stage of MM. Recent studies have shown that MM is consistently preceded by a precursor state such as monoclonal gammopathy of undetermined significance (MGUS) or smoldering multiple myeloma (SMM) (Landgren et al., 2009 Blood 113:5412-5417; Weiss et al., 2009 Blood 113:5418-5422). Thus, stages of MM include MGUS and SMM, as well as symptomatic MM and plasma cell leukemia (PCL; the most aggressive plasma cell disorder). MGUS is characterized by blood M protein <30 g/L, bone marrow plasma cells <10%, and no myeloma-related organ or tissue impairment. MGUS is observed for progression, but is typically not treated. SMM is characterized by blood M protein >30 g/L, Bone marrow plasma cells >10%, and myeloma-related organ or tissue impairment. SMM is typically observed and treated. MM is characterized by M protein in blood and/or urine, and the presence of plasma cells >10% in bone marrow or in any quantity in other tissues (plasmacytoma). MM is typically treated immediately. PCL can evolve from an existing case of multiple myeloma as part of the terminal phase of the disease and characterized by plasma cells accounting for more than 20% of cells in the peripheral blood with an absolute plasma cell count of more than $2 \times 10^9$/L. Treatments for MM include, for example, a proteasome inhibitor (e.g., Velcade® (bortezomib) or Kyprolis™ (carfilzomib)), an oral agent (e.g., Thalomid® (thalidomide) or Revlimid® (lenalidomide)), a chemotherapy agent (e.g., Doxil® (doxorubicin)), steroids (e.g., corticosteroids, dexamethasone, or prednisone), bisphosphonates (for individuals with osteolytic lesions, osteoporosis, or osteopenia), and any combination thereof. In addition, any treatment may be used alone or in combination with other therapies.

Some patients rapidly progress from SMM to overt MM (progressors) with a rate of progression of 70% over 5 years, while others remain indolent with minimal progression (non-progressors) over the same time period (Landgren, 2013 Hematology: ASH Education Book 1:478-487). Biological factors that distinguish progressors and non-progressors in MGUS/SMM are not well known (Ghobrial et al, 2014 Blood 124:3380-8). The current prognostic factors used to assess progression are based on tumor burden markers including the level of monoclonal spike, free light chains, and/or percent of plasma cells in the bone marrow.

Given that MM is always preceded by a well-defined precursor state, and given the ease of access to primary patient samples (peripheral blood and bone marrow samples), MM can represent one of the best models of cancer to determine biomarkers of tumor progression in early premalignant conditions. This disclosure provides molecular biomarkers of MM biomarkers useful for diagnosis, prognosis, and/or staging of plasma cell dyscrasias that will significantly impact the clinical care of patients having, or at risk of developing, a plasma cell dyscrasia.

Liquid Biopsies

The development of non-invasive liquid biopsies opens new opportunities for prognosis and monitoring of clonal heterogeneity of plasma cell dyscrasias. Bodily fluids for which non-invasive collection methods are available include, without limitation, blood, lymph, cerebrospinal fluid, breast milk, urine, saliva, and sputum. In some cases the liquid biopsy is a blood biopsy. A "blood biopsy" is a sample of peripheral blood which can be used to detect biomarkers that are usually observed in the bone marrow biopsies. A blood biopsy provides a number of advantages over a bone marrow (BM) biopsy.

A BM biopsy is a painful procedure for patients. As a result, only a single BM biopsy is typically obtained from a patient, and many patients with precursor state plasma cell dyscrasias (e.g., MGUS or SMM) do not have BM biopsies performed at all. A blood biopsy is a non-invasive method with minimal patient discomfort and the ability to obtain multiple sequential biopsies.

A blood biopsy can significantly change our understanding of clonal evolution in MM. Disease complexity can be determined through serial samples of peripheral blood during disease progression and clonal evolution. A BM biopsy is limited in sampling only a single BM site. MM is characterized by patchy BM infiltration and genomic complexity which was recently corroborated by massive parallel-sequencing studies displaying an average of 35 amino acid changing point mutations per sample and the lack of a universal driving mutation (Lohr et al., 2014 Cancer Cell 25:91-101; Bolli et al., 2014 Nature Communications 5:2997; Chapman et al., 2011 Nature 471:467-472). BM biopsies at a single site in the BM vary significantly from clones located in distant BM sites; thus, a BM biopsy may not be reflective of the total disease heterogeneity. A blood biopsy allows a sample of multiple, and potentially all, clones present in the bone marrow instead of sampling only one site of the bone marrow thus providing a more complete profile of MM clonal diversity. In addition, multiple sequential blood biopsies can easily be obtained enabling one to monitor changes in the mutational profile over time.

Biomarkers

Biomarkers described herein are detectable using a blood biopsy. A biological marker, or "biomarker," as used herein refers to a measurable genetic abnormality that is an indicator of some biological state or condition. Provided herein are biomarkers useful for diagnosis, prognosis, staging, monitoring, and/or personalization or therapy related to plasma cell dyscrasias. Biomarkers useful for the diagnosis, prognosis, staging, monitoring, and/or personalization or therapy related to MM are also referred to as MM biomarkers. Biomarkers are detectable in a blood biopsy from a subject having, or at risk of developing, a plasma cell dyscrasia, but are not detectable in a healthy (e.g., not having a plasma cell dyscrasia) subject.

In some cases a biomarker is a circulating tumor cell (CTC). Comprehensive analyses of cancer genomes promise to inform prognoses and precise patient-specific treatments. Unlike other hematological malignancies (e.g., leukemia), in MM there is not a substantial CTC burden, except in late stages of disease progression such as in plasma cell leukemia. This application provides a sensitive method (e.g., multiparameter flow cytometry) to detect CTCs in blood biopsies from MM patients at different disease stages. An association exists between detectable CTCs and progression-free survival (see, e.g., Example 1). For example, detectable CTCs (e.g., >0.001% CTCs relative to white blood cells present in a blood biopsy) and a trend of increasing CTC counts over multiple blood biopsies (e.g., at least 3 serial samples from a subject) were both associated with poor overall survival.

In some cases a biomarker is a genetic abnormality. As used herein a genetic abnormality is any mutation to a gene associated with a plasma cell dyscrasia or associated with susceptibility to a plasma cell dyscrasia. For example, a MM biomarker can be a genetic abnormality in any gene associated with MM or associated with susceptibility to MM. Many types of genetic abnormalities are known in the art and may include mutations to a chromosome and/or mutations to the genetic sequence. Genetic abnormalities are shown herein using standard mutation nomenclature (den Dunnen and Antonarakis, 2000 Human Mutation 15:7-12). For example, the nomenclature of t(A;B) indicates a translocation which joins chromosomes shown in the parentheses. For example, a p. indicates a substitution in the protein with the wild type amino acid appearing before the residue number and the mutated amino acid following the residue number. An asterisk (*) in place of the second amino acid indicates a stop codon has been introduced.

Many types of chromosomal abnormalities are known in the art and may include a structural abnormality (e.g., translocations, inversions, or insertions) or an atypical number of chromosomes (e.g., copy number variations such as deletions or duplications). In some embodiments, a chromosomal abnormality is a translocation. Exemplary translocations associated with plasma cell dyscrasias are shown in Table 1. In some cases, the translocation is selected from the group consisting of t(4;14), t(6;14), t(11;14), t(14;16), and t(14;20). In some embodiments, a chromosomal anomaly MM biomarker is a copy number variation (CNV). Exemplary CNVs are shown in, for example, Table 6. In some cases, the CNV is a 1q21 amplification, a 1p32 deletion, a 13q deletion, a 16q deletion, or a 17p deletion.

Many types of genetic abnormalities are known in the art and may include one or more (e.g., 2, 3, 4, 5, 6, 7, 8, 9, 10, 12 15, 20, 25, 30, 35, 40, 50, 75, 100 or more) single nucleotide variations (SNVs; e.g., single nucleotide deletions, additions, or substitutions), copy number variations (CNVs; e.g., insertions or deletions), or frameshift mutations. The genetic abnormalities can also be multiple (e.g., 2, 3, 4, 5, 6, 7, 8, 9, 10, 12 15, 20, 25, 30, 35, 40, 50, 75, 100, 150, 200, 400, 600, 800, 1,000, 1500, 2,000, 4,000, 5,000, 10,000 or more) contiguous or non-contiguous nucleotide deletions, additions, or substitutions. In some cases, a genetic abnormality may be in a gene associated with a plasma cell dyscrasia. Mutations in genes can be synonymous or silent mutations (i.e., having no effect on the function of the gene product) or mutations can be non-synonymous (i.e., preventing the gene from functioning properly and/or altering the function of the gene product). Abnormalities described herein can be non-synonymous mutations. In some cases, a genetic abnormality is non-synonymous single nucleotide variations (NS-SNVs).

In some cases a biomarker is a genetic abnormality in a gene associated with cancer or associated with susceptibility to cancer (e.g., a gene whose mutation contributes to general cancer formation and/or progression). Genes associated with general susceptibility to multiple forms of cancer are referred to as pan-cancer driver genes. For example, a genetic abnormality detectable in a blood biopsy from a subject having, or at risk of developing, a plasma cell dyscrasia can be in one or more of the following pan-cancer driver genes: FAT1, BCLAF1, CDC27, HLA-B, NBPF1, and ZFHX3. In some cases a genetic abnormality is one or more of FAT1 (p.V3464I or p.K2895R), BCLAF1 (p.N629S), CDC27 (p.A273G), HLA-B (p.K210N), NBPF1 (p.D679E, p.K41R, or p.L648V), and ZFHX3 (p.Q2007*, p.H2001N, or p.F1800L).

In some cases a biomarker is a genetic abnormality in a gene associated with MM or associated with susceptibility to MM (e.g., a gene whose mutation contributes specifically to MM formation and/or progression). Genes associated with susceptibility to MM are referred to as MM driver genes. For example, genetic abnormalities detectable in a blood biopsy from a subject having, or at risk of developing, a plasma cell dyscrasia can be in one or more of the following MM driver genes: KRAS, NRAS, TP53, DIS3, FAM46C, BRAF, TRAF3, PRDM1, CYLD, RB1, ACTG1, IRF4, IDH1, INTS12, SP140, LTB, MAX, HIST1H1E, EGR1, FGFR3, FNDC3A, TNKS, BCL7A, RPL10, GCET2, RASA2, PLA2G2D, C9orf80, HIST1H3G, CDKN1B, RNF151, C17orf77, FAM153B, SLC24A1, OR1L8, USP50, CXCR4, KRTDAP, FBXO36, ROBO1, TGDS, SNX7, MPEG1, DHX32, RYR2, NFKBIA, FSIP2, SI, NECAB3, COASY, EIF4G2, ZFHX4, CCND1, LRRC16A, YTHDF2, PHOX2B, C15orf59, MOGAT3, EXOG GRIA2, C4orf43, CCDC144NL, CKM, OR1N2, PRIM2, OR1S2, NDUFAF3, C20orf112, HIST1H3H, and PNRC1. In some cases a genetic abnormality is one or more of KRAS (p.G12D), KRAS (p.Q61H), NRAS (p.G12D), BRAF (p.G469R), IRF4 (p.L116R), SLC24A1 (p.R686G), MPEG1 (p.G537E), and RYR2 (p.I784V).

In some cases a biomarker is a genetic abnormality common to both a blood biopsy and a matched BM biopsy from a subject. Example 1 shows whole exome sequencing of CTCs and matched BM clonal PCs to demonstrate that 79% of mutations present in CTCs are concordant with those in BM clonal PCs (see, e.g., FIGS. 5a and 5b). The mutational profile present in a blood biopsy can indicate disease progression. For example, detection of a mutational profile that is common to both a blood biopsy and a matched BM biopsy would indicate minimal or absent clonal evolution and/or minimal change or no change in clonal heterogeneity. Mutational profiles common to blood and BM could contain a single genetic abnormality or a plurality (e.g., two, three, four, five, six, seven, eight, nine, 10, 12, 15, 20, 25, 30, 40, 50, 70, 100, 150, 200, 300, or 500) of genetic abnormalities. For example, a mutational profile indicative of minimal or absent clonal evolution and/or minimal change or no change in clonal heterogeneity can include a genetic abnormality in one or more of the following genes: KRAS, NRAS, BRAF, IRF4, MPEG1, RYR2, SLC24A1, FAT1, BCLAF1, CDC27, HLA-B, NBPF1, and ZFHX3. In some cases a genetic abnormality is one or more of KRAS (p.G12D), KRAS (p.Q61H), NRAS (p.G12D), BRAF (p.G469R), IRF4 (p.L116R), MPEG1 (p.G537E), RYR2 (p.I784V), SLC24A1 (p.R686G), FAT1 (p.V3464I or p.K2895R), BCLAF1 (p.N629S), CDC27 (p.A273G), HLA-B (p.K210N), NBPF1 (p.D679E, p.K41R, or p.L648V), or ZFHX3 (p.Q2007*, p.H2001N, or p.F1800L).

In some embodiments a genetic abnormality is unique to a blood biopsy relative to a matched BM sample from a subject. Again, the mutational profile present in a blood biopsy can indicate disease progression. For example, detection of a mutational profile that is unique to a blood biopsy relative to a matched BM biopsy would indicate clonal evolution and/or increased clonal heterogeneity. In this case, "unique" can be "overlapping" or "not overlapping." Thus, for example, a unique blood biopsy from a test subject could have a mutational profile in which some mutations are the same as those detected in BM from the same test subject and others are different. Alternatively, a unique blood biopsy from a test subject could have a mutational profile in which no mutations are the same as those detected in BM. For example, a mutational profile indicative of clonal evolution and/or increased clonal heterogeneity can include a genetic abnormality in one or more of the following genes: CR1, DPY19L2, TMPRSS13, HBG1, FAM178B, OR6P1, TNRC6B, PRDM2, HERC3, PIK3R4, PATZ1, ARHGEF33, ELAVL4, RP11-766F14.2, RBM14, CELF4, FAM104B, SPAG17, HELZ2, DNAH7, SLC25A23, ZNF98, VGLL1, RRBP1, MUC4, RRN3, MUC2, KRTAP9-2, GPR64, TPSD1, TAL1, PSMB8, ANPEP, and CCDC108. In some cases a genetic abnormality is one or more of CR1 (p.R2194* or p.M2208T), DPY19L2 (p.I647V), TMPRSS13 (p.A77G or p.Q78R), HBG1 (p.A137G), FAM178B (p.D35H), OR6P1 (p.A264S), TNRC6B (p.L383S or T403A), PRDM2 (p.E428*), HERC3 (p.Y864*), PIK3R4 (p.K1136N), PATZ1 (p.P459S), ARHGEF33 (p.D863E), ELAVL4 (frame shift), RP11-766F14.2 (p.R537C), RBM14 (p.Q151P), CELF4 (p.N21S), FAM104B (p.R107*), SPAG17 (p.P388T), HELZ2 (p.R1190L), DNAH7 (p.I3394L), SLC25A23 (p.S417F), ZNF98 (p.Y87C), VGLL1 (p.G35V), RRBP1 (p.G449D), MUC4 (p.S1653I or p.H3026P), RRN3 (p.P11S or p.R9C), MUC2 (p.T1582R), KRTAP9-2 (p.A41S), GPR64 (p.T359A), TPSD1 (p.A92T), TAL1 (p,L280I), PSMB8 (p.Y93H), ANPEP (p.V726A), and CCDC108 (p.V738D). For example, new SNVs uniquely identified in CTCs include 6 NS-SNVs in 4 genes (CR1, DPY19L2, TMPRSS13 and HBG1) that were detected from multiple patient samples (see, e.g., Example 1). In some cases a NS-SNV is CR1 (p.R2194* or p.M2208T), DPY19L2 (p.I647V), TMPRSS13 (p.A77G or p.Q78R), or HBG1 (p.A137G).

Genetic abnormalities also include any epigenetic modification which affects a genetic sequence that causes MM or is associate with susceptibility to MM. Epigenetic modifications regulated gene expression and/or protein function without changing the DNA sequence. Epigenetic modifications are well known and can include, for example, modifications to either DNA (e.g. cytosine methylation and hydroxymethylation) or proteins (e.g. lysine acetylation, lysine and arginine methylation, serine and threonine phosphorylation, and lysine ubiquitination and sumoylation). Epigenetic modifications can be applied to any biomarker described herein.

This disclosure also provides a panel including a plurality of biomarkers described herein (see, e.g., Example 2). In some embodiments the panel includes about 80 genes recurrently mutated in MM and known as oncogenes/tumor suppressor genes, such as NRAS, KRAS, BRAF and TP53 that occur in about 75% of MM patients. In addition, the panel can include CNVs and translocations involving IGH that occur in about 60% of patients; namely t(4;14), t(6;14), t(11;14), t(14;16), t(14;20). Additional CNVs that are known to confer an adverse prognosis in MM include 1q21 amp, del13q and del17p.

In some cases a biomarker is a RNA obtained from exosomes from a human subject. In some instances, the RNA is miRNA. In certain embodiments, the miRNA is one or more of let-7b, let-7e, miR-106a, miR-106b, miR-16, miR-17, miR-181a, miR-18a, miR-20a, miR-21, miR-25 and miR-744. In certain embodiments, the miRNA is one or more of let-7e, miR-106a, miR-106b, miR-16, miR-17, miR-18a, miR-20a, and miR-25. In other embodiments, the miRNA is one or more of let-7b, let-7e, and miR-16. In certain embodiments, the expression level of at least: let-7 and miR-16 is assessed. In certain embodiments, the expression level of at least: let-7b, let-7e, and miR-16 is assessed. In other embodiments, the expression level of at least: let-7e, miR-106a, miR-106b, miR-16, miR-17, miR-18a, miR-20a, and miR-25 is determined. The expression levels of an RNA or miRNA can be determined by, e.g., quantitative RT-PCR. In some instances, the RNA (e.g., miRNA) biomarker analysis is done alongside the International Staging System (based on albumin and beta-2 microglobulin levels in peripheral blood at the time, or at substantially the same time as, the exosomes are isolated from the subject) and/or analysis of chromosomal abnormalities (e.g., t(4:14), 17p deletion, 1q21 amplification).

Detecting/Measuring a Biomarker

Detection of one or more biomarkers in a blood biopsy may represent a non-invasive method to evaluate plasma cell dyscrasias. For example, detection of one or more biomarkers is useful for diagnosis, prognosis, staging, monitoring, and/or personalization or therapy related to plasma cell dyscrasias.

Determining the presence of one or more biomarkers may include analysis of all or part of a genome or may include analysis of all or part of an exome. Determining the presence of one or more biomarkers may include analysis of one or more (e.g., 2, 3, 4, 5, 6, 7, 8, 9, 10, 12, 15, 20, 25, 30, 35, 40, 50, 75, 100, 150, 200, 300, 400, 500, 1,000, 2,000, 3,000, 4,000, 5,000, or 10,000 or more) genes of interest.

In embodiments where the biomarker is a CTC, the CTC can be detected by any manner known in the art. The presence of CTCs can be detected, for example, using flow cytometry (e.g., multiparameter flow cytometry). An exemplary flow cytometry method for detecting CTCs in blood biopsies is described in Example 1. Briefly, CTCs were identified on the basis of intermediate/strong CD38 expression, strong CD138 expression, down-regulation of CD19, and down-regulation of CD45, with or without over-expression of CD56 or CD28.

In embodiments where the biomarker is a genetic abnormality, the biomarker can be detected by any manner known in the art. The presence of a translocation can be detected by, for example, cytogenetic analyses such as karyotyping and analysis of G-banded chromosomes (e.g., via fluorescent in situ hybridization (FISH) or comparative genomic hybridization (CGH)). The presence of a CNV can be detected by, for example, software programs such as Samtools v0.1.18, VarScan v2.3.7, and/or DNAcopy (Seshan and Olshen 2010; bioconductor.org/) See, for example, the methods described in Example 1. The presence of a NS-SNV can be detected by, for example, by standard sequence techniques and/or by software programs such as MuTect (Cibulskis et al., 2013 *Nature Biotechnology* 31:213-219) See, for example, the methods described in Example 1.

The genetic abnormality can be detected in any genetic material derived from the plasma cell dyscrasia found in the blood biopsy. For example, a blood biopsy of a person having a plasma cell dyscrasia can include, for example, circulating free DNA (cfDNA), a circulating exosome, or a circulating tumor cell (CTC) which originated from the plasma cell dyscrasia. In some cases, the genetic material may need to be isolated from a circulating exosome or from a CTC. Methods of isolating genetic material are well known. In some cases, isolation of the genetic material may include treating the starting material (e.g., a blood biopsy) to lyse red blood cells followed by the removal of proteins and other contaminants and finally recovery of the DNA (see, e.g., Example 1). In some cases genetic material is amplified prior to analysis. Methods of amplification are well known and may include whole genome amplification as described in Example 1.

In some cases, the genetic material is circulating free DNA (cfDNA) released by tumor cells (e.g., MM cells) into the bloodstream. Recent studies indicate that cfDNA may be more accurate in the assessment of clonal heterogeneity in solid tumors compared to CTCs (Murtaza et al., 2013 *Nature* 497:108-112), since cfDNA may reflect a broader representation of the different clones present in multiple sites of the bone marrow. Thus, one or more biomarkers can be detected in cfDNA (see, e.g., Example 2).

In some cases, the genetic material is derived from extracellular vesicles (EVs). EVs can carry cargo such as mitochondrial DNA (mtDNA), single-stranded DNA, double-stranded DNA (dsDNA) and/or mRNA. Tumor EVs have been shown to carry oncogene amplifications (i.e., c-Myc) have been detected in EVs (Lazaro-Ibanez et al., 2014 *The Prostate* 74:1379-1390) and DNA that reflects the genetic status of the tumor (Kahlert et al., 2014 *The Journal of Biological Chemistry* 289:3869-3875). EVs include, without limitation, exosomes, ectosomes, and, apoptotic bodies. In some cases the EV is an exosome. In some cases, the genetic material is isolated from an EV. Thus, one or more biomarkers can be detected in DNA isolated from a circulating exosome (see, e.g., Example 3).

In some cases the genetic material is derived from a CTC. Whole exome sequencing of CTCs and matched BM clonal PCs demonstrated that 79% of mutations present in CTCs are concordant with those in BM clonal PCs. In some cases, the genetic material is isolated from a CTC. Thus, one or more biomarkers can be detected in DNA from a CTC (see, e.g., Example 1).

In some cases, the genetic material is RNA (e.g., miRNA) derived from exosomes of the human subject. The expression levels of an RNA or miRNA can be determined by any method known in the art, e.g., quantitative RT-PCR.

Methods of Use

Provided herein are methods for using the biomarkers described herein. The methods described herein are useful in determining whether a human subject has, or is at risk of developing, a plasma cell dyscrasia. The methods described herein may be applied to any appropriate subject having, or at risk of developing, a plasma cell dyscrasia. Non-limiting examples of a subject having, or at risk of developing, a plasma cell dyscrasia include humans, non-human primates, horses, bovine species, porcine species, dogs, cats, rabbits, rats, and mice. In some embodiments, a subject having, or at risk of developing, a plasma cell dyscrasia is a human. For example, the methods described herein can be applied to a human subject having, or at risk of developing, MM.

In some embodiments, the method comprises detecting/measuring a biomarker. The mutational profile present in a blood biopsy can indicate a number of things. For example, the presence of a biomarker as provided herein can be used to determine a diagnosis, prognosis, or stage of a plasma cell dyscrasia based on the presence of the biomarkers in a blood biopsy. The presence of a biomarker as provided herein can be used to monitor a plasma cell dyscrasia for disease progression, to determine the efficacy of a therapeutic agent, and/or to determine an appropriate targeted therapy for the plasma cell dyscrasia.

This application provides methods for diagnosing plasma cell dyscrasia based on detection of at least one biomarker in a blood biopsy from a human subject. In some cases, a genetic abnormality is a useful biomarker for diagnosing a plasma cell dyscrasia (e.g., MM). A method can include detecting at least one genetic abnormality associated with a plasma cell dyscrasia in cfDNA, DNA from a circulation exosome, or DNA from a CTC from a human subject. For example, detection of at least one genetic abnormality in a gene associated with MM indicates that the human subject has MM. A method of determining whether a human subject has, or is at risk of developing, a plasma cell dyscrasia (e.g., MM) can include detecting at least one genetic abnormality described herein in cfDNA, DNA from a CTC, or DNA from a circulating exosome from the human subject. Detection of the at least one genetic abnormality indicates that the human subject has, or is at risk of developing, MM. In some cases, detecting at least one translocation in a gene associated with MM (e.g., t(4;14), t(6;14), t(11;14), t(14;16), or t(14;20)) indicates that the human subject has, or is at risk of developing, MM. In some cases, detecting at least one copy number variation in a gene associated with MM (e.g., 1q21 amplification, 1p32 deletion, 13q deletion, 16q deletion, or 17p deletion) indicates that the human subject has, or is at risk of developing, MM. In some cases, detecting at least one SNV in a gene associated with MM (e.g., KRAS (p.G12D), KRAS (p.Q61H), NRAS (p.G12D), BRAF (p.G469R), IRF4 (p.L116R), MPEG1 (p.G537E), RYR2 (p.I784V), SLC24A1 (p.R686G), FAT1 (p.V3464I or p.K2895R), BCLAF1 (p.N629S), CDC27 (p.A273G), HLA-B (p.K210N), NBPF1 (p.D679E, p.K41R, or p.L648V), or ZFHX3 (p.Q2007*, p.H2001N, or p.F1800L)) indicates that the human subject has a clonal MM which has not progressed. In some cases detecting at least one SNV in a gene associated with MM (e.g., CR1 (p.R2194* or p.M2208T), DPY19L2 (p.I647V), TMPRSS13 (p.A77G or p.Q78R), or HBG1 (p.A137G)) indicates that the human subject has MM which has undergone clonal evolution and/or has increased clonal heterogeneity. The method can also include treating the human subject with a therapeutic agent.

This document provides methods for determining a prognosis of a plasma cell dyscrasia based on detection of at least one biomarker in a blood biopsy from a human subject. In some cases, a CTC is a useful biomarker for determining a prognosis for a human subject having MM. A method of determining a prognosis of a human subject having MM can include detecting CTCs present in a blood biopsy from the human subject. For example, detection of CTCs (i.e., >0.001% CTCs relative to white blood cells present in a blood biopsy) in the blood biopsy indicates a poor prognosis (e.g., disease progression), and absence of CTC detection in the blood biopsy indicates a better prognosis (e.g., better progression-free survival); see, e.g., Example 1 and FIG. 1c. A trend of increasing CTC counts also indicates poor overall survival (see, e.g., Example 1 and FIG. 1e). A higher percentage of CTC in the peripheral blood is associated with poor prognosis and survival. In some cases, a genetic abnormality is a useful biomarker for determining a prognosis for a human subject having or at risk of developing MM. A method can include detecting at least one genetic abnormality associated with a plasma cell dyscrasia in cfDNA, DNA from a circulating exosome, or DNA from a CTC from a human subject. For example, detection of at least one genetic abnormality in a gene associated with MM indicates that the human subject is at risk of developing MM. A method of determining whether a human subject is at risk of developing a plasma cell dyscrasia can include determining whether cfDNA, DNA from a circulating exosome, or DNA from a CTC from a blood biopsy from the subject has one or more gene abnormalities described herein.

This document provides methods for staging a plasma cell dyscrasia based on detection of at least one biomarker in a blood biopsy from a human subject. In some cases, a CTC is a useful biomarker for determining a stage of MM in a human subject. A method of staging MM in a human subject can include measuring a percentage of CTCs relative to white blood cells present in a blood biopsy from the human subject. For example, a low percentage of CTCs is associated with a precursor state such as monoclonal gammopathy of undetermined significance (MGUS) or smoldering multiple myeloma (SMM) while an increased percentage of CTCs is associated with symptomatic MM or PCL.

This document provides methods for monitoring the progression of a plasma cell dyscrasia based on detection of at least one biomarker in a blood biopsy from a human subject. A method of monitoring a plasma cell dyscrasia in a human subject can include detecting at least one genetic abnormality in cfDNA, DNA from a CTC, or DNA from a circulating exosome. Detection of the at least one genetic abnormality indicates progression of the plasma cell dyscrasia. For example, detecting at least one SNV in a gene associated with MM (e.g., KRAS (p.G12D), KRAS (p.Q61H), NRAS (p.G12D), BRAF (p.G469R), IRF4 (p.L116R), MPEG1 (p.G537E), RYR2 (p.I784V), SLC24A1 (p.R686G), FAT1 (p.V3464I or p.K2895R), BCLAF1 (p.N629S), CDC27 (p.A273G), HLA-B (p.K210N), NBPF1 (p.D679E, p.K41R, or p.L648V), or ZFHX3 (p.Q2007*, p.H2001N, or p.F1800L)) which is also detected in a matched BM biopsy indicates that the human subject has a clonal MM which has not progressed. For example, detecting at least one SNV in a gene associated with MM (e.g., CR1 (p.R2194* or p.M2208T), DPY19L2 (p.I647V), TMPRSS13 (p.A77G or p.Q78R), or HBG1 (p.A137G)) in a blood biopsy which cannot be detected in a matched BM biopsy indicates that the human subject has MM which has undergone clonal evolution and/or has increased clonal heterogeneity.

This document provides methods for determining the efficacy of a therapeutic agent based on detection of at least one biomarker in a blood biopsy from a human subject. In some cases, a CTCs is a useful biomarker for determining the efficacy of a therapeutic agent. A method of determining treatment efficacy of a therapeutic agent in a human subject having MM can include measuring a percentage of CTCs relative to white blood cells present in a first blood biopsy from the human subject obtained prior to administration of the therapeutic agent, measuring a percentage of CTCs relative to white blood cells present in a second blood biopsy from the human subject obtained after administration of the therapeutic agent, and comparing the percentage of CTCs in the first blood biopsy to the percentage of CTCs in the second blood biopsy. A decrease in the percentage of CTCs in the second blood biopsy relative to the percentage of CTCs in the first blood biopsy is indicative that the therapeutic agent is effective treatment. No change in the percentage of CTCs or an increase in the percentage of CTCs in the second blood biopsy relative to the percentage of CTCs in the first blood biopsy is indicative that the therapeutic agent is ineffective.

This document provides methods for treating a human subject having, or at risk of developing, a plasma cell dyscrasia based on the presence of the biomarkers in a blood biopsy. Methods for treating a human subject include a targeted therapy (also referred to as personalized medicine) based on a particular biomarker detected in a blood biopsy from the human subject. In some cases, a genetic abnormality is a useful biomarker for determining a targeted therapy. A targeted therapy can be designed to target a gene product (e.g., a protein) expressed by the genetic abnormality. For example, a BRAF inhibitor can be used to treat a human subject identified as having a genetic abnormality in the BRAF gene. A method can include detecting at least one genetic abnormality described herein in cfDNA, DNA from a CTC, or DNA/RNA from a circulating exosome from a human subject. Detection of at least one genetic abnormality in a gene associated with MM indicates that the human subject is a candidate for a therapeutic agent targeted to a gene produce of the gene associated with MM. A targeted therapy can also be designed to target a gene product (e.g., a protein) expressed by a gene associated with the genetic abnormality. As used herein, a gene product associated with the genetic abnormality is a protein in the same gene regulatory network or the same signal transduction pathway as the gene product expressed by the genetic abnormality. For example, a plasma cell dyscrasia having a genetic abnormality can respond to a therapy that targets a first gene product of the genetic abnormality (e.g., BRAF), but may also respond to a therapy that targets a second gene product of another gene in the same signal transduction pathway (e.g., KRAS, NRAS, MEK, and/or MPAK).

The treatment methods described above for any of the plasma cell dyscrasias can also include additional and/or alternative treatment (e.g., chemotherapy, radiation therapy, targeted therapy, immunotherapy, and stem cell transplants) either before, substantially at the same time as, or after the indicated treatment. Non-limiting examples of chemotherapeutic agents commonly used for MM include, for example, a proteasome inhibitor (e.g., Velcade® (bortezomib) or Kyprolis™ (carfilzomib)), an oral agent (e.g., Thalomid® (thalidomide) or Revlimid® (lenalidomide)), a chemotherapy agent (e.g., Doxil® (doxorubicin)), steroids (e.g., corticosteroids, dexamethasone, or prednisone), and bisphosphonates (e.g., pamidronate or zoledronic acid for individuals with osteolytic lesions, osteoporosis, or osteopenia). Non-limiting examples of additional chemotherapeutic agents include, but are not limited to, an alkylating agent (e.g., busulfan, chlorambucil, cisplatin, cyclophosphamide (cytoxan), dacarbazine, ifosfamide, mechlorethamine (mustargen), and melphalan), a topoisomerase inhibitor, an antimetabolite (e.g., 5-fluorouracil (5-FU), cytarabine (Ara-C), fludarabine, gemcitabine, and methotrexate), an anthracycline, an antitumor antibiotic (e.g., bleomycin, dactinomycin, daunorubicin, doxorubicin (Adriamycin), and idarubicin), an epipodophyllotoxin, nitrosoureas (e.g., carmustine and lomustine), topotecan, irinotecan, doxorubicin, etoposide, mitoxantrone, bleomycin, busultan, mitomycin C, cisplatin, carboplatin, oxaliplatin and docetaxel. Non-limiting examples of immunotherapies commonly used for MM include interferon and immunoglobulin. Non-limiting examples of stem cell transplants commonly used for MM include transplantation of autologous (the subject's own) or allogeneic (from a donor) hematopoietic stem cells derived from, for example, bone marrow, peripheral blood, or umbilical cord blood. The methods described above for any of the plasma cell dyscrasias can include a single additional and/or alternative treatment or any combination of additional and/or alternative treatments.

The invention will be further described in the following examples, which do not limit the scope of the invention described in the claims.

EXAMPLES

Example 1. Mutational Profile and Prognostic Relevance of Circulating Tumor Cells in Multiple Myeloma Circulating tumor cells (CTCs) have prognostic relevance in patients with MM and their mutational profile mirrors the genomic variants present within the bone marrow malignant plasma cells; thereby defining a new role for CTCs in the prognostic and molecular profiling of MM patients.

Introduction

Recent studies of massive parallel sequencing of tumor cells obtained from the bone marrow (BM) of patients with multiple myeloma (MM) have demonstrated significant clonal heterogeneity in MM with a median of five clones present in each sample (Lohr et al., 2014 Cancer Cell 25:91-101; Bolli et al., 2014 Nature Communications 5:2997; Cone et al., 2015 Blood 125:1870-1876). The most frequently observed mutations were seen in KRAS, NRAS, DIS3, TP53, FAM46C and BRAF (Lohr et al., 2014 Cancer Cell 25:91-101; Bolli et al., 2014 Nature Communications 5:2997; Cone et al., 2015 Blood 125:1870-1876). Driver mutations in the same pathways were demonstrated to be mutually exclusive in individual cells (Leiserson et al., 2013 PLoS Computational Biology 9:e1003054), but multiple mutations within the same pathway (e.g., KRAS, NRAS, and BRAF) have been observed in different subclones from the same patients (Lohr et al., 2014 Cancer Cell 25:91-101).

Results

Detection Rate and Prognostic Relevance of CTC in MM Patients.

Figure 1B:
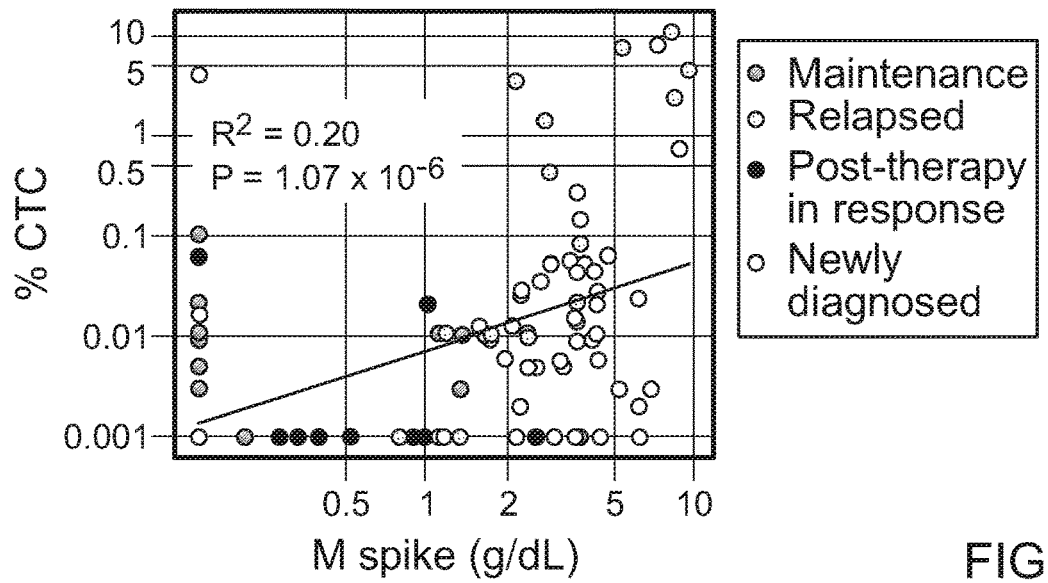
Figure 1C:
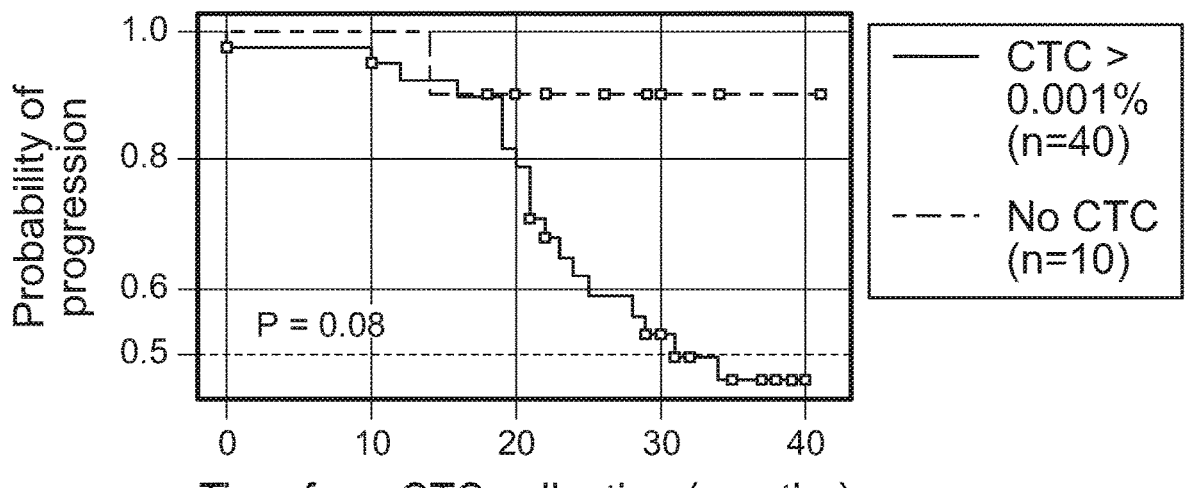

Before investigating if CTCs could represent a reliable non-invasive alternative to perform genomic characterization of MM patients, their applicability for prognosis at different disease stages of MM was first defined. Using sensitive multiparameter flow cytometry (MFC), we showed that CTCs were detectable in 40/50 (80%) newly-diagnosed MM patients, 27 out of 64 samples (42.2%) relapsed non sequential samples and 44 out of 66 samples (66.7%) in the sequential samples collected. Significant differences were observed between newly diagnosed patients (median of 0.017%; range, 0.001%-8%) and relapsed MM (Median of 0.003%, range, 0-72%, p=0.028) and between relapsed MM and patients in response post therapy or on maintenance therapy (p=$2.56 \times 10^{-6}$) patients, (FIG. 1a and Table 2). For MM patients, we further examined the correlation between monoclonal protein measurements of tumor burden (M-spike) at the time of sample acquisition and determination of the percentage of CTCs. As shown in FIG. 1b, there was a weak correlation between M spike value and level of CTCs in the PB ($R^2$=0.20, p=$1.07 \times 10^{-6}$). Accordingly, the screening for CTCs is applicable to all patients with MM independent of the level of M spike.

TABLE 1

Patient characteristics*

| Patient ID | Age at the time of sample collection in 2014 | % BM involvement | % CTCs | Number of CTCs (cells/μL) | Total CTCs harvested | DNA extracted (ng) | Cytogenetics/FISH** |
|---|---|---|---|---|---|---|---|
| 413 | 51 | 33 | 0.24 | 25 | 86,000 | 160 | +1q |
| 431 | 50 | 18 | 0.32 | 13.4 | 48,800 | 157 | None |
| 434 | 50 | 36 | 0.08 | 5.9 | 26,300 | 232 | t(4; 14) |
| 447 | 59 | 46 | 0.06 | 3 | 5,200 | 176 | +1q/del(1p)/del(IgH) |
| 448 | 58 | 77 | 0.05 | 3.4 | 15,000 | 294 | del(17p) |
| 453 | 64 | 70 | 2 | 107 | 300,000 | 1,022 | +1q |
| 457 | 58 | 95 | 0.04 | 1.68 | 11,400 | 279 | del(1p32) |
| 461 | 52 | 11 | 0.51 | 13.8 | 37,100 | 259 | t(4; 14)/+1q |

*All samples collected from March to May 2014
**Cytogenetics and FISH are examined for the following markers: 1p/1q and t(4; 14) and t(14/16) and del(17p)

We then focused on 50 newly diagnosed transplant-ineligible patients prospectively enrolled on the PETHEMA/GEM2010MAS65 clinical trial to address the role of sensitive baseline monitoring of CTCs. With a median follow-up of approximately 3 years, 19 of the 40 cases displaying PB CTCs had relapsed (median time-to progression of 31 months); by contrast, only 1 of the 10 patients with undetectable CTCs has relapsed (median time-to progression not reached; log-rank P-value=0.081, FIG. 1C).

After demonstrating an association between detectable CTCs and progression-free survival, we further investigated whether dynamic changes in the kinetics of CTCs in sequential PB samples was also predictive of outcome. We examined 66 sequential clinical samples obtained from 28 patients who were seen at the Dana-Farber Cancer Institute (DFCI) in the years 2011-2012 (Table 3).

TABLE 2

Patient characteristics of samples analyzed with one time point of CTCs (non-sequential cases) at DFCI.

| Characteristic | Non sequential (n = 64) |
|---|---|
| Sex | |
| Male | 30 (46.9%) |
| Female | 34 (53.1%) |
| Median age (range) | 59.5 (35-75) |
| Diagnosis | |
| MM | 64 (100%) |
| Subcategory (MM) | |
| Relapsed | 17 (56.6%) |
| On Maintenance | 28 (43.8%) |
| Post-therapy in response | 19 (29.7%) |
| Treatment | |
| No | 34 (53.1%) |
| Maintenance therapy | 30 (46.9%) |
| Follow-up | |
| Median duration of follow-up (range), days | 1050 (27-1145) |
| Death during follow-up | 17 (26.6%) |

TABLE 3

Patient characteristics of sequential samples analyzed at DFCI.

| Characteristic | Sequential (n = 28) |
|---|---|
| Sex | |
| Male | 16 (57.1%) |
| Female | 12 (42.9%) |
| Median age (range) | 63.5 (40-87) |
| Diagnosis (at first CTC analysis) | |
| SMM | 3 (11.0%) |
| MM | 25 (87.7%) |
| Subcategory (MM) | |
| Relapsed | 18 (72.0%) |
| Maintenance | 4 (16.0%) |
| Post-therapy in response | 3 (12.0%) |
| Treatment at the time of CTC sample | |
| Yes | 16 (57.1%) |
| No | 8 (28.6%) |
| Maintenance therapy | 4 (14.3%) |

TABLE 3-continued

Patient characteristics of sequential samples analyzed at DFCI.

| Characteristic | Sequential (n = 28) |
|---|---|
| Follow-up | |
| Median duration of follow-up (range), days | 795 (20-1118) |
| Death during follow-up | 15 (53.6%) |
| Laboratory data | |
| Median serum M protein (range), g/dL | 1.86 (0-9.56) |
| Median B2M (range), g/dL | 3.15 (1.40-22.3) |
| CTC monitoring | |
| Total number of samples | 66 |
| Median duration between sequential samples (range), days | 43 (13-105) |
| Number of CTC analysis/patient | Median = 2 |
| n = 2 | 21 |
| n = 3 | 5 |
| n = 4 | 1 |

Figure 1D:
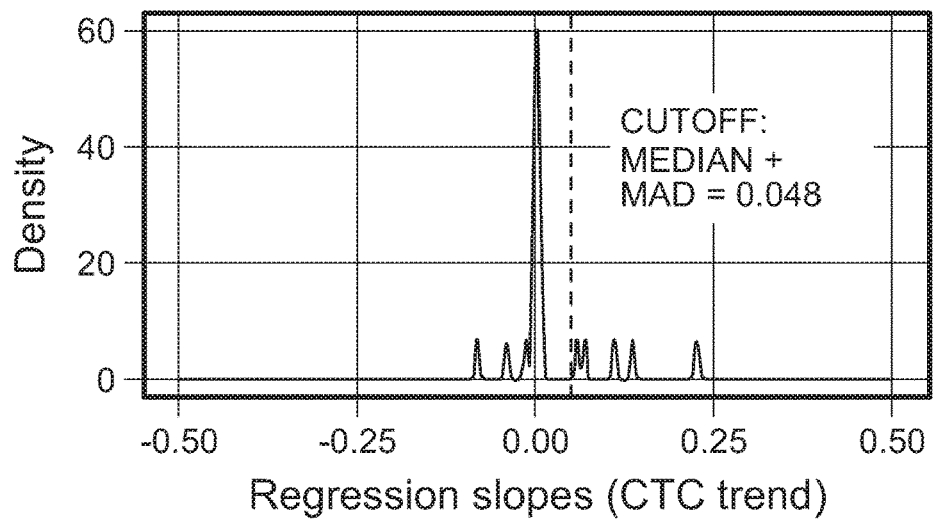
Figure 1E:
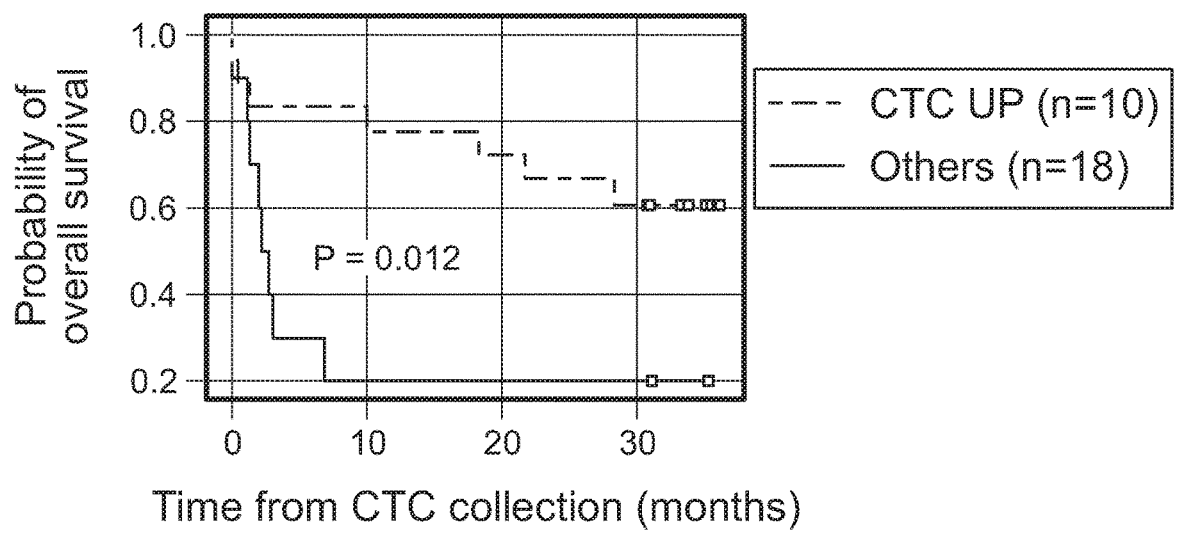

There was a median of 3 samples per patient (range, 2-5) and we determined the CTC trend for each patient using linear regression. Given the slopes were not normally distributed, we adopted median absolute deviation (MAD) as a robust measure of the variability. Then a cutoff was defined as (Median+MAD), and samples with slopes greater than this cutoff were classified as the "CTC UP" group (n=10); this group was then compared to samples, in which such trend was not observed (n=18), (FIG. 1d). As shown in FIG. 1e, increasing CTC counts were associated with poor overall survival (p-value=0.012), indicating that both the absolute numbers of CTCs and trend of CTC are predictive of outcome in MM.

Mutational Profile of CTCs in Patients with MM.

Figure 2:
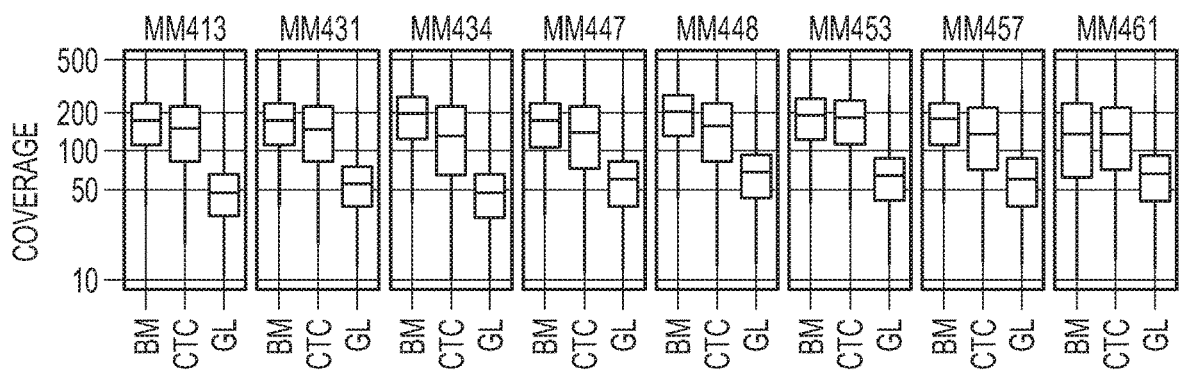
FIG. 2 is a boxplot showing the coverage distribution of targeted regions. The DepthOfCoverage function from Genome Analysis Toolkit (GATK) was used to calculate the mean coverage of each targeted region. The distribution of mean coverage in each sample is represented by boxplot. Bone marrow (BM), CTC and germline (GL) from the same patient were plotted. Reads of two WGA libraries from the sample were merged.

After demonstrating that CTCs can be readily detected in the majority of MM patients, we then determined the mutational profile of CTCs and compared it to that of patient-paired BM clonal PCs by analyzing 8 MM patients with matched flow-sorted BM and PB tumor cells and germline non-tumor cell DNA from PB T-lymphocytes. All patients had newly-diagnosed, untreated MM diagnosed in 2014, and their characteristics are shown in Table 1. Purified BM and PB clonal PCs were obtained by flow-sorting as described in the methods section. The experiment was designed to sequence the whole exome of BM clonal PCs and CTCs up to 200×, and germline cells up to 50×. For samples with minimal numbers of CTCs (N=8), whole genome amplification (WGA) was performed and two independent libraries were constructed from the sample, followed by sequencing up to 100× for each duplicate. The mean coverage in the samples exceeded the designed target, as shown in Table 4 and FIG. 2.

TABLE 4

Overall quality control of sequenced samples using BamUtil tool.

| Sample | TotalRead (M) | MappingRate (%) | ProperPair (%) | DupRat (%) | Mean Coverage |
|---|---|---|---|---|---|
| MM413_BM | 160.33 | 97.37 | 95.1 | 22.6 | 287.28 |
| MM413_CTC_A | 77.34 | 92.77 | 89.1 | 29.25 | 113.06 |
| MM413_CTC_B | 84.34 | 93.47 | 90.2 | 24.17 | 134.8 |
| MM413_GL | 35.38 | 97.78 | 95.86 | 6.9 | 77.2 |
| MM431_BM | 163.62 | 97.83 | 95.96 | 22.03 | 299.42 |
| MM431_CTC_A | 78.41 | 93.3 | 89.54 | 25.26 | 122.38 |
| MM431_CTC_B | 89.98 | 92.94 | 89.01 | 34.05 | 122.72 |

TABLE 4-continued

Overall quality control of sequenced samples using BamUtil tool.

| Sample | TotalRead (M) | MappingRate (%) | ProperPair (%) | DupRat (%) | Mean Coverage |
|---|---|---|---|---|---|
| MM431_GL | 39.98 | 98.81 | 97.46 | 8.33 | 88.22 |
| MM434_BM | 205.37 | 96.35 | 93.42 | 32.66 | 311.2 |
| MM434_CTC_A | 93.96 | 94.07 | 90.32 | 33.84 | 132.04 |
| MM434_CTC_B | 86.18 | 94.17 | 90.72 | 35.01 | 119.62 |
| MM434_GL | 33.44 | 96.47 | 93.6 | 9.22 | 68.54 |
| MM447_BM | 165.87 | 96.91 | 94.29 | 28.87 | 269.22 |
| MM447_CTC_A | 86.46 | 93.23 | 89.17 | 31.25 | 123.54 |
| MM447_CTC_B | 84.97 | 93.55 | 89.72 | 34.92 | 116.04 |
| MM447_GL | 43.86 | 96.76 | 94.05 | 11.71 | 88.1 |
| MM448_BM | 214.93 | 96.45 | 93.72 | 32.65 | 327.14 |
| MM448_CTC_A | 87.04 | 92.65 | 88.42 | 30.19 | 124.44 |
| MM448_CTC_B | 88.29 | 87.52 | 81.04 | 31.74 | 106.88 |
| MM448_GL | 51.06 | 95.67 | 92.28 | 12.97 | 98.06 |
| MM453_BM | 186.92 | 96.51 | 93.64 | 31.41 | 289.66 |
| MM453_CTC | 180.93 | 96.58 | 93.72 | 31.6 | 280.06 |
| MM453_GL | 47.36 | 95.29 | 91.46 | 14.16 | 88.58 |
| MM457_BM | 166.17 | 99 | 98.31 | 30.51 | 280.86 |
| MM457_CTC_A | 79.55 | 92.86 | 88.61 | 31.18 | 112.6 |
| MM457_CTC_B | 85.1 | 92.53 | 88.06 | 33.61 | 115.08 |
| MM457_GL | 46.67 | 96.96 | 94.44 | 12.07 | 93.94 |
| MM461_BM_A | 95.87 | 91.03 | 86.05 | 34.63 | 122.74 |
| MM461_BM_B | 94.02 | 90.72 | 85.62 | 34.1 | 120.32 |
| MM461_CTC_A | 85.01 | 90.49 | 84.95 | 35.5 | 105.38 |
| MM461_CTC_B | 85.71 | 91.68 | 86.8 | 32.65 | 114.84 |
| MM461_GL | 50.21 | 94.97 | 91 | 14.39 | 92.88 |

The total number of reads (TotalReads), mapping rate (MappingRate), percentage of proper pairs (ProperPair), duplication rate (DupRate) and mean coverage are shown.
A and B in the sample names represent two parallel WGA libraries.
GL = germline.

Figure 3A:
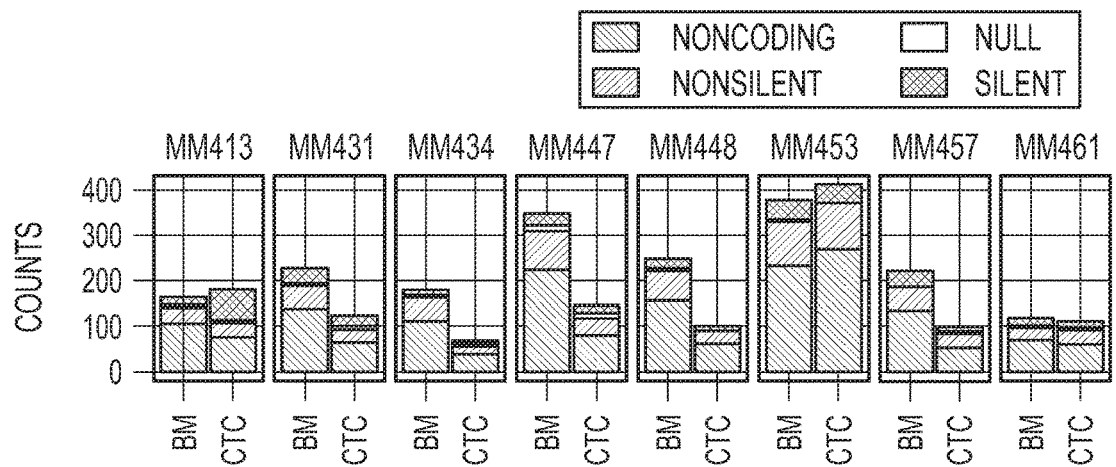
FIG. 3 is a series of graphical depictions of data showing sequencing metrics of the study on matched BM clonal plasma cells (PCs) and CTCs from 8 newly diagnosed MM patients. (a) is a stacked bar chart showing the breakdown of single nucleotide variations (SNVs). The numbers of SNVs identified in patient-paired BM clonal PCs and CTCs were 223 (interquartile ranges (IQR), 169-320) and 118 (IQR, 100-171), respectively. (b) is a stacked bar chart showing the percentage contribution of each mutation. The percentages of each type in BM myeloma PCs and CTCs were similar in all but one patient (MM413). (c) is a stacked bar chart showing the breakdown of SNVs by nucleotide change. (d) is a stacked bar chart showing the percentage contribution of each group of nucleotide change. (e) is a series of histograms showing the distributions of allele fraction of all SNVs. (f) is a series of scatter plots showing the linear regression of allele fraction of shared SNVs. Regression line and slope are shown for each patient.
Figure 3B:
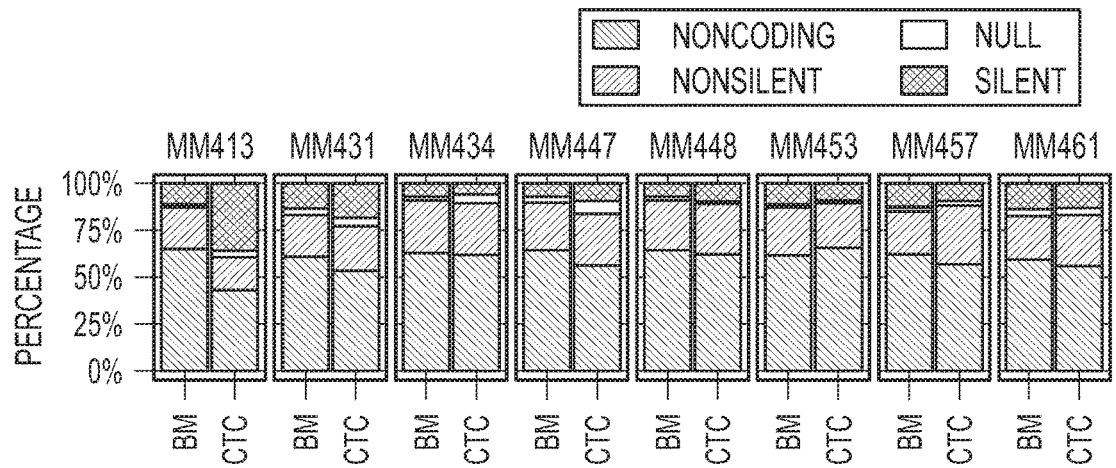
Figure 3C:
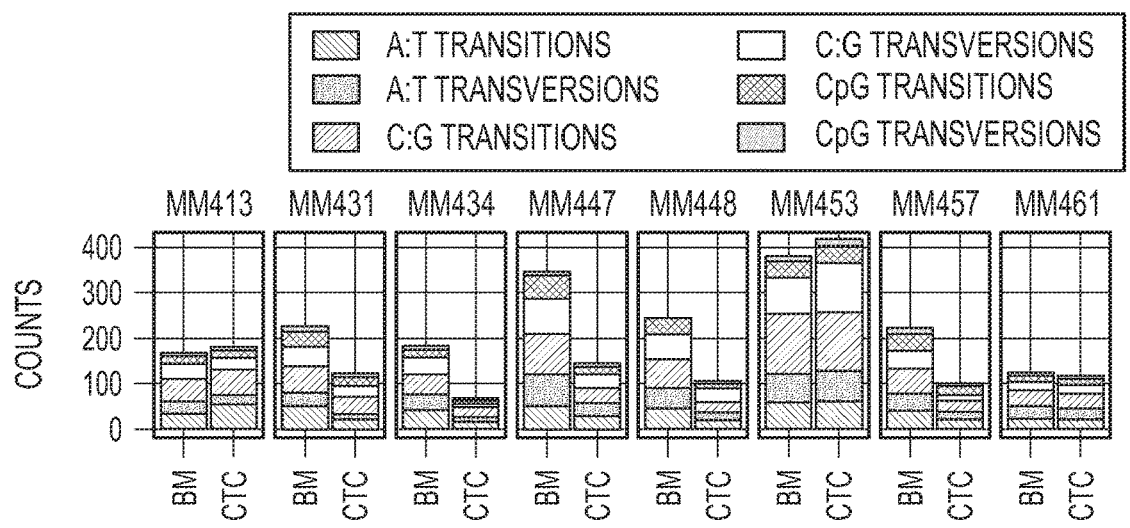
Figure 3D:
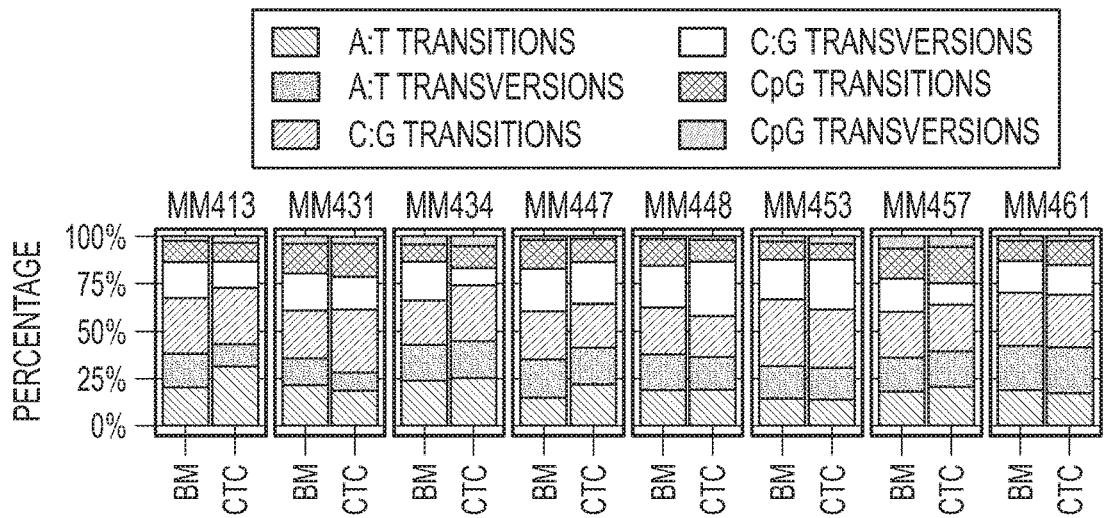

Single nucleotide variants (SNVs) were called by MuTect (Cibulskis et al., 2013 Nature Biotechnology 31:213-219) with default parameters, with an additional filter that requires at least 3 high quality reads supporting alternative variants. For samples with WGA, only SNVs shared in both parallel libraries were used. We identified a median of 223 and 118 SNVs in patient-paired BM clonal PCs and CTCs, respectively (FIG. 3a). Thus more variants were identified in BM samples, but this was not unexpected since we only retained variants shared between the two WGA libraries in the CTC samples, which increased specificity but reduced sensitivity. When we analyzed the mutational variants by type, we found that the percentages of each type in BM myeloma PCs and CTCs were similar in all but one patient (MM413), FIG. 3b. Similar findings were observed when breakdown of variants by nucleotide change was examined (FIG. 3c-d).

Figure 3E:
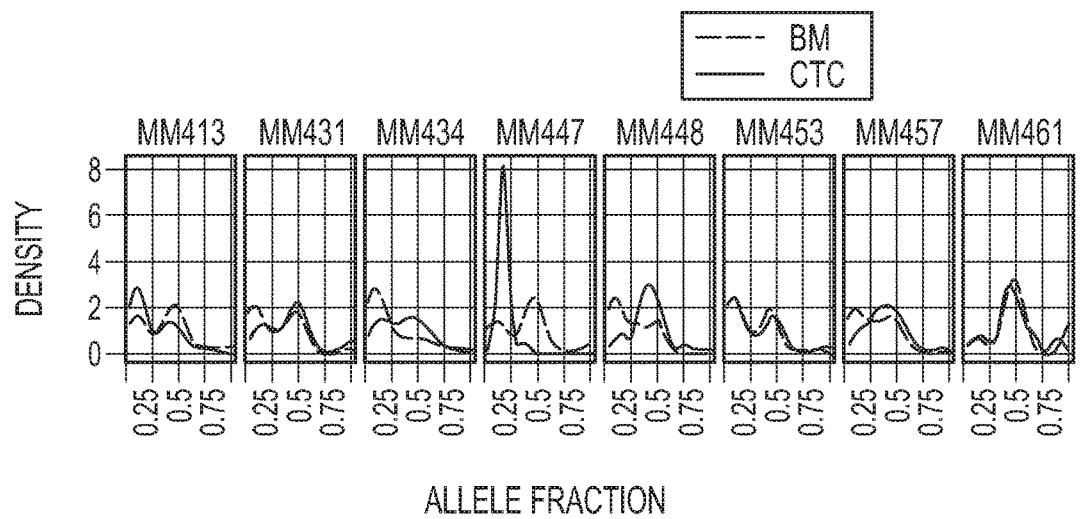
Figure 3F:
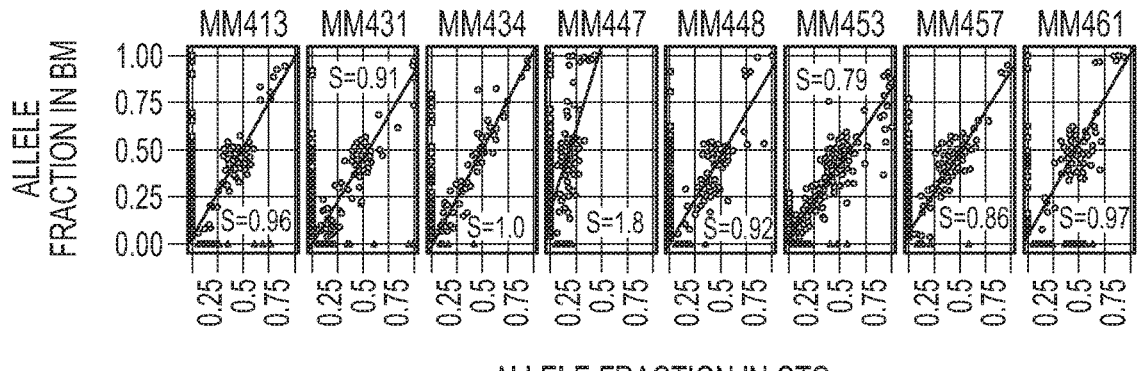
Figure 4:
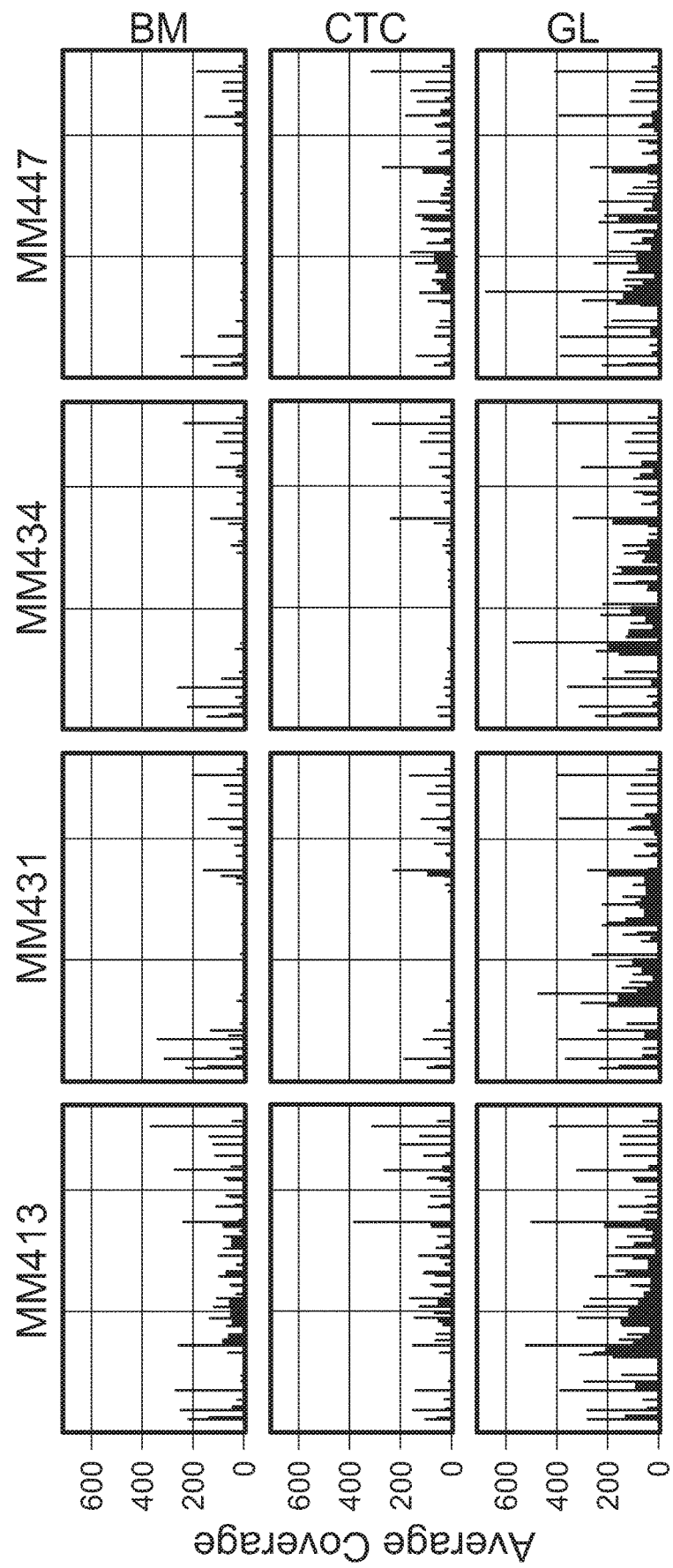
FIG. 4 is a series of histograms showing coverage patterns in the immunoglobulin heavy (IGH) region of MM patients. Each plasma cell clone has a unique rearrangement in the IGH locus (chr14:106032614-107288051) and therefore the coverage pattern in the IGH region facilitates the determination of whether BM and CTC samples have similar cell populations. Effective coverage was calculated by GATK. BM, CTC and GL from the same patient were plotted in descending order.
Figure 4:
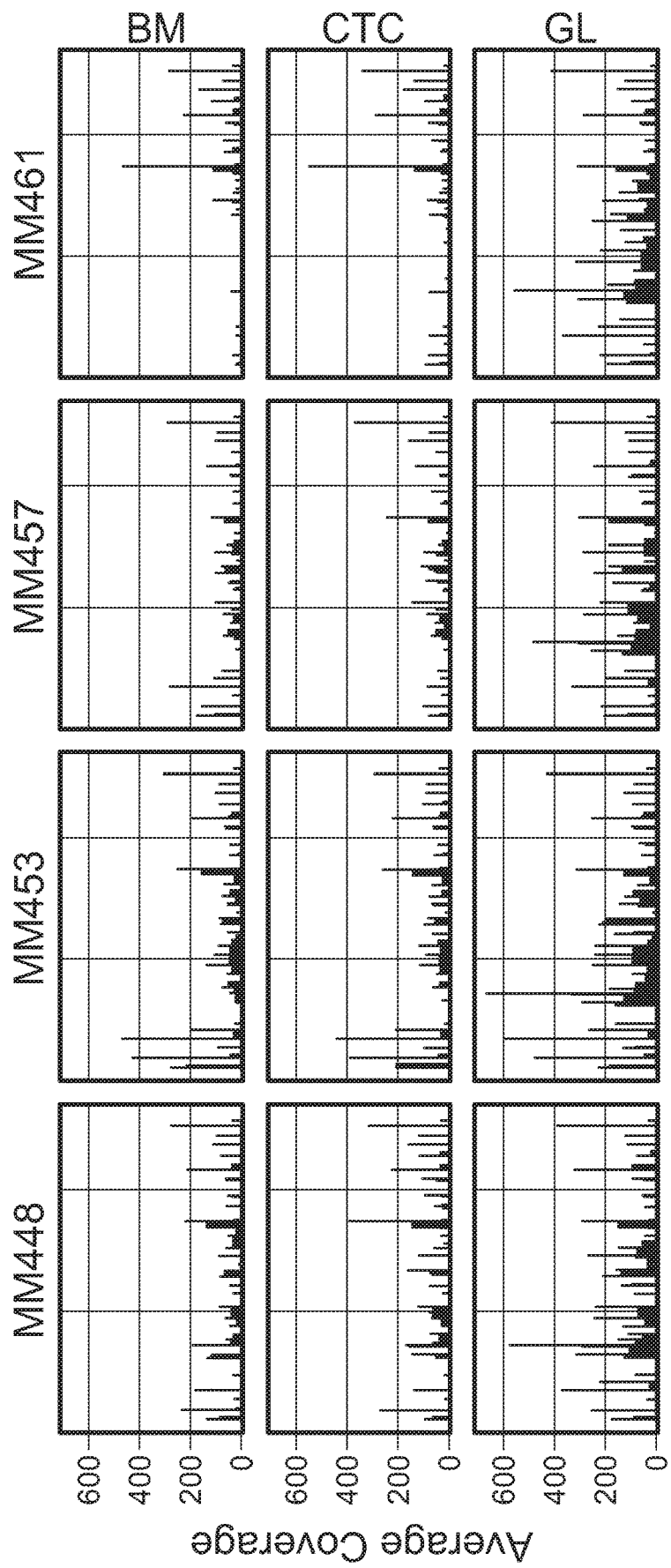

We then compared the distribution of allele fraction (AF), which is indicative of clonal heterogeneity, and demonstrated similar bimodal patterns in both BM and PB tumor cells (FIG. 3e). We further compared shared SNVs between BM myeloma clonal PCs and CTCs (FIG. 3f). As shown by regression lines and slope values, there was a statistically significant linear correlation (p-value $<2 \times 10^{-14}$ for all patients); all slopes were close to 1 except for sample MM447, in which the AF was 1.8-fold higher in the BM compared to that in CTC sample. We hypothesized that sample MM447 was contaminated with non-malignant cells and therefore examined the coverage patterns of BM and PB tumor cells in IGHV regions. Interestingly, MM447 was the only sample that demonstrated different patterns in matched BM clonal PCs and CTC (FIG. 4), indicating that sequencing of the IGHV region could be used to determine contamination with non-malignant cells when mutational profiles are being assessed in minimal numbers of CTCs.

Concordance of Somatic Variants Found in Matched BM Clonal PCs and CTCs.

Figure 5A:
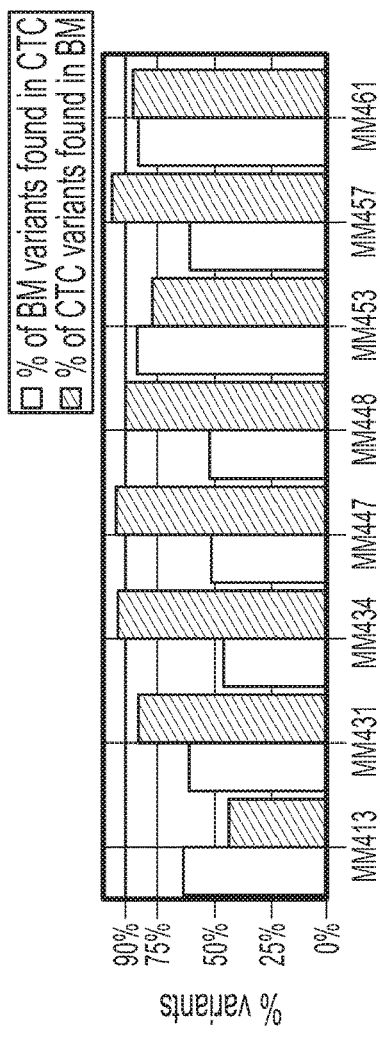
FIG. 5 shows concordance of somatic variants found in matched BM clonal PCs and CTCs. (a) is a bar graph showing percentages of shared SNVs. (b) is a Venn diagram showing numbers of shared and unique SNVs between BM clonal PCs and CTCs across all patients in this study. (c) is a series of dot plots showing instances of SNVs that occurred in curated MM driver genes, potential MM driver genes, and pan cancer genes. The full list can be found in Table 5. For each mutation, observed allele fraction was plotted with circle and a 95% confidence interval was calculated, represented as bars. Mutations from matched BM clonal PCs and CTCs were linked by solid lines. Three SNVs only found in one of the WGA libraries were also included and marked by asterisks. (d) is a series of histograms showing CNVs identified in case MM453 BM and CTC.
Figure 5B:
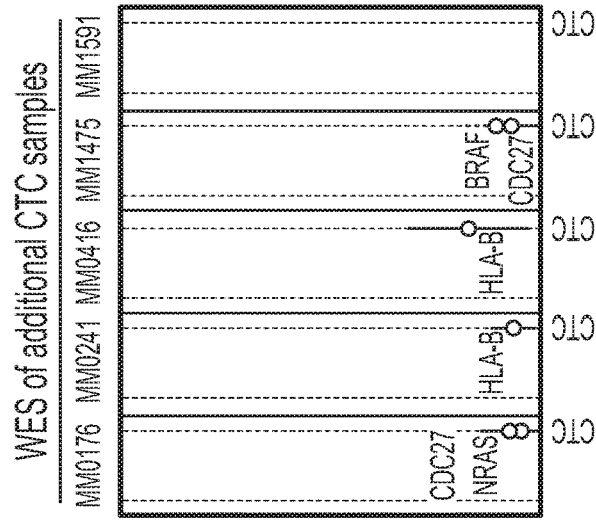

We further compared the number of SNVs shared between BM clonal PCs and CTCs and found that 79% of CTC-SNVs were also identified in the BM counterpart (FIGS. 5a-b). We then investigated specific mutations implicated in MM and curated from public databases (Omberg et al., 2013 Nature Genetics 45:1121-1126; Cancer Genome Atlas Research et al., 2013 Nature Genetics 45:1113-1120) (Methods and Table 5).

TABLE 5

Curated MM and pan cancer driver genes.

| Group | Genes |
|---|---|
| MM drivers | KRAS NRAS TPS3 D1S3 FAM46C BRAF TRAF3 PRDM1 CYLD RB1 ACTG1 IRF4 IDH1 INTS12 |
| Potential MM drivers | SP140 LTB MAX HIST1H1E EGR1 FGFR3 FNDC3A TNKS BCL7A RPL10 GCET2 RASA2 PLA2G2D C9orf80 HIST1H3G CDKN1B RNF151 C17orf77 FAM153B SLC24A1 OR1L8 USP50 CXCR4 KRTDAP FBXO36 ROBO1 TGDS SNX7 MPEG1 DHX32 RYR2 NFKB1A FSIP2 SI NECAB3 COASY EIF4G2 ZFHX4 CCND1 LRRC16A YTHDF2 PHOX28 C15orf59 MOGAT3 EXOG GRIA2 C4orf43 CCDC144NL CKM OR1N2 PRIM2 OR1S2 NDUFAF3 C20orf112 HIST1H3H PNRC1 |

TABLE 5-continued

Curated MM and pan cancer driver genes.

| Group | Genes |
|---|---|
| Pan cancer drivers | ACO1 ACVR1B ACVR2B ADNP AJUBA AKT1 ALK ALKBH6 ALPK2 ANK3 APC APOL2 ARHGAP35 ARID1A ARID2 ARID5B ASXL1 ASXL2 ATM ATP5B AXINZ AZGP1 B2M BAP1 BCLAF1 BCOR BHMT2 BRCA1 BRE C3orf70 CAP2 CARD11 CASPB CBFB CCDC120 CCDC6 CCD1D CD70 CD79B CDC27 CDH1 CDK12 CDK4 CDKN1A CDKN2A CEBPA CEP76 CHD4 CHD8 CNBD1 CNKSR1 COL5A1 COL5A3 CREBBP CTCF CTNNB1 CUL4B CUX1 DDX3X DDX5 DIAPH1 DNAH12 DNER DNMT3A EGFR EF2S2 ELF3 EP300 EPHA2 ERBB2 ERBB3 ERCC2 EZH1 EZH2 EZR FAM166A FAT1 FBXW7 FGFBF1 FGFR2 FLG FLT3 FOXA1 FOXQ1 FRMD7 GATA3 GNA13 GNB1 GNPTAB GOT1 GPS2 GUSB HIST1H3B HIST1H4E HLA-A HLA-B HRAS HSP90AB1 IDH1 IDH2 IL7R ING1 INPPL1 INTS12 IPO7 IRF6 ITGB7 ITPKB KDM5C KDM6A KEAP1 KEL KIT KLHL8 LCTL MAP2K1 MAP2K4 MAP3K1 MAP4K3 MBD1 MED12 MED23 MET MGA MICALCL MLL MLL2 MLL3 MLL4 MORC4 MPO MTOR MUC17 MXRAS MYB MYCN MYD88 MYOCD NBPF1 NCOR1 NF1 NFE2L2 NOTCH1 NPM1 NSD1 NTN4 NUP210L ODAM OMA1 OR4A16 OR52N1 OTUD7A PAPDS PBRM1 PCBP1 PDAP1 PDCD2L PDSS2 PHF6 PIK3CA PIK3R1 PLCG2 POLE POU2AF1 POU2P2 PPM1D PPP2R1A PPP6C PTEN PTPN11 QK1 RAB40A RAC1 RAD21 RASA1 RBM10 RHEB RHOA RIT1 RPL5 RPS15 RPS2 RSBN1L RUNX1 RXRA SACS SELP SEPT12 SERPINB13 SETD2 SETDB1 SF381 SFRS2 SGK1 SIRT4 SLC1A3 SLC2GA3 SLC44A3 SLC4A5 SMAD2 SMAD4 SMARCA4 SMARCB1 SMC1A SMC3 SNX25 SOS1 SOX17 SPEN SPOP STAG2 STK11 STK19 STX2 TAP1 TBC1D12 TBL1XR1 TBX3 TCEB1 TCF7L2 TCP11L2 TDRD10 TET2 TGFBR2 TIMM17A TNF TNFRSF14 TP53BP1 TPX2 TRIM23 TSC1 TTLL9 TXNDCB U2AP1 VHL WASF3 WT1 XIRP2 XPO1 ZFHX3 ZNF180 ZNF471 ZNF483 ZNF620 ZNF750 ZRANB3 |

Figure 5C:
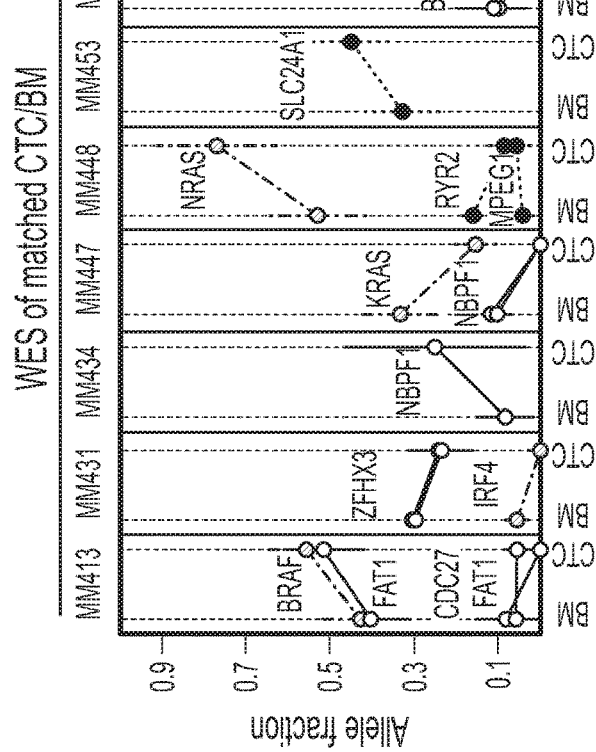
Figure 6:
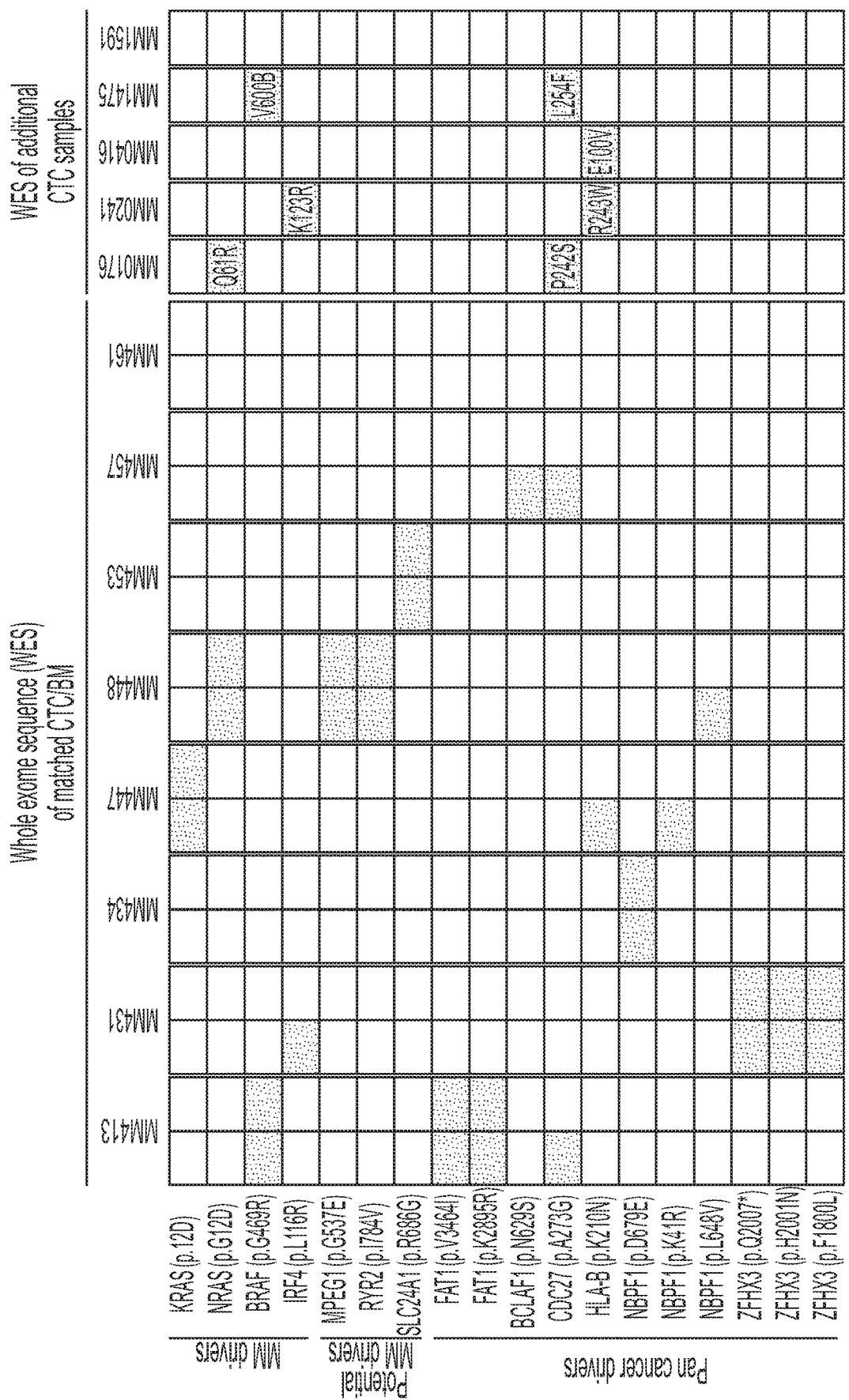
FIG. 6 is a chart showing mutations in MM or Pan cancer driver genes. MM driver genes, including potential driver genes, and pan cancer driver genes were curated as described in the methods section. Three mutations (highlighted with white borders) were identified in only one of the WGA libraries. We also examined mutations in an additional 5 CTC samples. Mutations were found in the same genes but at different locations, as indicated by changes defined in the far right boxes. Patient MM413 had 2 different SNVs in FAT1.

Among 70 MM-related genes and 246 pan-cancer driver genes (Omberg et al., 2013 *Nature Genetics* 45:1121-1126; Cancer Genome Atlas Research et al., 2013 *Nature Genetics* 45:1113-1120), a total of 18 non-synonymous single nucleotide variants (NS-SNVs) in 13 genes were identified in our cohort (FIG. 5c). Most of these NS-SNVs were simultaneously detected in matched BM clonal PCs and CTCs from the same patients. As expected, the genes with the highest frequency in MM such as to KRAS, NRAS, and BRAF were present in these samples, and were shared between patient-paired BM clonal PCs and CTCs with similar allele fractions, as shown by the 95% confidence interval for each mutation. As indicated earlier, the only exception was for patient MM447, in which there was potential contamination with non-malignant cells. Further validation using whole exome sequencing of 5 additional samples of CTCs that did not have matched BM samples but were sequenced without WGA was performed (FIG. 5C and FIG. 6).

Figure 7:
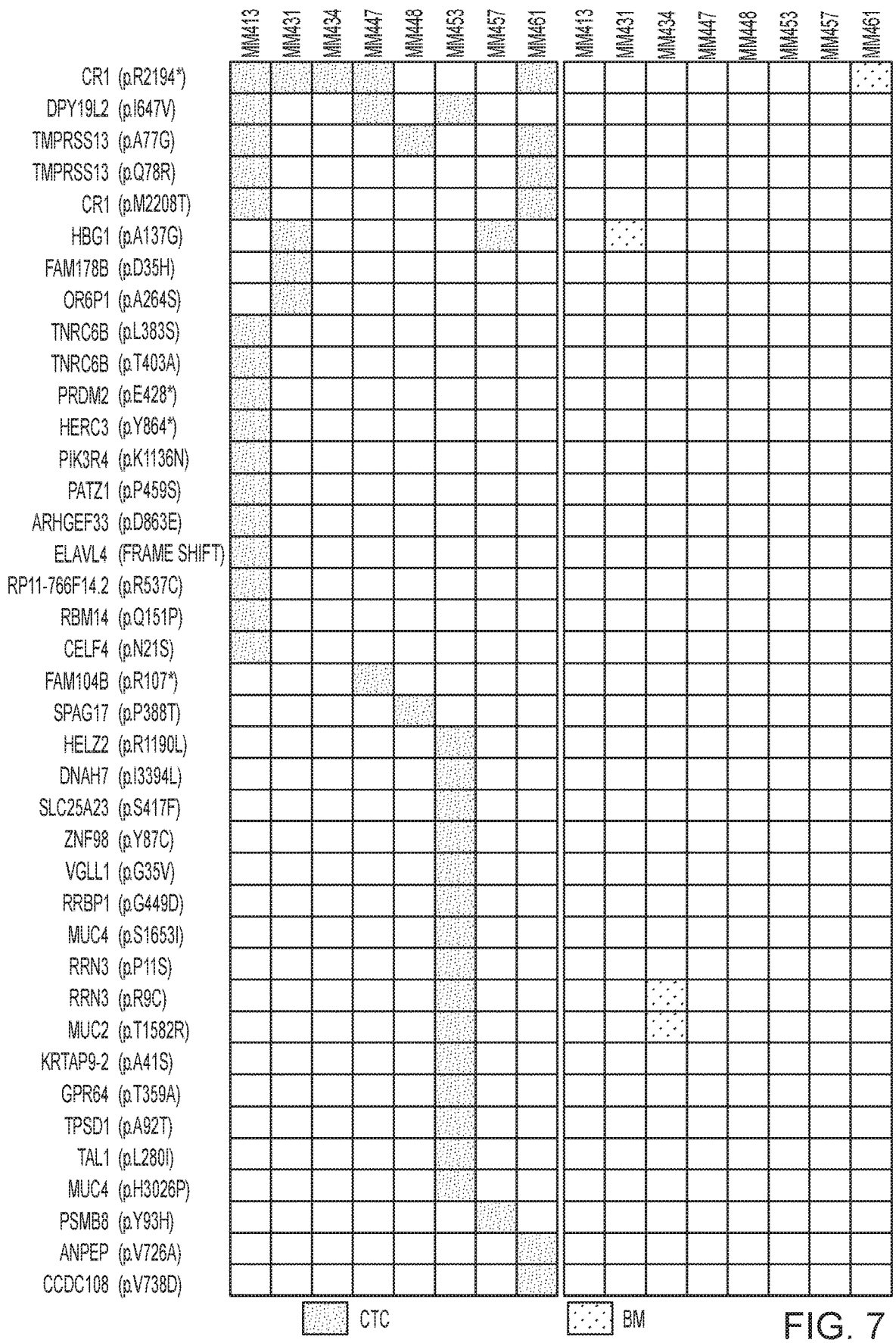
FIG. 7 is a chart showing unique SNVs identified in CTC. Unique SNVs were identified by comparing BM and CTC samples from each patient.
Figure 8:
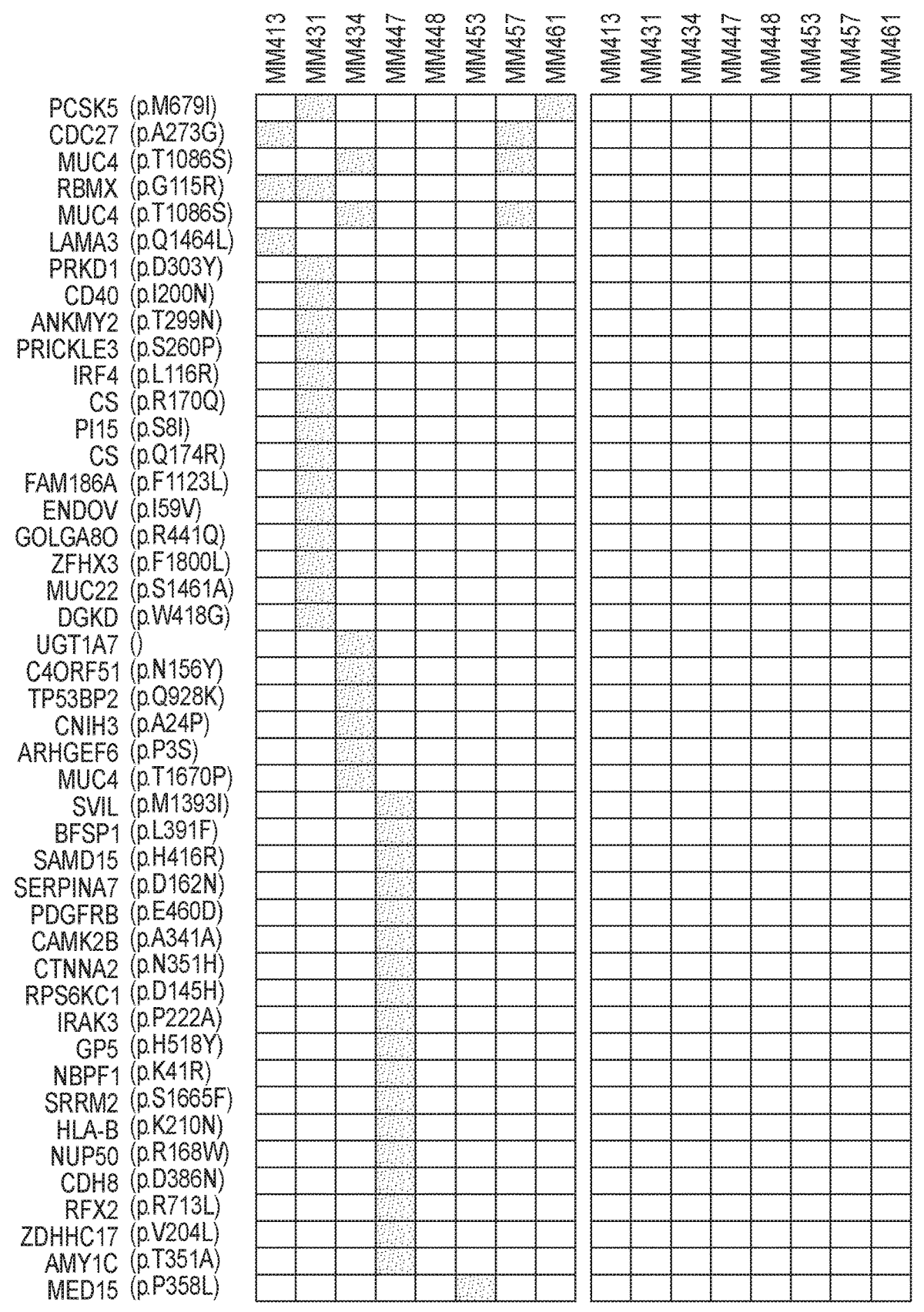
Figure 8:
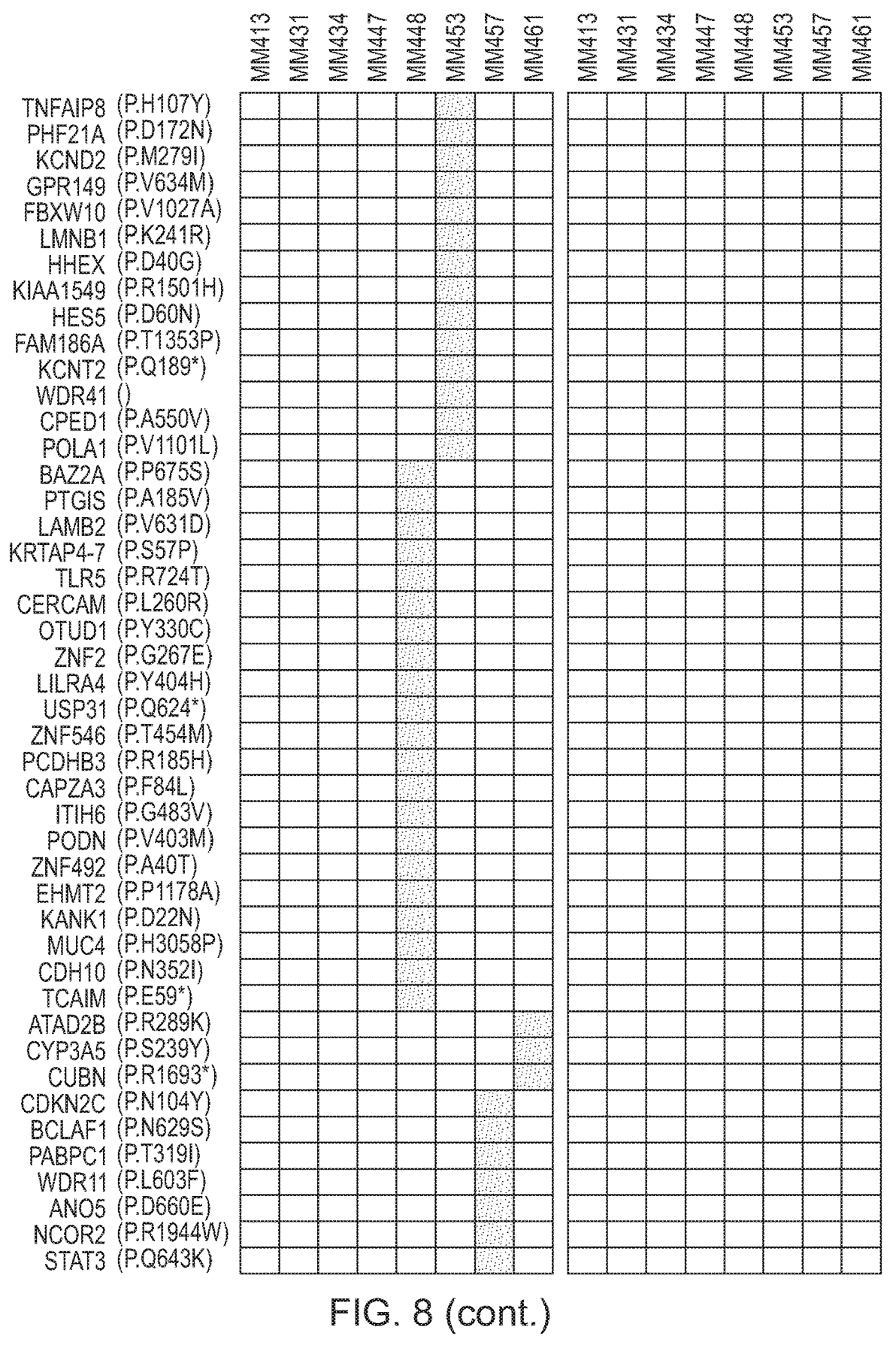

We next investigated the differences in AF distribution in CTCs and BM clonal PCs that could be potentially attributed to the presence of unique SNVs in each fraction. We identified several unique mutations present in CTC or BM clonal PCs (FIGS. 7-8); of those, up to 39 NS-SNV were identified as CTC-specific (FIG. 7), and 6 NS-SNVs in 4 genes (CR1, DPY19L2, TMPRSS13 and HBG1) were detected in CTC from multiple patient samples. We evaluated copy number variations (CNVs) and compared them between matched BM and PB tumor cells across paired samples. For samples in which WGA was performed, we called CNVs using the two parallel libraries separately and only retained shared CNVs. As described in the Table 6, a significant concordance between BM clonal PCs and CTCs was observed.

TABLE 6

Concordance of CNVs found in BM and CTC.

| Patient | # CNVs in CTC | # CNVs in BM | % BM CNVs found in CTC | Notes |
|---|---|---|---|---|
| MM413 | 730 | 139 | 68.35% | WGA for CTC |
| MM431 | 873 | 100 | 85.00% | WGA for CTC |
| MM434 | 1048 | 127 | 46.46% | WGA for CTC |
| MM447 | 728 | 202 | 29.21% | WGA for CTC |
| MM448 | 962 | 178 | 72.47% | WGA for CTC |
| MM453 | 166 | 158 | 82.28% | No WGA for BM and CTC |
| MM457 | 975 | 101 | 34.65% | WGA for CTC |
| MM461 | 1306 | 1297 | 43.79% | WGA for both CTC and BM |

Figure 5D:
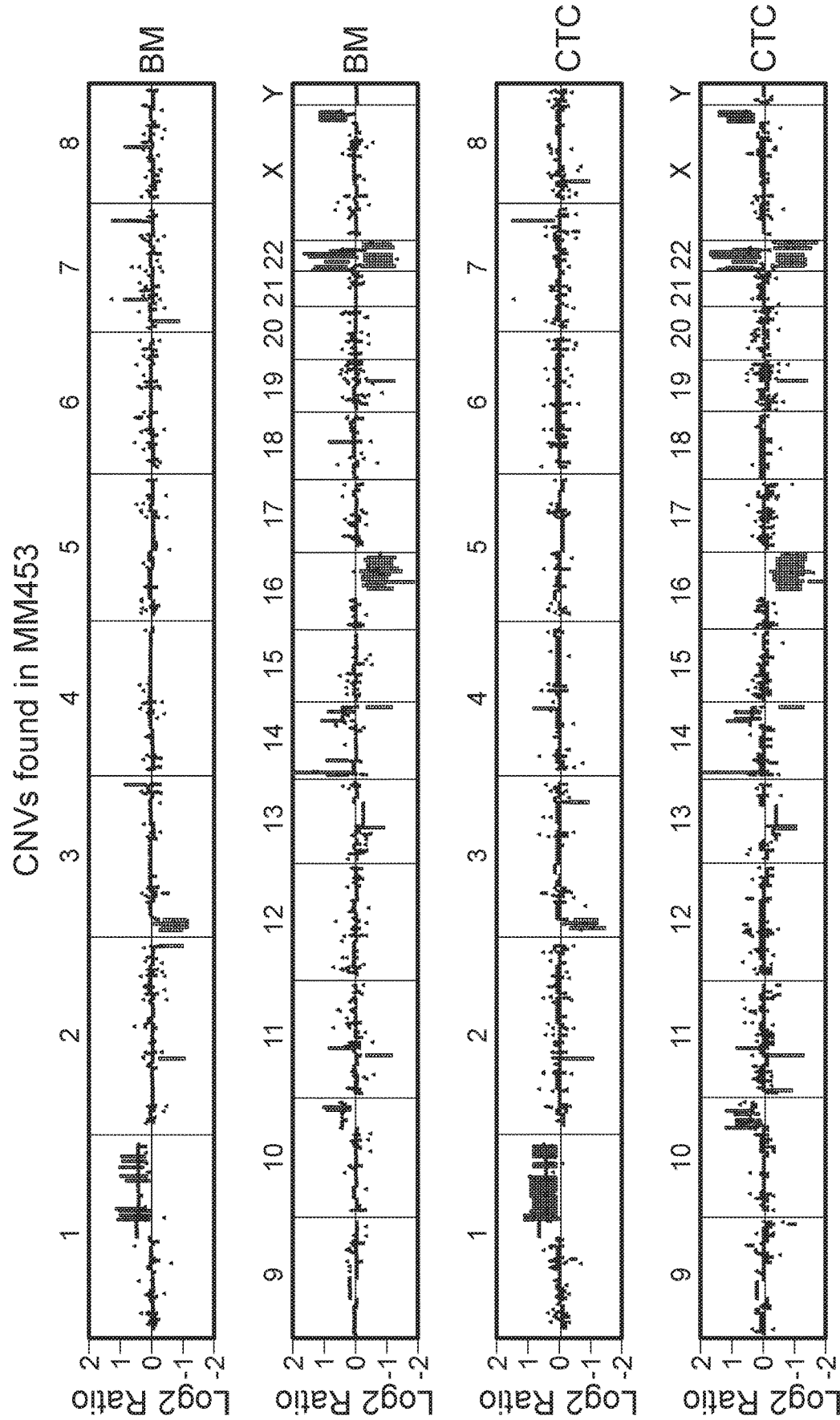

In sample MM453, for which no WGA was applied on BM or CTC, we were able to detect more than 80% of CNVs shared between BM and CTC samples. Previously reported MM-related CNVs such as 1q21 amplification and 16q deletion were present both BM clonal PCs and CTCs from this patient (FIG. 5d) (Corre et al., 2015 *Blood* 125:1870-1876; Walker et al., 2010 *Blood* 116:e56-65; Mohamed et al., 2007 *American Journal of Hematology* 82:1080-1087; Jenner et al., 2007 *Blood* 110:3291-3300). In samples with WGA, such as those from patient MM431, there were about 100 CNVs found in the BM sample and 85% of those were also found in CTC.

Discussion

In MM, there is a marked fluctuation of different clones throughout patients' clinical course implying that multiple bone marrow aspirates are needed to determine the genomic profile of patients, specifically with the development of new targeted therapies for actionable mutations (e.g., B-RAF inhibitors for patients with B-RAF mutations). Accordingly, the primary objectives of our study was to determine the overall applicability of performing genomic characterization of MM patients non-invasively, and define if the mutation profile of CTCs reflected that of patient-paired BM clonal PCs.

Our results reveal that in MM, PB CTCs can be used as a non-invasive biomarker to perform mutational profiling of MM samples with an overlap of 79% of the mutations present in matched BM clonal PCs from the same patients. A higher number of SNVs were identified in BM samples, which can be partially explained because WGA performed in CTCs may have actually eliminated mutations that could have been detected otherwise, since we only called for mutations that were present in both WGA duplicates. However, this is a standard method used to avoid false mutation calls, and WGA was applied to most PB samples due to low number of CTCs. Conversely, we observed 21% of CTC-specific mutations, and 4 (CR1, DPY19L2, TMPRSS13 and HBG1) were noted in multiple patient samples. It should be noted that key driver genes were identified in both BM and CTC (BRAF, KRAS and NRAS); indicating that although the mutation landscape of CTCs does not completely overlap with that of BM myeloma PCs, the clinically relevant information is fully represented in peripheral blood CTCs.

The ability to use peripheral blood (PB) samples to determine the mutational landscape of MM patients during disease presentation and progression eliminates the need for multiple invasive BM aspirates to determine genomic alterations and monitor clonal evolution during disease progression and after therapeutic interventions.

Our study defines the clinical significance of sensitive CTC monitoring by measuring larger numbers of cells with higher sensitivity, among uniformly treated patients enrolled in prospective clinical trials or using sequential peripheral blood samples. Of note, even by using sensitive MFC immunophenotyping, CTCs remain undetectable in a small fraction of MM patients which showed lower relapse rates compared to cases in which CTCs do circulate in PB; conversely, patients with increasing CTC levels in sequential samples had significantly inferior survival. Thus, MFC represents a widely available technique for a fast and sensitive screening of CTCs that not only affords prognostic information, but also guides the laboratory for the feasibility of subsequent deep-sequencing studies in patients with detectable CTCs, thereby avoiding unnecessary sequencing costs among patients with undetectable CTCs.

Our results delineate the clinical value of sensitive monitoring of CTCs, and should encourage CTC enumeration in larger series of patients to establish the role of serial CTC monitoring in the management of patients with MM. Together, this study defines a new role for CTCs in the prognostic and molecular profiling of MM patients, and provides the rationale for an integrated flow-molecular algorithm to detect CTCs in PB and identify candidate patients for non-invasive genomic characterization to predict outcomes.

Material and Methods

Patient Sample Collection and Study Approval

For CTC enumeration studies by MFC, we obtained samples from 50 newly diagnosed patients with symptomatic MM who were prospectively enrolled on the Spanish clinical trial PETHEMA/GEM2010MAS65 (sequential chemotherapy with 9 cycles of bortezomib-melphalan-prednisone (VMP) followed by 9 cycles of lenalidomide-low dose dexamethasone (Rd) n=27, or alternating cycles of VMP and Rd up to 18 cycles, n=32).

In addition, we prospectively collected samples from patients seen in the clinic at Dana-Farber Cancer Institute (DFCI) from 2011-2012. A total of 64 unique patients with MM with relapsed disease or in remission/on maintenance therapy were included in this study. In addition, 28 patients had sequential samples of CTCs (N=66 samples) that were used to determine the association of sequential CTC changes with overall survival.

For whole exome sequencing studies, we obtained 8 samples of newly diagnosed untreated patients whose bone marrow, CTC and germline T lymphocytes were available and selected for exome sequencing. Additional whole exome sequencing studies were performed in 5 patients with flow-sorted CTCs but without available BM clonal PCs.

The review boards of participating centers approved the study, which was conducted according to the Declaration of Helsinki and International Conference on Harmonization Guidelines for Good Clinical Practice. All patients provided written informed consent.

Detection of CTCs by Multiparameter Flow Cytometry (MFC)

The detection of CTCs in EDTA-anticoagulated PB samples collected from the 50 elderly, newly-diagnosed, transplant-ineligible MM patients prospectively enrolled in the GEM2010MAS65 trial was performed following the guidelines of the European Myeloma Network, and was based on a singular combination of antigens that allows the identification of aberrant phenotypes in MM patients. Accordingly, MFC studies were performed using a 4-color monoclonal antibody combinations (CD38-FITC/CD56-PE/CD19-PerCPCy5.5/CD45-APC) as previously described in prior publications for sensitive detection of minimal residual disease (Paiva et al., 2015 *Blood* 125:3059-3068; Paiva et al., 2015 *Haematologica* 100:e53-55; Paiva et al., 2012 *Blood* 119:687-691).

Noteworthy, the identification of phenotypically aberrant myeloma PCs in PB (i.e.: CTCs) is easier than MRD monitoring in post-treatment BM samples since normal circulating PCs in PB are homogeneously positive for CD19 and CD45; furthermore, CTC-screening in PB was performed after determining patient-specific aberrant immunophenotypes in matched BM myeloma PCs. CTCs were initially identified on the basis of intermediate/strong CD38 expression and low/intermediate side scatter signals; discrimination between myeloma and normal PCs was performed by the recognition of aberrant phenotypic expression profiles such as simultaneous down-regulation of CD19, CD38 and CD45, with or without over-expression of CD56. For patients in whom CD45 or CD19 was positively expressed, lack of CD19 or CD45, respectively, dim CD38 intensity and/or bright CD56 staining (equal or higher than that of natural-killer cells) allowed identification of myeloma PCs in the vast majority of cases. Data acquisition was performed in a FACSCantoII flow cytometers (Becton Dickinson Biosciences—BDB—San Jose, Calif.) using the FACSDiva 6.1 software (BDB), and allowing for $2 \times 10^6$ leucocytes/tube to be selectively stored. Data analysis was performed using the Infinicyt software (Cytognos SL, Salamanca, Spain), and the presence of CTCs was established after the identification of a cluster with 20 or more myeloma PCs, at a sensitivity level of $10^{-5}$. Noteworthy, the discrimination between plasma cells with normal phenotypes vs. those phenotypically aberrant (e.g., CTCs) is irrespective of the individual patients' aberrant phenotypic profile. Thus, the sensitivity of the assay depends exclusively on the number of cells analyzed, and the sensitivity is stable providing that ≥2.000.000 leukocytes are measured (using a cut-off of 20 myeloma PCs in 2.000.000 leukocytes to define a cluster of CTCs; limit of detection of $10^{-5}$).

For the DFCI samples, whole blood samples were treated with Red Blood Cell Lysis Solution (Miltenyi Biotec) to obtain the total fraction of leukocytes. Leukocytes were labeled with a combination of antihuman CD45-APC-Cy7, CD19-PE-Cy7, CD38-V450, CD56-BrilliantViolet (BD), CD138-PC5 and CD28-FITC (Beckman Coulter), and subsequently the cells were analyzed using FACSaria II flow-cytometer (BD Biosciences). CTCs were identified on the basis of intermediate/strong CD38 expression and strong CD138 expression with aberrant phenotypic expression profiles such as simultaneous down-regulation of CD19 and CD45, with or without over-expression of CD56 or CD28. For the sake of consistency, CTC enumeration was performed similarly across all samples from participating DFCI and Spanish centers, after independent and blinded review of raw FCS files.

Whole Exome Sequencing

BM myeloma PCs and CTCs were sorted from paired BM and PB from 8 patients with symptomatic MM using a FACSAriaIIb sorter (BD Biosciences). Both tumor fractions were sorted according to the individual patient-specific aberrant phenotypes, and PB T-lymphocytes were simultaneously collected for germline control. Genomic DNA was extracted using QlAamp DNA micro kit (QIAGEN, Valencia, Calif.) according to the manufacturer's protocols and double stranded DNA concentration was quantified using PicoGreen dsDNA Assay kit (Life Technology). The cell number of CTC used and total amount of genomic DNA obtained are shown in Table 7.

TABLE 7

Number of cells and DNA quantity of sequenced samples.

| Sample ID | Cell number | | | DNA quantity (ng) | | |
|---|---|---|---|---|---|---|
| | CTCs | BM PCs | T-Cells | CTCs | BM PCs | T-Cells |
| 413 | 86,000 | 20,000,000 | 3,600,000 | 160 | 4,170 | 348 |
| 431 | 48,000 | 1,172,000 | 4,000,000 | 157 | 2,241 | 7,553 |
| 434 | 26,300 | 2,095,000 | 7,400,000 | 232 | 2,761 | 4,673 |
| 447 | 5,200 | 216,000 | 842,000 | 176 | 1,465 | 1,073 |
| 448 | 15,000 | 1,300,000 | 5,000,000 | 294 | 1,642 | 8,334 |
| 453 | 300,000 | 110,000 | 2,300,000 | 1,022 | 101 | 2,343 |
| 457 | 11,400 | 100,000 | 1,400,000 | 279 | 513 | 2,930 |
| 461 | 37,100 | 840,000 | 2,000,000 | 259 | 829 | 1,688 |

For cases in which the total amount of DNA extracted from BM myeloma PCs (n=1) and CTCs (n=7) was limited, the gDNA was amplified using GenomePlex Whole Genome Amplification (WGA) Kits (Sigma-Aldrich) according to manufacturer's introduction. To capture the coding regions, we used the SureSelectQXT Target Enrichment kit (Agilent, Santa Clara, Calif.). All sequencing was performed on the illumina HiSeq 2000 platform (illumina) at the New York Genome Center, New York, N.Y., USA or at the Broad Institute, Cambridge, Mass.

Curation of MM and Pan-Cancer Driver Genes

Cancer driver genes were curated from published larger scale WES studies specifically; pan cancer driver genes were retrieved from tumor portal (http://www.tumorportal.org), which defines driver genes as those with statistical significance (Q-value <0). MM drivers were curated from MM tumor portal (www.broadinstitute.org/mmgp) or recent integrative studies of MM (Lohr et al., 2014 Cancer Cell 25:91-101; Bolli et al., 2014 Nature Communications 5:2997).

Read Mapping and Variant Analysis

Paired-end 125 bp reads were aligned to the GRCh37 human reference using the Burrows-Wheeler Aligner (BWA-ALN v0.6.2) and processed using the best-practices pipeline that includes marking of duplicate reads by the use of Picard tools (v1.83), realignment around indels, and base recalibration via the Genome Analysis Toolkit (GATK v2.7.4). Single nucleotide variants (SNVs) were called by MuTect (v1.5) using default parameters, with an additional filter that requires at least 3 high quality reads supporting alternative variants. As whole genome amplification introduces random errors, two libraries were constructed in parallel for samples with WGA, and only the shared SNVs identified in both libraries were kept for subsequent analysis.

Quality Control of Sequencing Data

To evaluate the overall quality of sequenced samples, we used BamUtil (http://genome.sph.umich.edu/wiki/BamUtil) to calculate various statistics, including the total number of reads, mapping rate, percentage of proper pairs, and duplication rate. Given that the SureSelectQXT v4 platform covers around 51M, a mean coverage was calculated for each sample. Since exome sequencing results in uneven coverage, the mean coverage is usually too simple a statistic to describe the overall quality. We thus evaluated the distribution of the mean coverage across all targeted regions. The DepthOfCoverage function from GATK (v2.74) was used with the "−mmq 10" parameter. By doing so we removed all unmapped reads, duplicated reads and reads with low mapping quality (<10).

Somatic Copy Number Identification

Samtools v0.1.18 was used to calculate coverage at the base pair level. Reads with low mapping quality (−q 1) were removed. VarScan v2.3.7 was used to compare read depths between BM/CTC and germline samples for contiguous regions of coverage. After normalizing for the total sequencing depth, the relative copy number change was inferred as the log 2 ratio for each contiguous region. The DNAcopy (Seshan and Olshen 2010) library from BioConductor (http://www.bioconductor.org/) was applied to identify copy number changes with significance. The resulting p-values were adjusted for multiple testing and represented as false discovery rates (FDR). Regions with 10 or more fragments, log 2 ratio >0.5 or <−0.5 and FDR<0.1% were selected.

Characterizing the Shared and Unique SNVs in BM Clonal Cells and CTCs

Since SNVs were identified by comparing tumor to normal genomes, the detection power at a specific locus is determined by the coverage of this locus at both tumor genome and normal genomes. MuTect currently uses cutoffs of at least 14 reads in the tumor and at least 8 in the normal to define whether the gene in question is sufficiently covered in the tumor and normal samples to be sensitive enough to call mutations. For a fair comparison, we only focused on the loci that were covered in both the CTC and BM samples. Furthermore, for samples with WGA, we required that the interrogated loci were covered by both libraries.

Survival Analysis

Survival time was measured from the time of CTC collection to the date of an event (death, progression or last visit). Curves were plotted by the Kaplan-Meier method, and the log-rank test was used to estimate the statistical significance of differences observed between curves. For the sequential cohort, we tested the association of survival of MM patients with CTC trends by performing linear regression (CTC~time) and using the obtained slopes to represent CTC trends. Since the slopes were not normally distributed, we adopted the median absolute deviation (MAD) as a robust measure of the variability. Then a cutoff was defined as (Median+MAD), and samples with slopes greater than this cutoff were classified as the "CTC UP" group that was then compared to other samples. All analysis was performed in the R statistical computing environment (http://www.r-project.org/).

Example 2. Biomarker Panel

Figure 9:
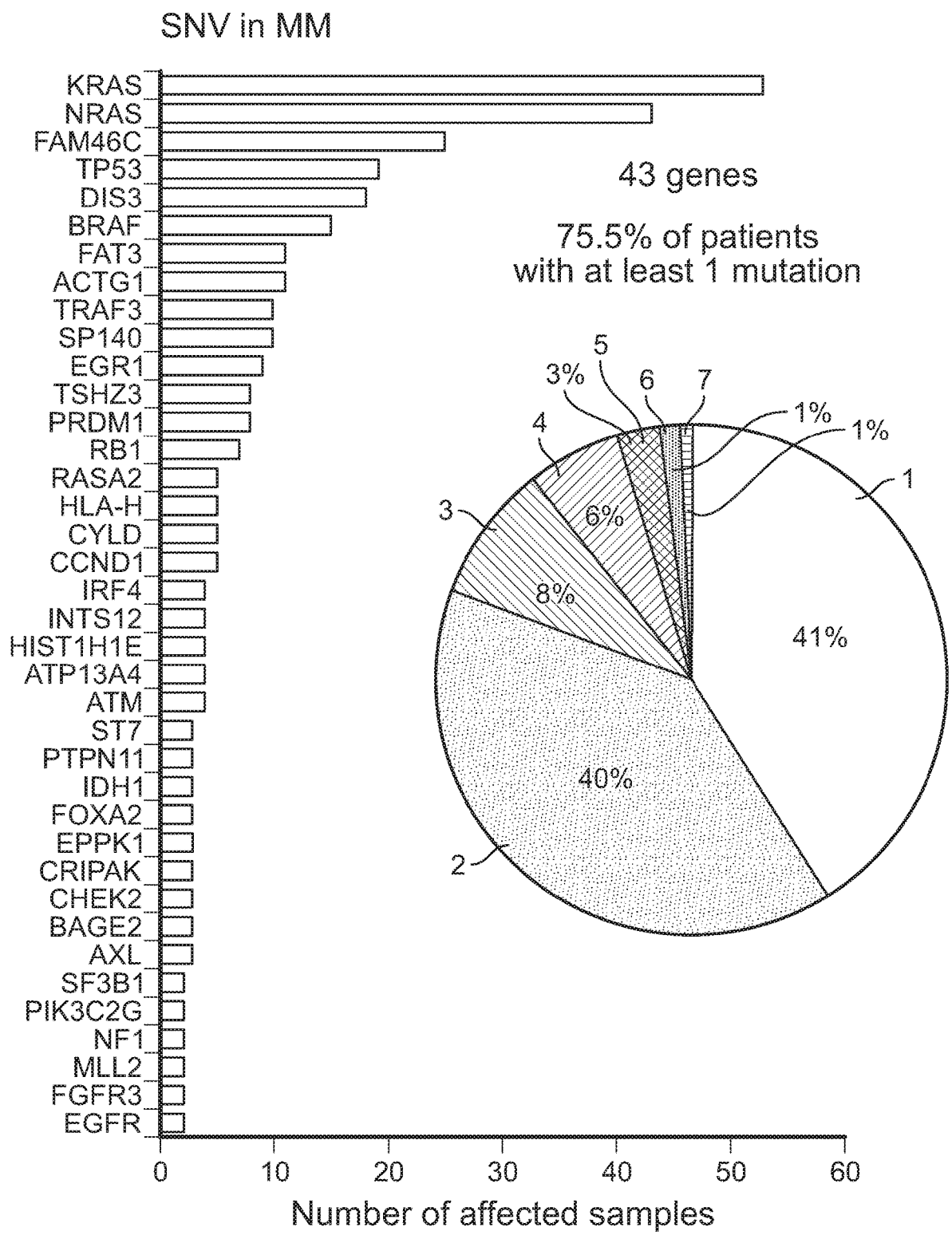
FIG. 9 includes a bar graph and a pie chart showing genes in a targeted multiple myeloma (MM) panel. The panel was designed based on common mutations identified in MM in bone marrow cells.

We developed a targeted sequencing panel for MM by using Hybrid Capture to detect somatic mutations, translocations and copy number variations (CNV) in MM patients. The panel was developed using whole exome sequencing databases published to date (Lohr et al., 2014 *Cancer Cell* 25:91-101; Bolli et al., 2014 *Nature Communications* 5:2997; Chapman et al., 2011 *Nature* 471:467-472) and defined genes recurrently mutated in MM and known as oncogenes/tumor suppressor genes, such as NRAS, KRAS, BRAF and TP53 (FIG. 9). 75% of patients with MM presented with at least one of these mutations. In addition, the panel covers CNVs and translocations involving IGH that occur in about 60% of patients; namely t(4;14), t(6;14), t(11;14), t(14;16), t(14;20). CNVs specifically covered include 1q21 amp, del13q and del17p that are known to confer an adverse prognosis in MM.

We tested our panel on 10 matched serum and bone marrow samples of patients with MM. To examine mutations in cfDNA, serum and plasma samples were centrifuged at 2,000×g for 10 minutes to remove cell debris. cfDNA was extracted with Qiagen circulating nucleic acid kit and 50-100ng cfDNA quantified by nanodrop was isolated. Prior to library preparation, DNA was fragmented (Covaris sonication) to 250 bp and further purified using Agencourt AMPure XP beads. Size-selected DNA was then ligated to specific adaptors during library preparation (Rubicon kit). Each library was made with sample-specific barcodes and quantified using qPCR. The bone marrow and cfDNA samples were pooled separately in equimolar concentrations to a total of 500 ng for custom enrichment using the Agilent SureSelect hybrid capture kit. The captures were pooled and sequenced in one lane of an Illumina HiSeq 2500 in Rapid Run Mode. Pooled sample reads were de-convoluted (de-multiplexed) and sorted using the Picard tools. Reads were aligned to the reference sequence b37 edition from the Human Genome Reference Consortium using Burrows-Wheeler Aligner (BWA). The alignments were further refined using the Genome Analysis Toolkit (GATK) tool. Mutation analysis for single nucleotide variants (SNV) was performed using MuTect v1.1.4 and annotated by Oncotator. Insertions and deletions (InDels) were called using Indel Locator (http://www.broadinstitute.org/cancer/cga/indelocator). The allelic fraction from duplicate cfDNA samples were compared with tumor DNA (from CD138+bone marrow cells) from the same patients at the same time point. We found high consistency of non-synonymous SNV calls between replicates of cfDNA and between tumor and matching cfDNA samples. Duplicate samples were compared between each other and with matched tumor DNA samples. We were able to identify mutations at as low AF as 0.22% as illustrated by a KRAS Q61H mutation, also detected in the matched tumor DNA sample. Correlation within 2 duplicates was more than 0.85 for AF<1%, without false positive mutation call. Duplicate samples were compared between each other and with matched tumor DNA samples. Because of low allelic fraction in the cfDNA, we changed the Mutect settings of fraction of contamination to 0.2%, and were able to detect mutations in the cfDNA fraction that were present in the bone marrow samples.

Example 3. Genomic Exosomal DNA (exoDNA) and Progression from MGUS/Smoldering MM to MM Cells were cultured in media supplemented with 10% exosome-depleted FBS. FBS was depleted of bovine exosomes by ultracentrifugation at 100,000×g for 17 hours. Supernatant fractions collected from 48 hour cell cultures were pelleted by centrifugation at 300×g for 10 minutes. The supernatant was collected and centrifuged at 2,000×g for 10 minutes followed by a centrifugation step of 10,000×g at 4° C. for 10 minutes to discard cellular debris. Afterward, the medium was filtered using a 0.22 µm pore filter (Millex GP). Exosomes were then harvested by centrifugation at 100,000×g for 70 minutes. The exosome pellet was resuspended in PBS and collected by ultracentrifugation at 100,000×g for 70 minutes (Beckman 32Ti rotor). The exosome pellet was pooled in 500 µL of PBS and incubated with 10 µl of DNase I (1 unit/µL, catalog number M6101, Promega) at 37° C. for 30 minutes. Subsequently, 50 µL of DNase stop solution (catalog number M199A, Promega) were added, and the samples were heated at 65° C. in a water bath for 5 minutes. Next, the pooled exosome pellet was washed in 11 mL of PBS, and a second step of ultracentrifugation was performed at 160,000×g at 4° C. for 2 hours. After aspiration of the supernatant, the exosome pellet was suspended in PBS. For functional assays where exosomes were used, the concentration of total proteins contained in each exosome pellet was quantified using the BCA assay (Pierce); exosome quantities are therefore expressed as micrograms of containing proteins.

The DNA was extracted using the QIAamp DNA micro kit according to the manufacturer's instructions. Finally, the DNA was eluted in distilled water and stored at −20° C. until processing. The amount of DNA from cell medium-derived exosomes was quantified using PicoGreen® (Quant-iT™ PicoGreen® dsDNA assay kit, catalog number P11496, Life Technologies).

PCR analysis was performed with exoDNA using the specific designed primers. PCR was performed in a mixture of 5 µL of 10× Accuprime Pfx Reaction mix, 1.5 µL, each of forward/reverse primers (10 µM), template DNA, 0.4 µL of Accuprime pfx (25 U/µL), and distilled water was added to the reaction. Amplification was carried out in a 2720 Thermocycler (ABI) under the following conditions: 95° C. for 2 minutes; 35 cycles of 95° C. for 15 seconds, 55° C. for 30 seconds, 68° C. for 1 minute; 68° C. for 5 minutes; endless 4° C. PCR products were purified using the QIA-quick PCR purification kit. Subsequently, a sequencing reaction was performed using BigDye terminator kit (v3.1, Life Technologies). Sequencing products were separated on an ABI 3730 automated sequencer.

Example 4. Prognostic Role of Circulating Exosomal miRNAs in Multiple Myeloma In this example, the prognostic significance of circulating exosomal microRNAs (miRNAs) in MM was examined.

Introduction

Multiple Myeloma (MM) is a hematological malignancy characterized by a clonal proliferation of plasma cells in the bone marrow microenvironment. However, the clinical and biological heterogeneity of this malignancy leads to variable responses to therapy and outcomes. With a vast increase in therapeutic choices in MM and improved outcomes, the issue of risk stratification to dissect this heterogeneity is becoming more critical as it may lead to tailored therapies for different groups of patients. It is helpful to have prognostic biomarkers that reflect tumor burden and stage of the disease, tumor biology (such as chromosomal abnormalities and gene expression signatures), or factors present in the host that indicate fitness to therapy.

The most widely used prognostic factors in MM are currently the International Staging System (ISS) (Griepp et al., *J. Clin. Oncol.*, 23:3412-20 (2005)) based on albumin and beta-2 microglobulin levels in the peripheral blood at the time of diagnosis—and chromosomal abnormalities such as t(4:14), 17p deletion and 1q21 amplification (Avet-Loiseau et al., *Leukemia*, 27:711-7 (2013)). A new revised ISS (R-ISS) system has been proposed that includes poor risk cytogenetics and LDH for improved characterization of patients with poor survival (Palumbo et al., *J. Clin. Oncol.*, 33:2863-9 (2015)). However, despite these advances, patients within similar prognostic groups display heterogeneous outcomes indicating that current prognostic factors used in MM are suboptimal in stratifying patients with poor risk features. Combining information about cytogenetic abnormalities and ISS with other molecular markers may therefore further improve their prognostic value.

Results

Characterization of Circulating Exosomes in MM

Peripheral blood circulating exosomes from MM patients and normal controls were first characterized. After isolation of circulating exosomes, the presence of exosomes was confirmed by transmission electron microscopy with immunogold labeling for CD63 and CD81, specific markers of exosomes. The diameter of isolated exosomes was confirmed to be around 120 nm by Nanosight analysis (data not shown).

Figure 10A:
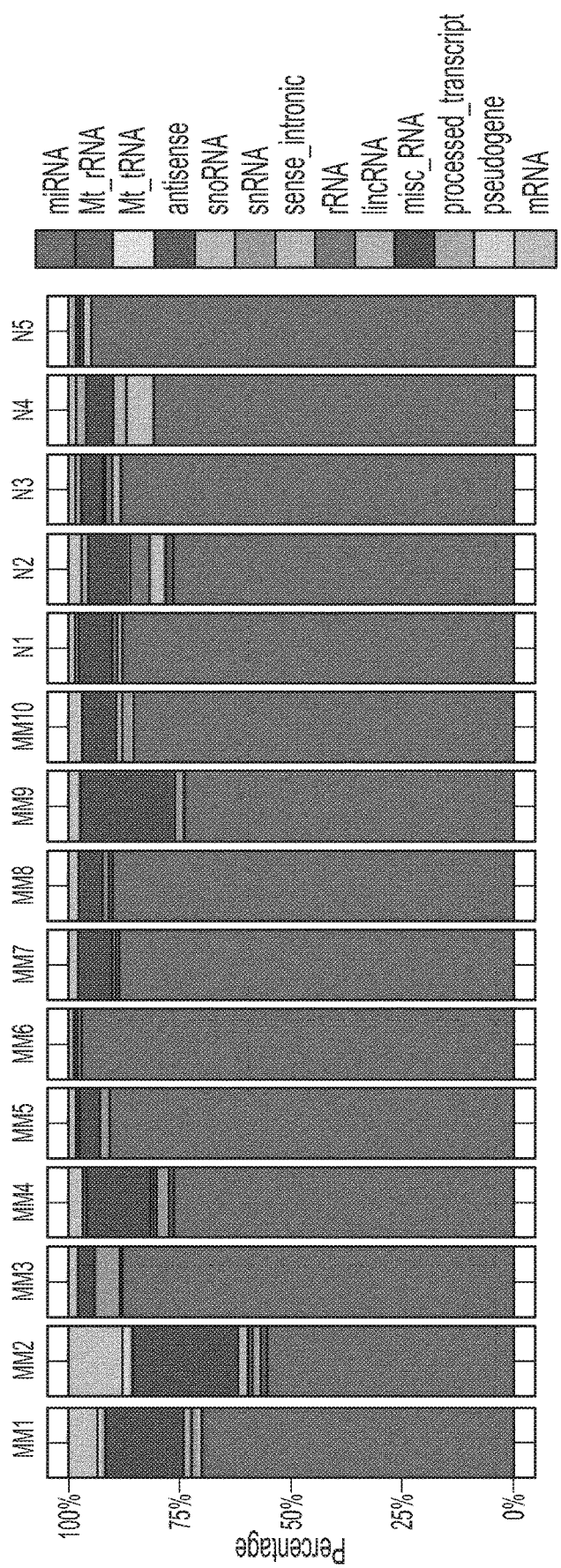
FIG. 10A is a distribution of mappable small RNAs by next generation sequencing in circulating exosomes from 10 MM patients and 5 healthy donors.
Figure 10C:
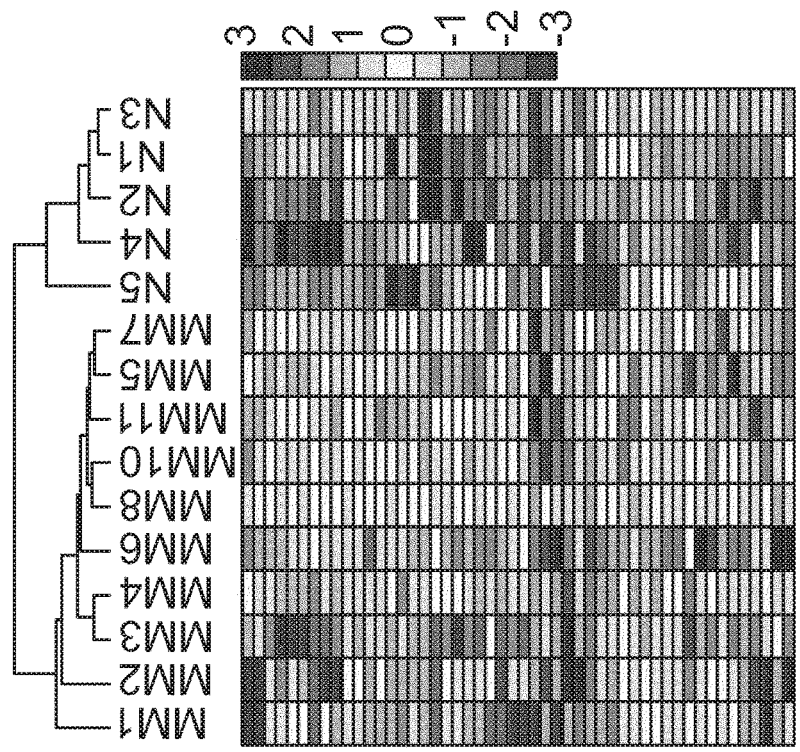
FIG. 10C is a heat map of differentially expressed exosomal miRNAs in MM vs. HD.
Figure 10B:
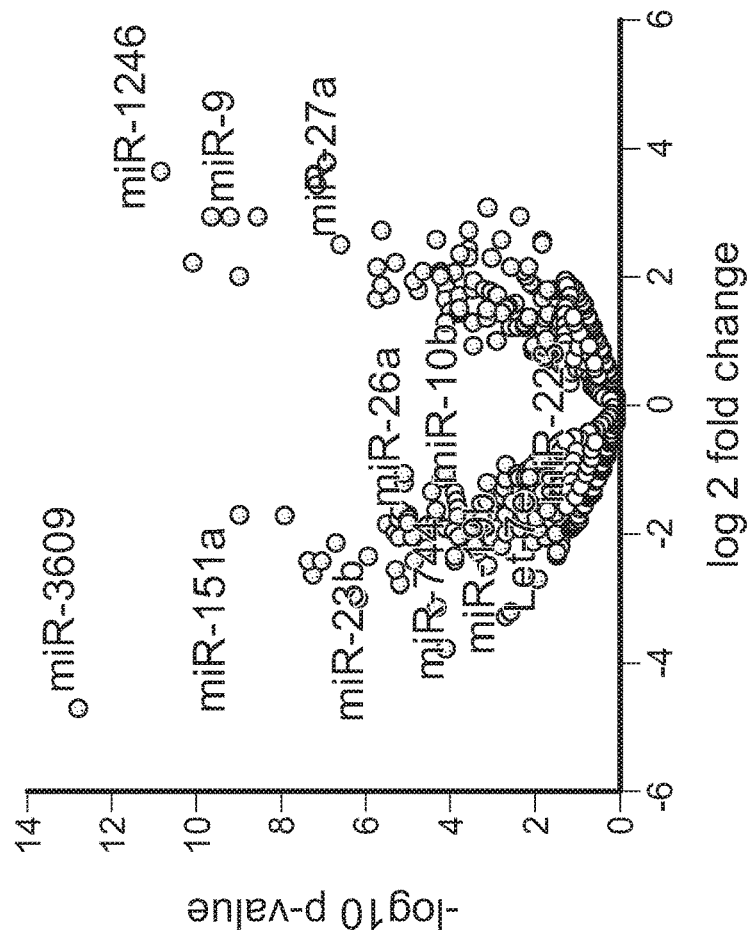
FIG. 10B is a volcano plot for MM against healthy donors (HD) exosomal miRNA expression level from miRNA sequencing, showing the adjusted p value (−log 10) vs. fold change (log 2).
Figure 10D:
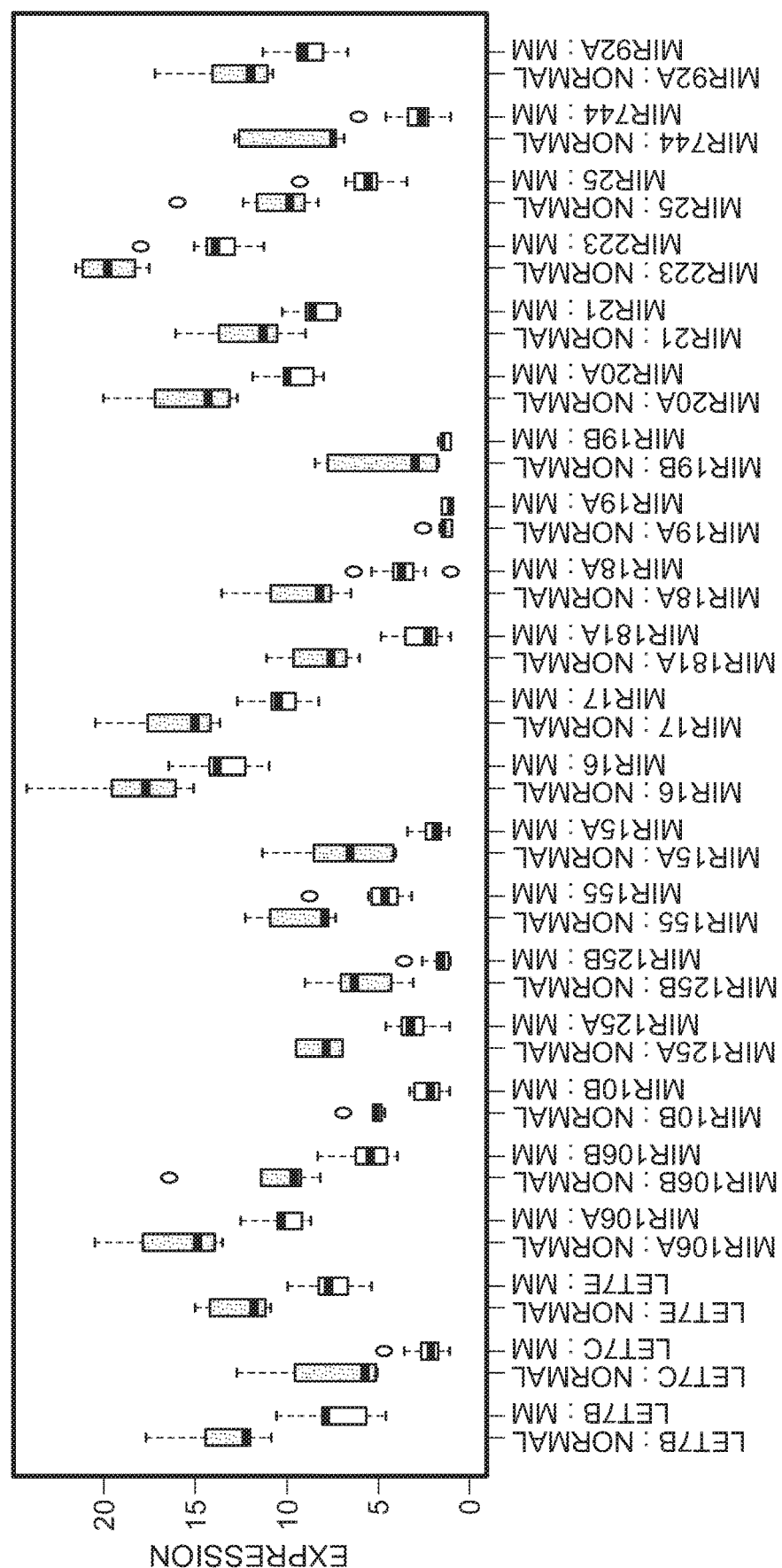
FIG. 10D shows the results of quantitative RT-PCR of circulating exosomal miRNAs in 11 MM patients and 5 healthy donors. Box plots represent the median and standard deviation of the normalized expression level of 22 miRNAs. miRNA (microRNA), Mt_rRNA and Mt_tRNA (ribosomal and transfer RNA located in mitochondrial genome), snoRNA and snRNA (small nucleolar and nuclear RNA), rRNA (ribosomal RNA), lincRNA (long intergenic non-coding RNA), misc_RNA (miscellaneous other RNA), mRNA (messenger RNA).

To define the content of exosomes in terms of small RNAs, a small RNA sequencing was performed from circulating exosomes of 10 newly diagnosed MM patients and 5 healthy individuals. The large majority of mappable RNAs were miRNAs (88% in MM samples and 86% in healthy donor samples). The rest of the RNAs were represented by small nuclear and nucleolar RNA (sno/snRNA), ribosomal RNA (rRNA), messenger RNA (mRNA), long noncoding RNA (lincRNA) and unclassified RNA (miscRNA). There was no difference in terms of distribution of small exosomal RNA between MM and healthy donor samples (FIG. 10A). 2044 miRNAs were identified, among which 91 were downregulated and 67 were up-regulated in circulating exosomes of MM patients compared to healthy control samples with a FDR<5% (FIG. 10B). A hierarchical clustering, based on the differentially expressed miRNAs, successfully separated samples from MM patients and normal donors (FIG. 10C). The results of these miRNAs were confirmed by qPCR indicating that specific miRNAs were downregulated in MM exosomes compared to normal healthy controls (FIG. 10D). These results suggest the presence of specific miRNAs expressed in circulating exosomes that enables differentiation between normal and malignant samples.

Relationship Between Exosomal miRNAs and PFS in MM

It was then aimed to determine the prognostic role of exosomal miRNAs after adjusting for ISS and cytogenetics. 22 miRNAs were selected based on their differential expression in MM samples and biological relevance based on studies of tumor samples in MM (data not shown). The goal was to identify a clinically significant prognostic signature of circulating exosomal miRNA in patients with newly diagnosed MM. Therefore, serum samples of 156 patients were obtained with newly diagnosed MM who were uniformly treated with Bortezomib and dexamethasone (from the IFM group). The clinical characteristics of the patients are listed in Table 8.

TABLE 8

Clinical characteristics of patients.

| | N = 156 | |
|---|---|---|
| | N | % |
| Age, median (range) | 56 | (34-73) |
| Sex, male | 89 | 57 |
| IGH | | |
| IgG | 81 | 52 |
| IgA | 36 | 23 |
| IgD | 2 | 1 |
| No heavy chain | 22 | 14 |
| No data | 15 | 10 |
| IGL | | |
| Kappa | 94 | 60 |
| Lambda | 41 | 26 |
| No data | 21 | 14 |
| ISS | | |
| 1 | 63 | 40 |
| 2 | 56 | 36 |
| 3 | 33 | 21 |
| No data | 4 | 3 |
| FISH* | | |
| 13q deletion | 59 | 40 |
| t(4; 14) | 14 | 10 |
| 17p deletion | 5 | 3 |
| Poor risk** | 17 | 12 |
| Progression-free survival | | |
| Relapse or death | 111 | 71 |
| 3 years PFS, % (CI) | 50 | (42-28) |
| Overall survival | | |
| Deaths | 27 | 17 |
| 3 years OS, % (CI) | 97 | (95-99) |
| Follow-up | | |
| Median FU, years (CI) | 5.6 | (5.4-5.9) |

*Del13q: unknown for 7 subjects; t(4;14): unknown for 14 subjects. Del7p: unknown for 5 subjects. Poor risk cytogenetics for 16 subjects.
**Poor risk cytogenetics include t(4;14) and/or del17p.

All serum samples were harvested at diagnosis, before initiation of therapy. The median follow up of the cohort was 5.6 years (range, 5.4-5.9).

Figures 11A, 11B:
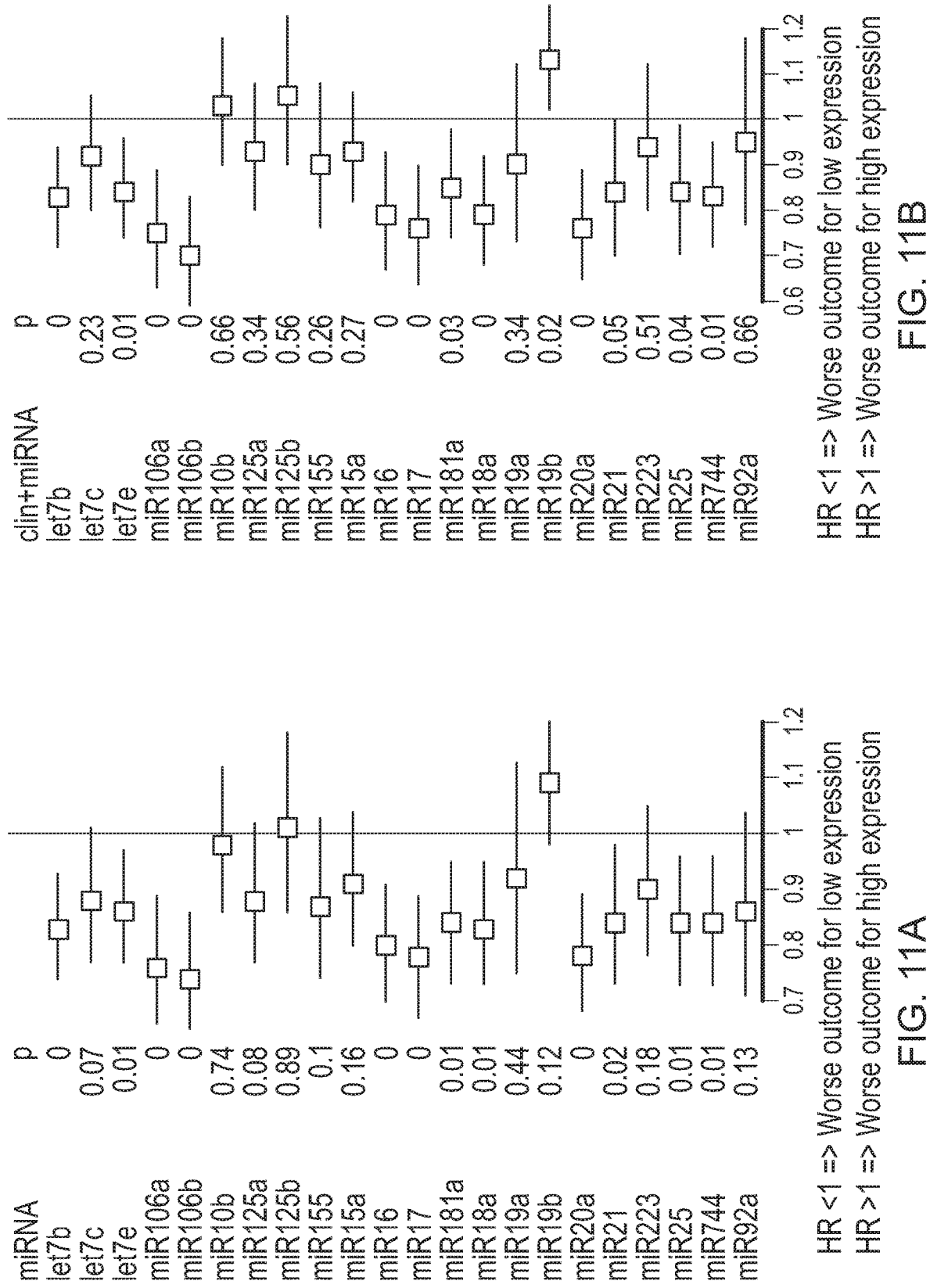
FIG. 11A is a forest plot of progression-free survival (PFS) in patients with Multiple Myeloma (MM), according to the univariate analysis of circulating exosomal miRNA.
FIG. 11B is a Kaplan-Meier survival curve of PFS in patients with MM according to the univariate analysis of circulating exosomal miRNA.
Figure 11C:
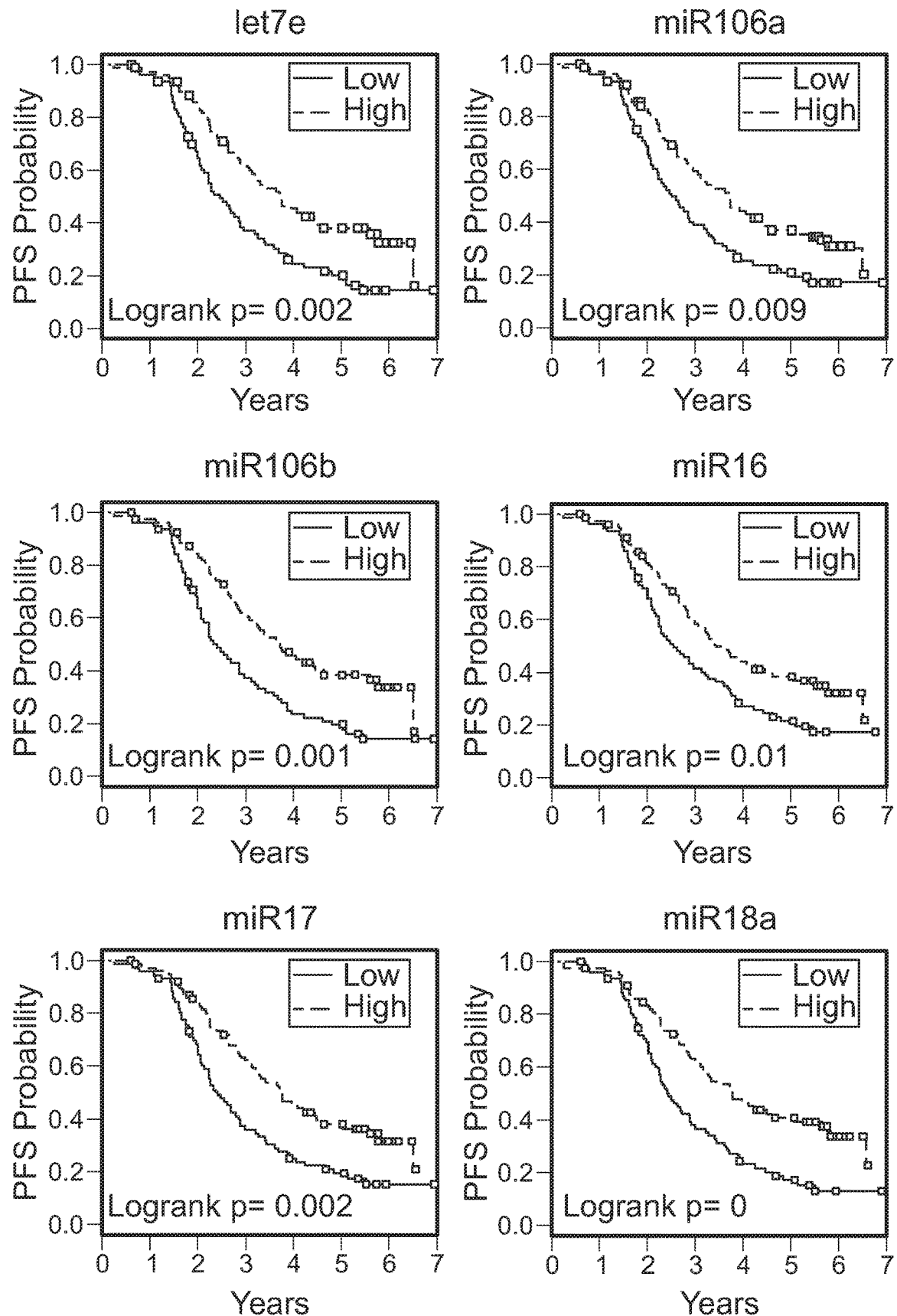
FIG. 11C is a forest plot of the Cox PH model using each miRNA individually together with ISS and cytogenetics.

A custom quantitative RT-PCR Taqman low-density array (TLDA) was performed to assess the clinical significance of the 22 selected miRNAs. From univariate analysis, several miRNAs were significantly associated with worse PFS, specifically let-7b, let-7e, miR-106a, miR-106b, miR-16, miR-17, miR-181a, miR-18a, miR-20a, miR-21, miR-25 and miR-744 (FIG. 11A). Each of these miRNAs had a hazard ratio <1, indicating a worse outcome for patients with a low expression of the miRNA. Moreover, these miRNAs remained significantly associated with PFS even when ISS and cytogenetics was accounted for (FIG. 11B). The effect of the miRNAs on PFS was illustrated by Kaplan-Meier curves with dichotomized miRNAs at the median (FIG. 11C). These data indicate that specific miRNAs can be critical in defining worse prognosis in patients with newly diagnosed MM even when one accounts for the usual prognostic factors used in these patients such as ISS and cytogenetics.

Multivariable Analysis

To evaluate the impact of all of the miRNAs together with ISS and cytogenetics in a multivariable model, a principal component (PC) analysis was used. This approach was used because of the high correlation of the miRNAs. It reduces the dimensionality and the multi-collinearity of the variables. Using this approach, six PCs were identified—as defined by linear combinations of the miRNAs. While all of the miRNAs were used to compute the principal components, the miRNAs that primarily defined the PC were determined. Considering that the miRNAs with the largest coefficients contribute the most to a PC, the following miRNAs primarily define each PC: 1st PC (let-7e, miR-106a, miR-106b, miR-16, miR-17, miR-18a, miR-20a and miR-25), 2nd PC (miR-19a and miR-19b), 3rd PC (miR-10b and miR-125b), 4th PC (miR-19b and miR-223), 5th PC (miR-125b and miR-181a) and 6th PC (miR-744 and miR-125a).

Figure 12A:
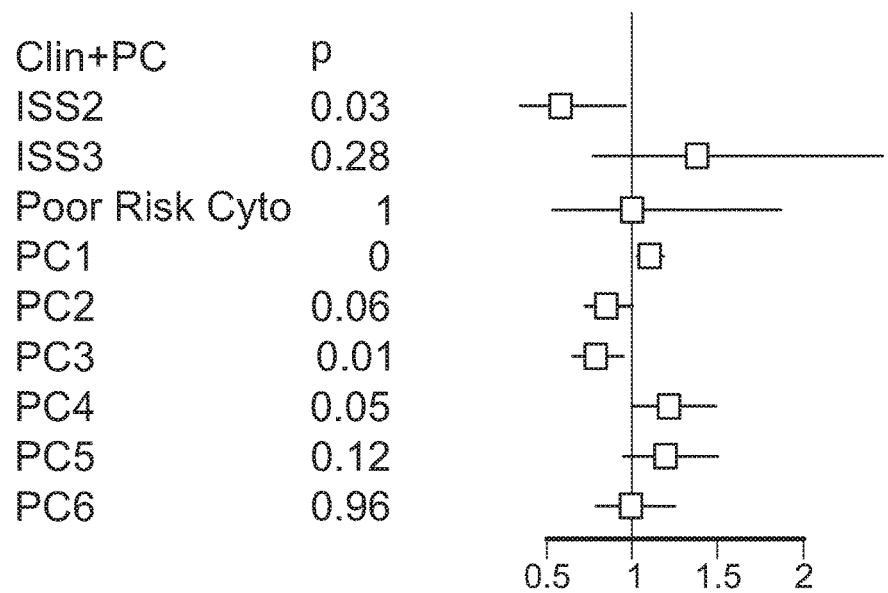
FIG. 12A is a forest plot of the Cox PH model using the Principal Component together with ISS and cytogenetics.

The six PCs were then used together with ISS and cytogenetics in a multivariable Cox PH model. PC1 was the most significant variable of the model (Table 9 and FIG. 12A).

TABLE 9

Multivariable Cox PH model of exosomal miRNA PC signatures and progression-free survival.

| Variable | | HR (95% CI) | P value |
|---|---|---|---|
| ISS | II vs. I | 0.58 (0.35; 0.96) | 0.07 |
| | III vs. I | 1.38 (0.77; 2.47) | 0.27 |
| Del17p and/or t(4;14) | | 0.99 (0.53; 1.8) | 0.99 |
| PC1 | | 1.1 (1.03; 1.18) | 0.003 |
| PC2 | | 0.85 (0.72; 1.01) | 0.06 |
| PC3 | | 0.78 (0.65; 0.94) | 0.01 |
| PC4 | | 1.22 (1.01; 1.49) | 0.04 |
| PC5 | | 1.19 (0.95; 1.49) | 0.12 |
| PC6 | | 0.99 (0.78; 1.25) | 0.96 |

* Missing indicators were used for unknown cytogenetics

Figure 12B:
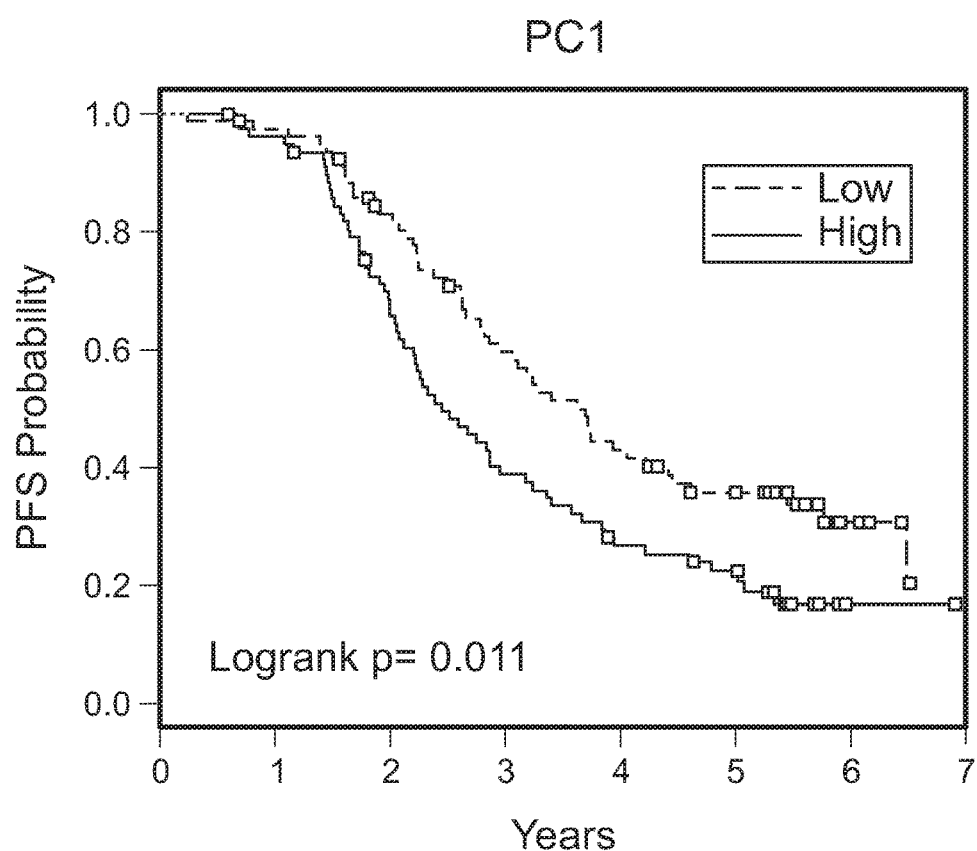
FIG. 12B shows Kaplan-Meier survival curves of PFS according to the PC1 miRNA signature in patients with Multiple Myeloma (MM).

Patients with a high PC1 signature had a shorter PFS compared to low PC1 signature (median PFS of 2.5 [95% CI: 2.2-3.2] vs. 3.62 [95% CI: 3.0-4.6], respectively, p=0.004), (FIG. 12B). To further evaluate the effect of the PC1 signature by ISS subgroups, we stratified the patients with ISS I, II and III diseases. The PC1 miRNAs signature had a significant effect on PFS for ISS I/II patients but not for ISS III patients (ISS I p=0.03, ISS II p<0.001, ISS III p=0.69).

Together, this data indicates that the circulating exosomal miRNAs as a group, defined by the PCs, adds to the prognostic relevance of ISS and cytogenetics to further stratify patients with poor outcome.

Discussion

In this study, a novel prognostic biomarker based on miRNAs from circulating exosomes was examined to improve the prediction of PFS in patients with MM. The results of the experiment described above show that circulating exosomes harbor specific miRNA content in MM compared to healthy donors. Furthermore, an exosomal miRNA signature predicts the PFS of patients with MM in an independent manner, and improves on the prognostic value of ISS and cytogenetic status in MM.

Established markers of prognosis in MM include the ISS and cytogenetics. The ISS classification is based on non-clonal markers instead that are albumin and beta-2 microglobulin (B2M). Although B2M is a useful marker of the tumor burden, it is not specific enough to define the clinical and biological heterogeneity of patients with MM. Cytogenetics and several gene expression signatures are truly reflective of the molecular and biological characteristics of the tumor clone. However, these are only performed on tumor cells obtained from bone marrow biopsies. Therefore, there is a need to develop non-invasive biomarkers that reflect the molecular aspect of the disease.

Cell-free miRNAs are attractive as prognostic biomarkers because they are non-invasive. However, many circulating miRNAs are passively released from apoptotic and necrotic cells, and therefore may not truly reflect the biological changes that occur in these tumor cells. In contrast, exosomes are actively secreted in the peripheral blood by different cell types including cancer cells and are biologically relevant as they promote tumorigenesis through miRNA transfer. Cancer exosomes are capable of cell-independent miRNA processing and transfer of mature miRNAs into recipient cells; they thus mediate significant transcriptome alterations in target cells and lead to induction of proliferation and the conversion of non-tumorigenic cells into tumor-forming cells. This indicates that exosomes carry specifically selected miRNAs as well as their own miRNA biogenesis machinery. Therefore, exosomal miRNAs truly represent specific molecular biomarkers in contrast to cell-free miRNAs. The exosomal PC1 signature includes: let-7e, miR-106a, miR-106b, miR-16, miR-17, miR-18a, miR-20a, and miR-25. Among them, three important family of miRNAs can be identified: the let-7 family, the miR-17-92 cluster, and the miR-106 family.

In summary, the data in this example provide an unprecedented finding of the prognostic significance of an exosomal miRNA signature in patients with MM. This exosomal miRNA signature can effectively classify patients with MM into groups at low and high risk of progression, and adds to the prognostic value of ISS and cytogenetics in MM. These results need to be validated in other independent prospective cohorts specifically with other therapeutic agents used in MM.

Materials and Methods

Plasma Samples from Patients with MM 156 serum samples were obtained from the Intergroupe Francophone du Myélome (IFM) collected between Jun. 14, 2006 and Dec. 16, 2008 for this study. All patients were newly diagnosed with MM, uniformly followed and treated with a combination of Bortezomib and Dexamethasone followed by high dose Melphalan and autologous stem cell transplant. None of the patients received therapy before the collection of blood samples. Criteria of diagnosis, clinical staging and risk stratification were assessed according to the International Myeloma Working Group (IMWG) guidelines (Kyle et al., Leukemia, 23:3-9 (2009)). The median follow-up was 5.6 years (95% CI 5.4-5.9). Patients provided written informed consent in accordance with the Declaration of Helsinki. In addition, samples from 5 healthy volunteers over the age of 40 (for age-matched comparison) were used for RNA sequencing studies.

Circulating Exosome Isolation

Circulating exosomes were isolated as described previously (Taylor et al., Methods Mol Biol., 728:235-46 (2011)). Exosomes were isolated from serum samples using a combined centrifugation and exosome isolation reagent method. Serum was isolated by centrifugation at 300 g for 10 min and further spun down at 2,000 g for 10 min and 10,000 g for 10 min, to remove dead cells and cell debris, respectively. Exosomes were harvested by adding an exosome isolation reagent for 30 min (ExoQuick solution) before centrifugation at 1,500 g for 30 min.

Electron Microscopy

Exosomes were characterized by electron microscopy using CD61 and CD81, as follows:

pelleted exosomes were fixed with 2% paraformaldehyde in 0.1 M phosphate buffer (pH 7.4), then processed for ultrathin sectioning and immunogold labeling using anti-CD63 and anti-CD81 antibodies and protein A coupled with 10- or 15-nm gold particles. Sections were observed at 80 kV on a TecnaiGβSpirit BioTWIN Transmission electron microscope (FEI), and images were recorded with an AMT 2k CCD camera.

RNA Extraction and RNA Sequencing

Total RNA was extracted from exosome pellets using the miRNeasy Micro Kit (Qiagen). Small RNA libraries were prepared and amplified using the NEBNext small RNA Library Prep Set (New England BioLabs). Amplified libraries were resolved on a 10% polyacrylamide gel for size selection. The 140 to 160 nucleotide bands correspond to adapter-ligated constructs derived from the 21 to 40 nucleotide RNA fragments were excised and recovered in DNA elution buffer. The average size distribution of each library was determined using Agilent Bioanalyzer with High Sensitivity Chip Kit (Agilent) and quantified on ABI 7900HT Fast RT-PCR instrument using the KAPA Library Quantification kit (Kapa Biosystems). Each library was adjusted to final concentration of 2 nM, pooled, and sequenced on an Illumina HiSeq 2000 sequencer for single read 50 cycles at the Center for Cancer Computational Biology at Dana-Farber Cancer Institute. The BCL files were demultiplexed using CASAVA 1.8.2 (Illumina) into fastq files. Raw sequencing reads were then analyzed by miRDeep2 to quantify known small RNA species.

Taqman Low-Density Array

For quantitative RT-PCR, a custom Taqman Low-Density Array (Life Technology) was designed. RNA concentrations were measured with a Qubit miRNA assay and 5 ng of miRNA was reverse transcribed using a miRNA RT kit (Taqman, Life Technology) and pre-amplified with a custom pool of primers and a Preamp Master Mix (Taqman, Life Technology). Quantitative PCR reactions were done with the Taqman Universal Master Mix II reagent in Custom Taqman Array Cards (384 well plate pre-loaded with 24 specific primers of interest) on a ViiA™ 7 Real-Time PCR System (Life Technology). All assays were done in duplicate and a subset of samples was also run in duplicates to test reproducibility. All Ct values above 35 cycles were considered as undetectable. qRT-PCR data was normalized using a robust global median normalization as described previously (D'Haene et al., *Methods Mol. Biol.*, 822:261-72 (2012)). Each plate was adjusted by a normalization factor as the difference between the global median Ct value and the plate median Ct value. The expression of miRNAs with ΔCt was calculated in which the maximal Ct value for a miRNA is subtracted from the specific value for this miRNA. The average of the replicate expression values of the miRNAs were used in the analysis.

Statistical Analysis

The primary outcome of interest was progression-free survival (PFS). The limited number of survival events (27 deaths) in this cohort precluded the analysis of overall survival (OS). The Cox Proportional Hazards (Cox PH) model was used to evaluate the effect on PFS of a) ISS and cytogenetics alone, b) each miRNA individually and c) each miRNA individually with ISS and cytogenetics. In these analyses, the miRNAs are included as continuous variables and ISS and cytogenetics as categorical variables. To illustrate the effect of the miRNAs on PFS graphically, the miRNAs were dichotomized at the median based on low versus high expression and the PFS was estimated and compared using the Kaplan Meier method and the log-rank test. Given the high correlation (Pearson correlation) of the miRNAs, a multivariate model with all variables was not considered. Instead principal components analysis (PCA) was used to reduce the dimensionality and multi-collinearity, and then the principal components (PC) that explained 80% of the original variation in the data were used in a Cox PH model to predict PFS with and without ISS and cytogenetics. In the PCA, the original data were centered and scaled. From the analysis, six principal components were determined to explain 80% of the variation in the data. While all of the miRNAs were used to calculate the PCs included in the Cox PH model, the magnitude of the coefficients were evaluated to determine the miRNAs that most influenced each PC. The likelihood ratio test was used to evaluate the added value when the miRNA PC was added to a Cox PH model with ISS and poor risk cytogenetics. Analyses comparing impact of miRNA PC on outcome were also performed by ISS. Sensitivity and specificity of the signature was evaluated using receiver operator characteristics (ROC) curve. All statistical analyses were performed in R. The following functions were used in the analysis: coxph function of the survival package for Cox PH model, prcomp from the stats packages, risksetROC and risksetAUC functions from the risksetROC package for ROC analysis.

Example 5. Whole-Exome Sequencing and Targeted Deep Sequencing of cfDNA Enables a Comprehensive Mutational Profiling of Multiple Myeloma We performed next generation sequencing of matched Cell-free DNA (cfDNA)/tumor DNA (tDNA) samples for 63 patients with newly diagnosed or relapsed MM, SMM, or MGUS. Whole-Exome Sequencing (WES) was performed on 30 matched samples cfDNA/tDNA/germline DNA from 10 patients with more than 5% of tumor fraction. Libraries were hybridized to the Nextera Rapid Capture Exome kit (Illumina) and then sequenced on HiSeq 4000 (Illumina). Targeted deep sequencing was performed on 32 matched cfDNA/tDNA samples from 15 patients using the HaloPlex HS technology (Agilent), allowing for molecular barcoding. Libraries were constructed according to the manufacturer's instructions and sequenced on HiS eq 2500. Sequencing data were analyzed using the Firehose pipelines, including MuTect, ABSOLUTE, RecapSeg, GISTIC and MutSig.

Figure 13:
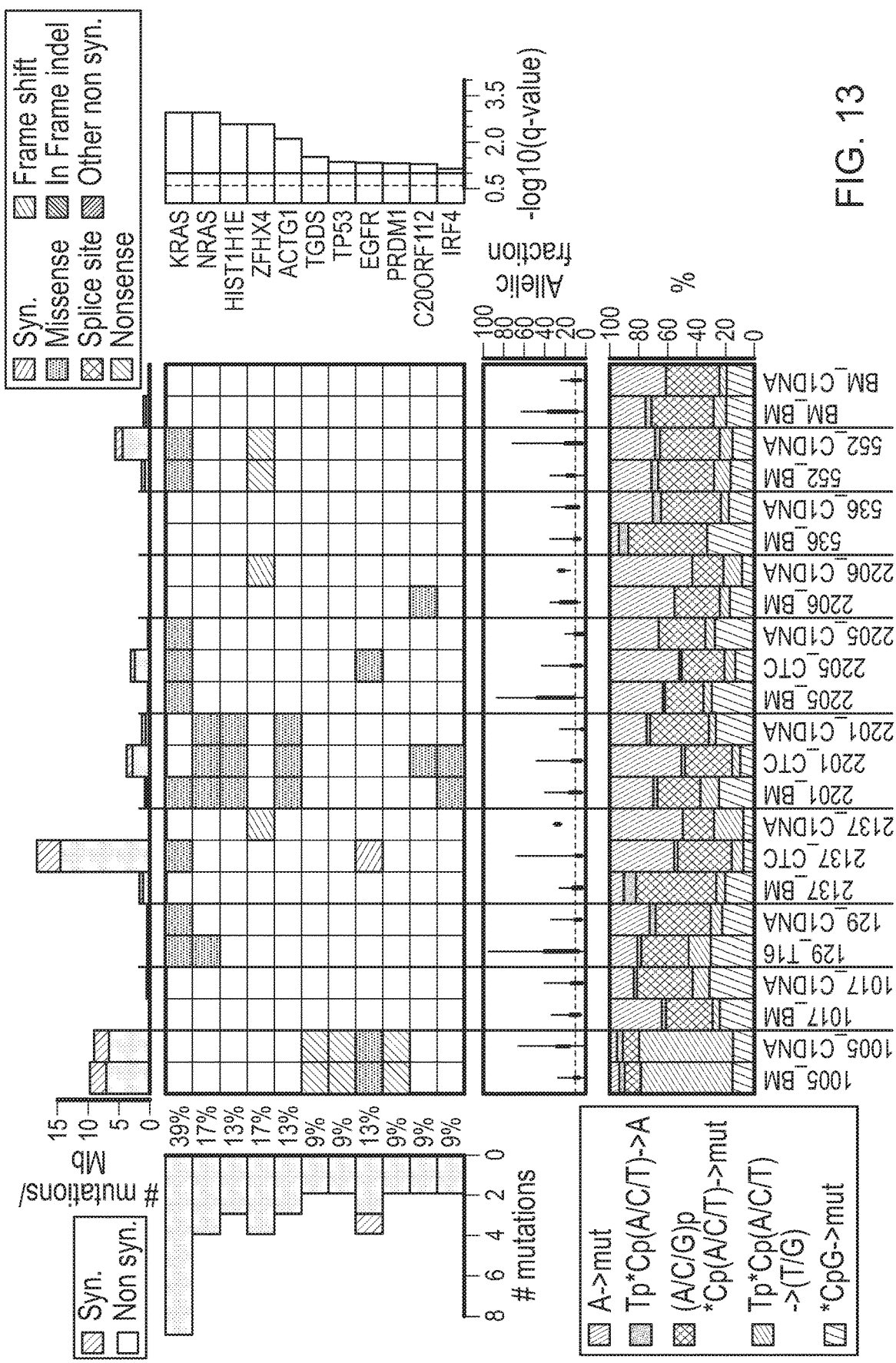
FIG. 13 shows the alteration status of significantly mutated genes in whole exome sequencing (WES) of tumor biopsy (BM), cell-free DNA (cfDNA), and circulating tumor cell (CTC) obtained from 10 patients with Multiple Myeloma (MM) that was predicted by MutSig2CV. Most somatic single nucleotide variants (SSNVs) detected in the tumor or cfDNA/CTC were confirmed to be present in cfDNA/CTC or tumor, respectively.
Figure 14:
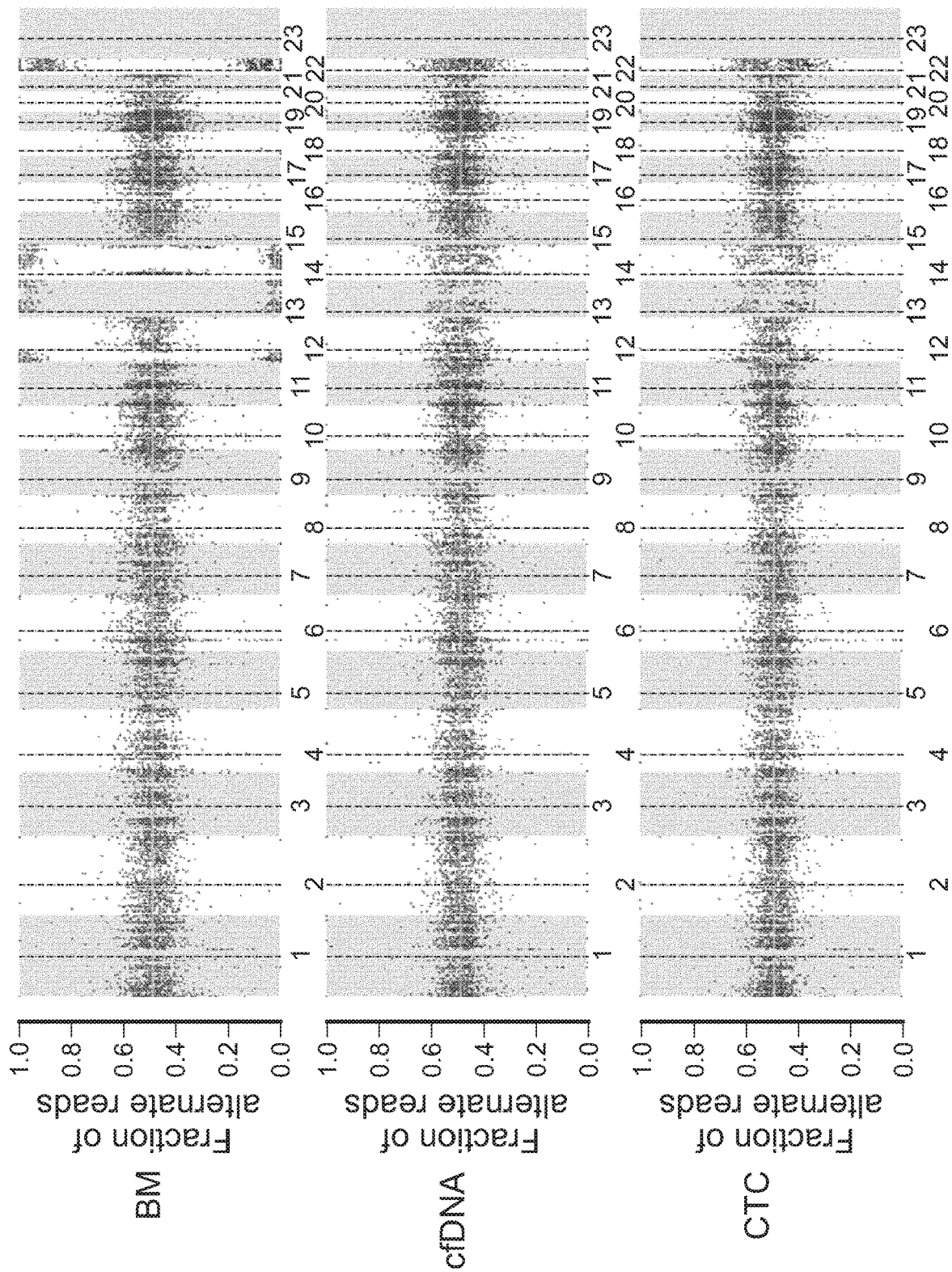
FIG. 14 is a representation of genome-wide copy number from whole exome sequencing (WES) of tumor biopsy (BM), cell-free DNA (cfDNA), and circulating tumor cell (CTC) from a patient with Multiple Myeloma. Somatic Copy Number Alteration (SCNA) for tumor, cfDNA, and CTC WES were identified using Allelic CapSeg. SCNAs were consistent among tumor DNA, cfDNA and CTC samples.
Figure 15:
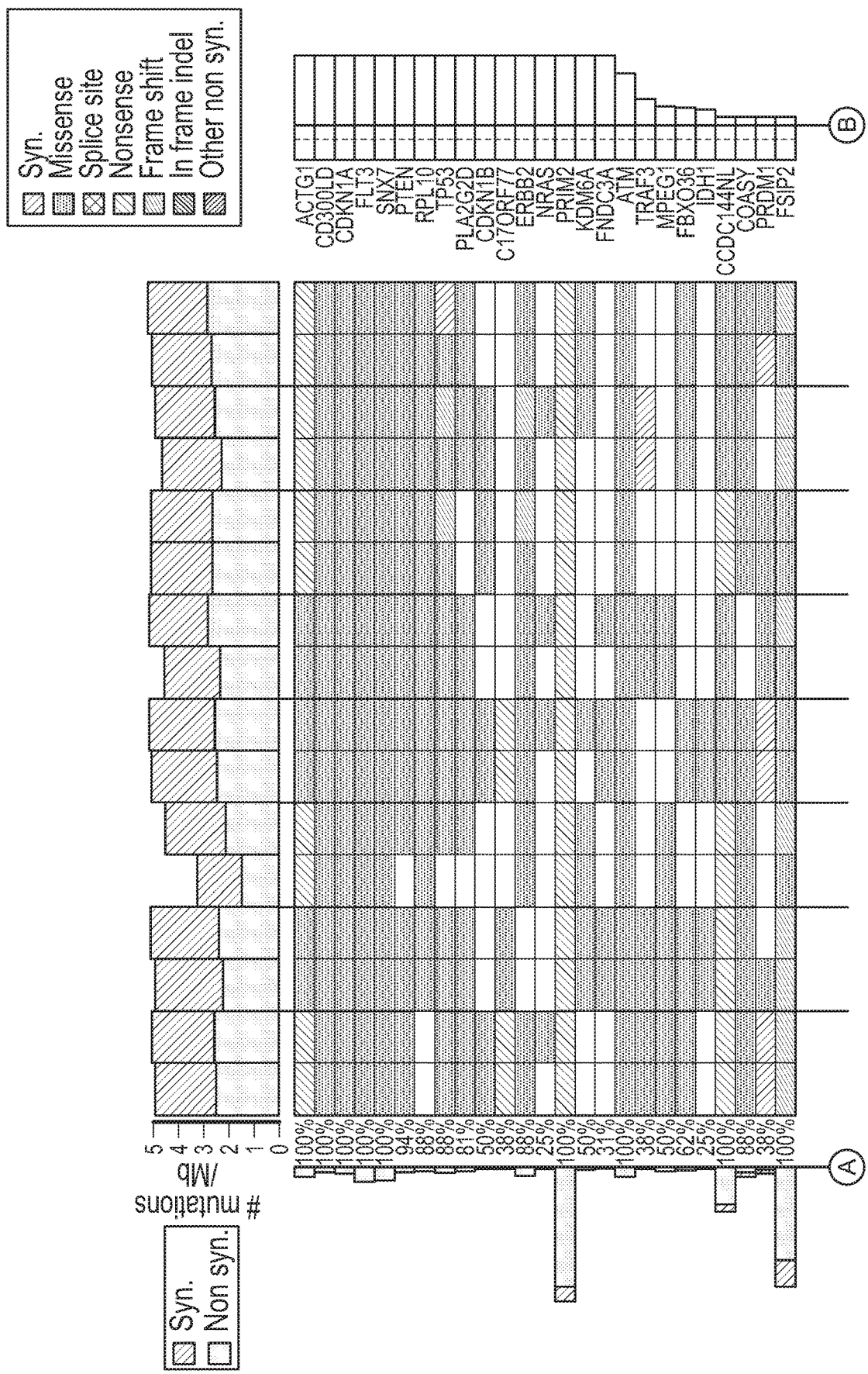
FIG. 15 is a summary of the alteration status of significantly mutated genes in deep targeted sequencing of tumor biopsy (BM) and cell-free DNA (cfDNA) from 8 patients with Multiple Myeloma (MM) that was predicted by MutSig2CV. Most somatic single nucleotide variants (SSNVs) detected in the tumor or cfDNA were confirmed to be present in cfDNA or tumor, respectively.
Figure 15:
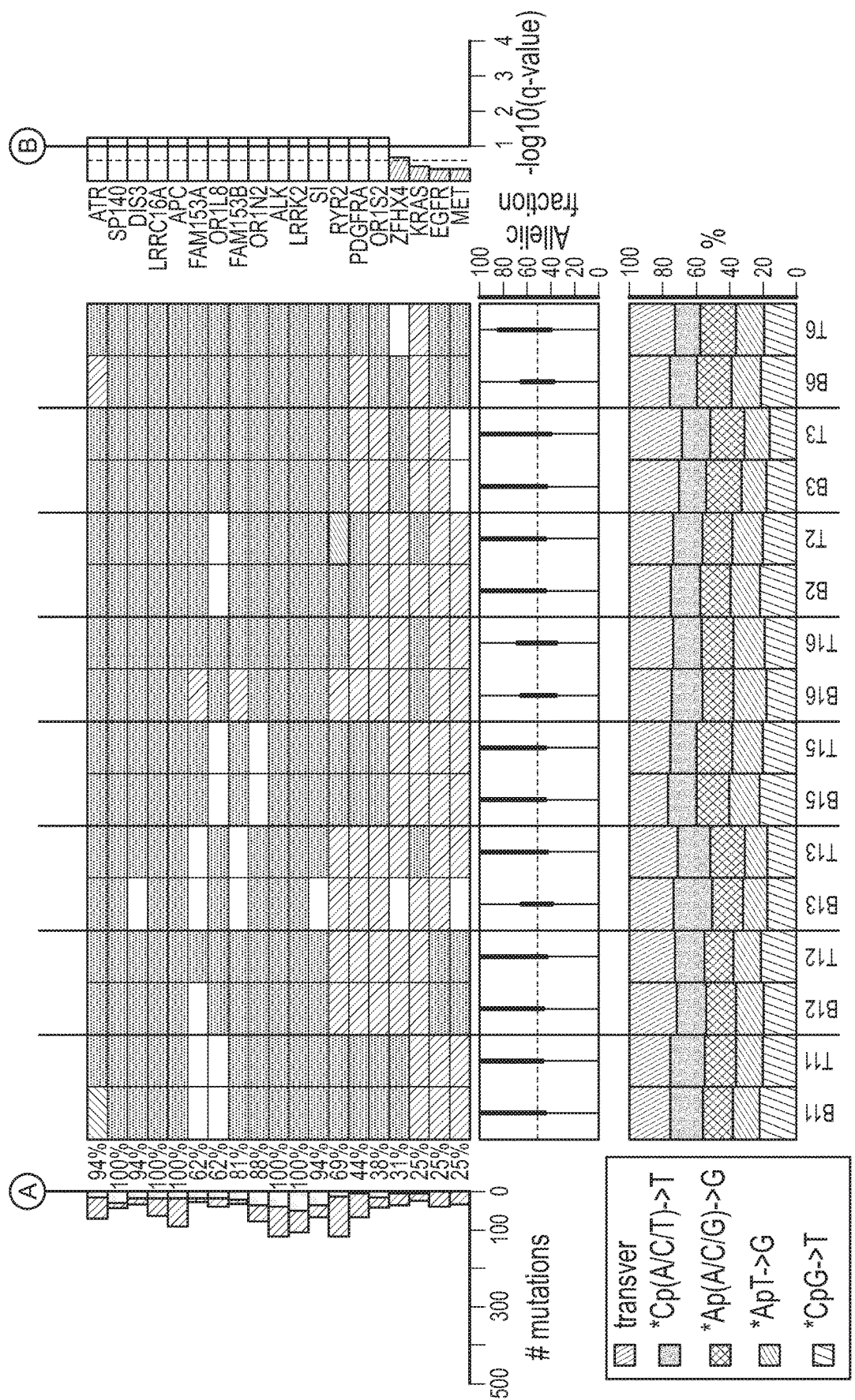

To assess whether cfDNA can capture the genetic diversity of MM and inform clinical management, we performed WES of matched cfDNA/tDNA/germline DNA samples for 10 patients (mean target coverage 194×). Copy number alterations (CNAs) assessed by WES (ReCapSeg) were consistent between cfDNA and tumor DNA. Similarly, focal CNAs assessed by GISTIC were consistent between tDNA and cfDNA. We then examined the overlap of somatic single nucleotide variants (SSNVs) between WES of cfDNA and matched tDNA. We found most (54-100%) of clonal and subclonal SSNVs that were detected in the tumor or cfDNA were confirmed to be present in cfDNA or tumor, respectively, FIGS. 13 and 14. To assess whether targeted deep sequencing of cfDNA could be a good proxy for tumor biopsy we used a targeted deep sequencing approach of known MM driver genes. Libraries were prepared using unique molecular barcodes to avoid high duplication rates, for 32 matched cfDNA/tDNA samples from 15 MM patients. We found similar frequencies of altered MM driver genes in both cfDNA and tDNA, including KRAS, NRAS, and TP53 as shown in FIG. 15, indicating that cfDNA can be used for precision medicine.

Our study demonstrates that both WES and targeted deep sequencing of cfDNA are consistently representative of tumor DNA alterations in terms of CNAs, focal CNAs and SNVs. This approach can therefore be used to longitudinally follow clonal evolution across the course of the disease and precision medicine in patients with MM.

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. A method comprising:
   determining that circulating free DNA (cfDNA), DNA/RNA from a circulating exosome, or DNA from a circulating tumor cell (CTC) from a blood biopsy from a human subject has each of four gene abnormalities, wherein the four gene abnormalities are:
   a single nucleotide variation (SNV) that is CR1 (p.R2194*), an SNV that is CR1 (p.M2208T), an SNV that is TMPRSS13 (p.A77G), and an SNV that is TMPRSS13 (p.Q78R), and HBG1 (p.A137G);
   wherein the determining comprises performing whole-exome sequencing and/or targeted deep sequencing of the cfDNA, the DNA/RNA from the circulating exosome, or the DNA from the CTC.

2. The method of claim 1, wherein the determining comprises analysis of all or part of an exome.

3. The method of claim 1, further comprising treating the human subject with a therapeutic agent for treatment of multiple myeloma.

4. A method comprising:
   detecting in circulating free DNA (cfDNA), DNA from a circulating tumor cell (CTC), DNA from a circulating exosome (exoDNA), or RNA from a circulating exosome from a human subject each of four genetic abnormalities, wherein the four genetic abnormalities are an SNV that is CR1 (p.R2194*), an SNV that is CR1 (p.M2208T), an SNV that is TMPRSS13 (p.A77G), and an SNV that is TMPRSS13 (p.Q78R); and wherein the detecting comprises performing whole-exome sequencing and/or targeted deep sequencing of the cfDNA, the DNA from the CTC, the exoDNA, or the RNA from the circulating exosome; and
   treating the human subject with a therapeutic agent for treatment of multiple myeloma.

* * * * *

UNITED STATES PATENT AND TRADEMARK OFFICE
CERTIFICATE OF CORRECTION

PATENT NO. : 11,124,838 B2
APPLICATION NO. : 15/742815
DATED : September 21, 2021
INVENTOR(S) : Irene Ghobrial, Salomon Manier and Yuji Mishima Page 1 of 1

It is certified that error appears in the above-identified patent and that said Letters Patent is hereby corrected as shown below:

On the Title Page

Right column, Line 5 in the Abstract:
Delete "bio markers" and insert -- biomarkers --, therefor.

In the Claims

Column 39, Line 23, in Claim 1:
Delete "(p.Q78R), and HBG1 (p.A137G);" and insert -- (p.Q78R); --, therefor.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*